(12) United States Patent
Hirose et al.

(10) Patent No.: US 7,768,702 B2
(45) Date of Patent: Aug. 3, 2010

(54) MEDICAL STEREO OBSERVATION SYSTEM

(75) Inventors: Kenji Hirose, Hachioji (JP); Tomonori Ishikawa, Hachioji (JP); Kazuo Morita, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 563 days.

(21) Appl. No.: 11/517,714

(22) Filed: Sep. 8, 2006

(65) Prior Publication Data

US 2007/0058249 A1    Mar. 15, 2007

(30) Foreign Application Priority Data

Sep. 9, 2005  (JP) ............... 2005-261670
Sep. 14, 2005  (JP) ............... 2005-266808

(51) Int. Cl.
*G02B 21/22* (2006.01)
*G02B 21/00* (2006.01)

(52) U.S. Cl. .................. 359/378; 359/368; 359/376

(58) Field of Classification Search ......... 359/368–390, 359/618, 637
See application file for complete search history.

(56) References Cited

U.S. PATENT DOCUMENTS

| 5,793,523 A | 8/1998 | Twisselmann |
| 5,971,540 A * | 10/1999 | Ofner ................... 351/158 |
| 5,995,282 A * | 11/1999 | Akiyama et al. ............ 359/384 |
| 6,313,952 B1 | 11/2001 | Yonezawa |
| 6,396,627 B1 | 5/2002 | Tachihara et al. |
| 2003/0133191 A1 | 7/2003 | Morita et al. |
| 2003/0218720 A1 | 11/2003 | Morita et al. |
| 2005/0174655 A1 | 8/2005 | Straehle et al. |

FOREIGN PATENT DOCUMENTS

| EP | 0 642 275 | 3/1995 |
| EP | 0 827 349 | 3/1998 |
| JP | 58-95316 | * 6/1983 | ................. 359/380 |
| JP | 8-194275 | * 7/1996 | ................. 359/368 |
| JP | 08-201940 | 8/1996 |
| JP | 08-313828 | 11/1996 |
| JP | 09-037302 | 2/1997 |
| JP | 2003-233031 | 8/2003 |

* cited by examiner

*Primary Examiner*—Thong Nguyen
(74) *Attorney, Agent, or Firm*—Kenyon & Kenyon LLP

(57) ABSTRACT

A medical stereo observation system includes a stereo imaging unit producing a first image for a left eye and a second image for a right eye that mutually have parallax and a stereo display unit capable of displaying stereoscopically the images produced by the stereo imaging unit. The stereo imaging unit has a first imaging optical system producing the first image for the left eye and a second imaging optical system producing the second image for the right eye, and focal positions of these imaging optical systems are located far away from the intersection of optical axes of the imaging optical systems, viewed from the stereo imaging unit. Whereby, a large-depth space can be comfortably observed in a wide range and a viewer can observe an observation object without bringing about a feeling of fatigue.

13 Claims, 37 Drawing Sheets

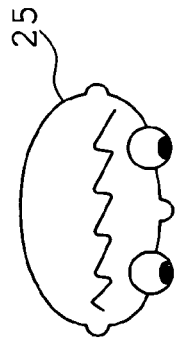
FIG. 3A
PRIOR ART
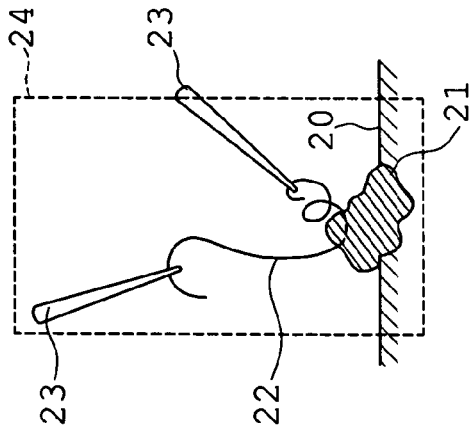
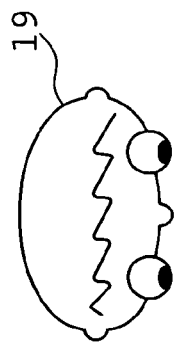
FIG. 3B
PRIOR ART
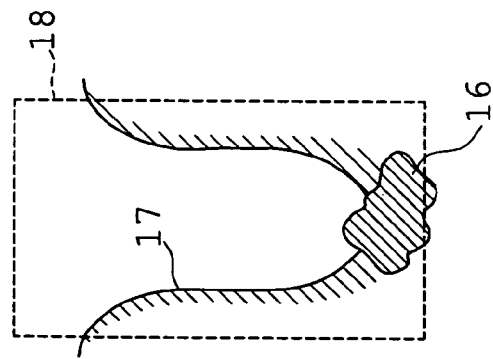

PART TO BE OPERATED $$1 \times \beta \times \sin\frac{\alpha}{2} = 1' \times \beta' \times \sin\frac{\alpha}{2}$$

$$1 \times \beta \times \sin\frac{\alpha}{2} = 1' \times \beta' \times \sin\frac{\alpha}{2}$$

FIG. 34
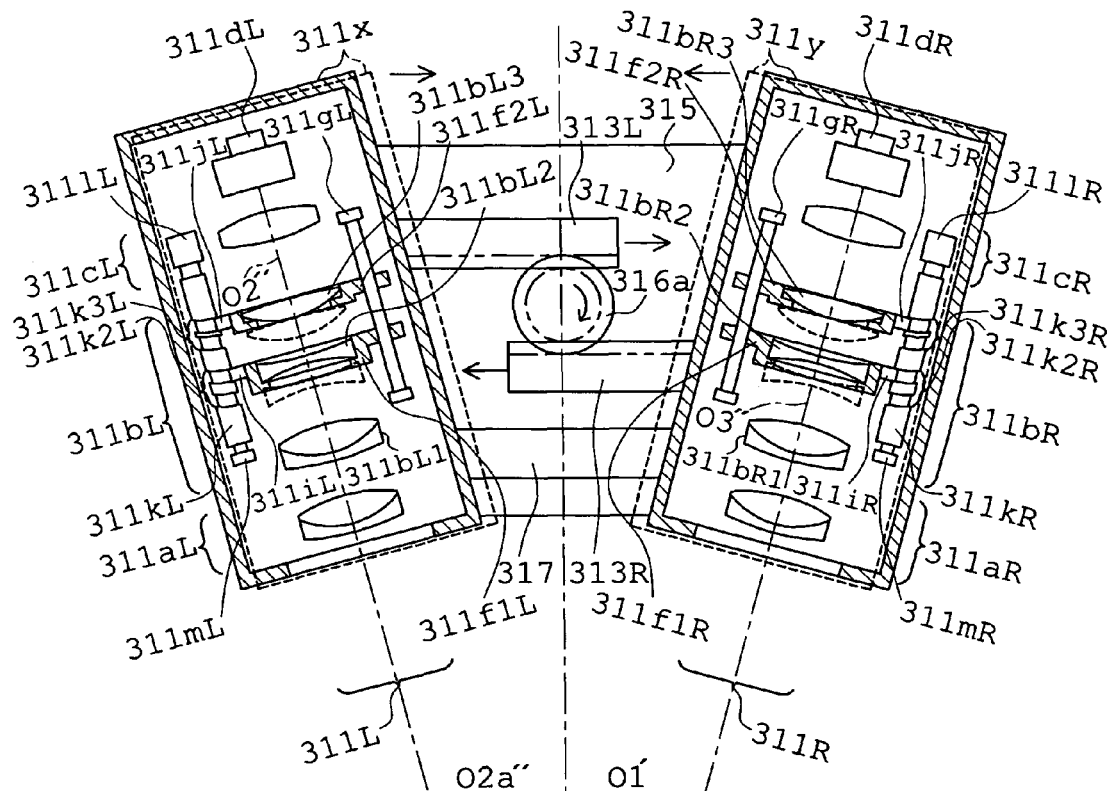
POSITION OF
INTERSECTION
IS SHIFTED BY
$(1-1')\cos\frac{\alpha}{2}$
$1 \times \beta \times \sin\frac{\alpha}{2} = 1' \times \beta' \times \sin\frac{\alpha}{2}$
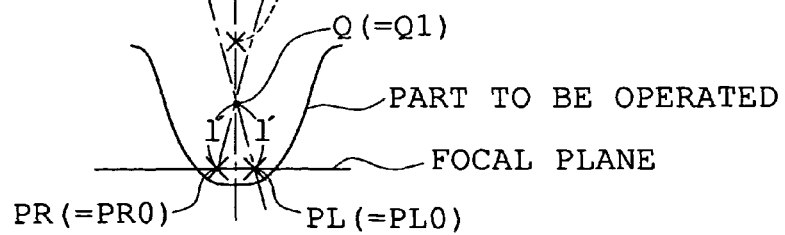

POSITION OF INTERSECTION OF OPTICAL AXES FOR IMAGING

PL=PR=Q

PART TO BE OPERATED

IMAGE DISPLAY SURFACE

Q

PART TO BE OPERATED

ER

EL

POSITION OF INTERSECTION OF OPTICAL AXES FOR IMAGING

PART TO BE OPERATED

Q

PL

PR m

M

M>m

IMAGE DISPLAY SURFACE

Q

PART TO BE OPERATED

ER

EL

MEDICAL STEREO OBSERVATION SYSTEM

This application claims benefits of Japanese Application No. 2005-261670 filed in Japan on Sep. 9, 2005 and No. 2005-266808 filed in Japan on Sep. 14, 2005, the contents of which are hereby incorporated by reference.

BACKGROUND OF THE INVENTION

1. Field of the Invention

This invention relates to a medical stereo observation system suitable for the stereo observation of a medical image used in a surgical operation, and particularly in neurosurgery, otolaryngology, orthopedic and plastic surgery, obstetrics and gynecology, or ophthalmology.

2. Description of Related Art

In recent years, the technique of using the medical stereo observation system, such as a stereoendoscope or a surgical (stereo) microscope, has been popularized in the field of medical treatment (notably surgery). In general, the medical stereo observation system is of a binocular type, and includes a stereo imaging unit incorporating imaging optical systems and image sensors to form left and right images with parallax of an observation object, a stereo image signal processing unit in which a stereo image is produced by the image signals of the left and right images derived from the stereo imaging unit, and a stereo display unit displaying the stereo image of the stereo image signal processing unit. In the medical stereo observation system, the images of the object are formed on the imaging surfaces of the image sensors by the imaging optical systems of the stereo imaging unit. In order to obtain the left and right images with parallax, various techniques are used in the imaging optical systems.

The left and right images obtained by the image sensors are transmitted as the image signals from the stereo imaging unit to the stereo image signal processing unit. The stereo image signal processing unit performs signal processing necessary for the stereo display unit provided behind the signal processing unit. The stereo display unit forms the left and right images on display elements on the basis of the stereo image sent from the stereo image signal processing unit. In order to separately transmit the left and right images to a viewer's eyes, various techniques are also used in the stereo display unit.

As a typical example of the technique of a stereo display unit, there is a virtual-image stereo observation type in which light is projected directly on the left and right pupils (eyes) of the viewer corresponding to the left and right images by optical systems located very closed to the viewer's face so that image information of a large image plane is equivalently observed stereoscopically as a virtual image. A conventional technique of a system combining the stereoendoscope with the virtual-image stereo observation type stereo display unit is set forth, for example, in Japanese Patent Kokai No. Hei 8-313828. This stereo observation system establishes the relationship between the imaging field angle of the stereoendoscope and the image observation field angle of the virtual-image stereo observation type display unit in order to observe the image of the stereoendoscope in a natural, virtual reality.

Such a conventional stereo observation system, as mentioned above, includes an imaging section producing images with parallax and an image display section displaying the images with parallax produced in the imaging section to make the viewer to fuse stereoscopically the images. The imaging section, for example, as disclosed in Japanese Patent Kokai No. Hei 8-201940, has two imaging optical systems for left and right eyes and adjusts the focal positions of the imaging optical systems for left and right eyes to a position required for the observation on an observation object to produce the images with parallax. In this case, the focal positions of the imaging optical systems for left and right eyes coincide with an intersection of their optical axes.

Various display devices of the stereo images used as the image display sections are known. For example, a display device capable of making the stereo image observation without mounting spectacles provided with observation optical systems and shutter functions on the face is disclosed in Japanese Patent Kokai No. 2003-233031. In an image display device disclosed here, images for left and right eyes are projected on a display panel surface by projection optical systems for left and right eyes so that the left and right images are collected at the positions of left and right eyes of the viewer and thereby collected left and right images with parallax are observed and fused to make the stereo observation. In this image display device, the optical axes of the projection optical systems for left and right eyes cross on the display panel surface and are reflected. Light of the projection optical systems for left and right eyes, reflected by the display panel surface is collected at the positions of the left and right eyes of the viewer. In this case, the focal positions adjusted to the position required for the observation on the observation object, produced by the imaging section are reproduced on the display panel surface.

On the other hand, in conventional neurosurgery, a surgical microscope is used in order to carry out a magnification observation on a fine part to be operated. In organs including fine tissues, such as brains, it is difficult to recognize their structural tissues with the naked eye and thus the treatment of organs is made under the microscope. Moreover, the operation of neurosurgery is such as not only to make observations on very important and delicate tissues like blood vessels and nerves in a very narrow region, but also to make the treatment that blood vessels or nerves are connected or blood vessels and nerves are avoided to remove a tumor. For this, it becomes important to make the stereo observation. In such medical circumstances, the observation object, such as a part to be operated, of brains, often has a hole-like and deep shape. Here, consider the case where the part to be operated is observed by the stereo observation system mentioned above. When the focal positions are imaged together with the bottom of the hole of the part to be operated, an image located on the front side of the bottom of the hole of the part to be operated, is reproduced in front of the display panel surface.

Generally, in the parallax of the images for left and right eyes, there is a limit to the image fusion with the left and right eyes of the viewer. The amount of parallax at a position separated by the depth from a plane of a desired depth position (the focal plane) on the observation object to which the focal positions are adjusted becomes large as it separates from the focal plane. Consequently, in a stereoscopic space reproduced on the display panel, a space limit by the amount of parallax that is an image fusion limit occurs.

When the hole-like part to be operated is observed in the conventional stereo observation system, the part to be operated is reproduced only in front of the display panel, and thus an image reproducing space situated on the far side (the inmost side) of the display panel cannot be effectively used. In addition, when a deep hole such as that reaching a deep portion of the brain is observed, an image close to the entrance of the hole is reproduced at a position where the image fusion limit is exceeded, and hence this is responsible for the fatigue of the eyes when the viewer makes the observation.

In the stereo observation system, when electronic zoom is applied during the observation of the observation object with a depth, the amount of parallax on the display panel surface of the observation object at a position separating from the focal positions of the imaging optical systems for left and right eyes, imaged by the imaging section is increased in accordance with the electronic zoom, and the image fusion of the viewer becomes difficult. In order to prevent this, as disclosed in Japanese Patent Kokai No. Hei 9-37302, a stereo imaging apparatus is proposed in which a distance between the observation object and the focal position is calculated and the position of a display image is shifted in accordance with the distance so that the image fusion is easily attained.

SUMMARY OF THE INVENTION

The medical stereo observation system according to the present invention comprises a stereo imaging unit producing a first image for a left eye and a second image for a right eye that mutually have parallax and a stereo display unit capable of displaying stereoscopically the images produced by the stereo imaging unit. In this case, the stereo imaging unit has a first imaging optical system producing the first image for the left eye and a second imaging optical system producing the second image for the right eye, and focal positions of these imaging optical systems are located far away from the intersection of optical axes of the imaging optical systems, viewed from the stereo imaging unit.

In the medical stereo observation system according to the present invention, when a distance from the intersection of the optical axes of the first imaging optical system and the second imaging optical system to a straight line connecting the center of the object-side focal plane of the first imaging optical system with the center of the object-side focal plane of the second imaging optical system is denoted by x, the distance x preferably satisfies the following condition:

$$\{5.9 \text{ (mm)} \times WD \text{ (mm)} \times \tan(\omega_1/2)\}/\{L \text{ mm} \times \tan(\alpha/2) + 5.9 \text{ (mm)} \times \tan(\omega_1/2)\}$$

$$\leq x \text{ (mm)} \leq$$

$$\{21.7 \text{ (mm)} \times WD \text{ (mm)} \times \tan(\omega_1/2)\}/\{L \text{ (mm)} \times \tan(\alpha/2) + 21.7 \text{ (mm)} \times \tan(\omega_1/2)\}$$

where WD is a working distance of the stereo imaging unit (a distance from the most object-side surface of the stereo imaging unit to object-side focal positions of the stereo imaging unit), $\omega_1$ is a diagonal field angle of each of the first and second imaging optical systems, $\alpha$ is an angle made on the object side by the optical axes of the first and second imaging optical systems, and L is a diagonal distance of the observation image in the stereo display unit.

The medical stereo observation system according to the present invention preferably comprises a stereo imaging unit producing a first image for a left eye and a second image for a right eye that mutually have parallax and a stereo display unit for a first viewer and a stereo display unit for a second viewer, capable of displaying stereoscopically the images produced by the stereo imaging unit. In this case, a vergence angle $\alpha A$ where the stereo display unit for the first viewer is observed and a vergence angle $\alpha B$ where the stereo display unit for the second viewer is observed satisfy the following condition:

$$0.5 \leq \alpha A/\alpha B \leq 2$$

In the medical stereo observation system according to the present invention, the first imaging optical system and the second imaging optical system preferably include objective optical systems, variable magnification optical systems, image-forming optical systems, and image sensors, one for each imaging optical system. The focal positions of these two imaging optical systems are shifted by preset amounts between the intersection of the optical axes of the two imaging optical systems and the focal positions of the two imaging optical systems at a low magnification in association with a magnification change by the variable magnification optical systems.

The medical stereo observation system according to the present invention preferably has an intersection position shifting means shifting the intersection of the optical axes of the two imaging optical systems toward the object side in association with the magnification change by the variable magnification optical systems.

In the medical stereo observation system according to the present invention, the intersection position shifting means preferably shifts the intersection of the optical axes of the two imaging optical systems so as to cancel a gap between a preset depth position required for the observation in the observation object with a depth and the focal positions, caused by shifting the focal positions of the two imaging optical systems in association with the magnification change of the variable magnification optical systems.

In the medical stereo observation system according to the present invention, when an angle at which the optical axes of the two imaging optical systems cross in a first variable magnification mode is represented by $\alpha$; a distance, measured along the optical axis axis, from each of the focal positions of the two imaging optical systems to the intersection of the optical axes of the two imaging optical systems, by l; the magnification of each of the variable magnification optical systems of the two imaging optical systems, by $\beta$; an angle at which the optical axes of the two imaging optical systems cross in a second variable magnification mode different in magnification from the first variable magnification mode, by $\alpha'$; a distance, measured along the optical axis, from each of the focal positions of the two imaging optical systems to the intersection of the optical axes of the two imaging optical systems, by l'; and the magnification of each of the variable magnification optical systems of the two imaging optical systems, by $\beta'$, the focal positions of the two imaging optical systems preferably satisfy the following condition and at the same time, are shifted in association with the magnification change by the variable magnification optical systems:

$$l \cdot \beta \cdot \sin(\alpha/2) = l' \cdot \beta' \cdot \sin(\alpha'/2)$$

The medical stereo observation system according to the present invention preferably has an image-forming optical system moving means moving the image-forming optical systems along the optical axes of the image-forming optical systems in association with the magnification change by the variable magnification optical systems.

In the medical stereo observation system according to the present invention, when an angle at which the optical axes of the two imaging optical systems cross in a first variable magnification mode is represented by $\alpha$; a distance, measured along the optical axis, from each of the focal positions of the two imaging optical systems to the intersection of the optical axes of the two imaging optical systems, by l; the magnification of each of the variable magnification optical systems of the two imaging optical systems, by $\beta$; an angle at which the optical axes of the two imaging optical systems cross in a second variable magnification mode different in magnification from the first variable magnification mode, by $\alpha'$; a distance, measured along the optical axis, from each of the focal positions of the two imaging optical systems to the intersection of the optical axes of the two imaging optical systems, by l'; and the magnification of each of the variable magnification optical systems of the two imaging optical systems, by β', the image-forming optical system moving means preferably satisfies the following condition and at the same time, moves the focal positions of the two imaging optical systems in association with the magnification change by the variable magnification optical systems:

$$l \cdot \beta \cdot \sin(\alpha/2) = l' \cdot \beta' \cdot \sin(\alpha'/2)$$

In the medical stereo observation system according to the present invention, the intersection position shifting means preferably moves the two imaging optical systems along a straight line connecting the focal positions of the two imaging optical systems in association with the magnification change by the variable magnification optical systems.

In the medical stereo observation system according to the present invention, when an angle at which the optical axes of the two imaging optical systems cross in a first variable magnification mode is represented by α; a distance, measured along the optical axis, from each of the focal positions of the two imaging optical systems to the intersection of the optical axes of the two imaging optical systems, by l; the magnification of each of the variable magnification optical systems of the two imaging optical systems, by β; an angle at which the optical axes of the two imaging optical systems cross in a second variable magnification mode different in magnification from the first variable magnification mode, by α'; a distance, measured along the optical axis, from each of the focal positions of the two imaging optical systems to the intersection of the optical axes of the two imaging optical systems, by l'; and the magnification of each of the variable magnification optical systems of the two imaging optical systems, by β', the two imaging optical systems preferably satisfy the following condition and at the same time, are moved in association with the magnification change by the variable magnification optical systems:

$$l \cdot \beta \cdot \sin(\alpha/2) = l' \cdot \beta' \cdot \sin(\alpha'/2)$$

In the medical stereo observation system according to the present invention, the angle at which the optical axes of the two imaging optical systems cross is kept constantly in a variable magnification mode ranging from the low magnification to the high magnification.

In the medical stereo observation system according to the present invention, when the distance l, measured along the optical axis axis, from each of the focal positions of the two imaging optical systems to the intersection of the optical axes of the two imaging optical systems is changed to a distance l' in accordance with the magnification change by the variable magnification optical systems, the intersection position shifting means preferably shifts the position of the intersection of the optical axes of the two imaging optical systems by (l-l') cos(α/2).

According to the present invention, even when a part required for the observation is a narrow hole-like domain, an image fusible range can be effectively utilized and fatigue given to the viewer is lessened as far as possible so that a magnified image with high resolution can be observed stereoscopically. Such a medical stereo observation system is obtained.

These and other features and advantages of the present invention will become apparent from the following detailed description of the preferred embodiments when taken in conjunction with the accompanying drawings.

BRIEF DESCRIPTION OF THE DRAWINGS

FIGS. 3A and 3B are views showing different observation ranges in the stereo observation system used for medical treatment;

FIG. 34 is an explanatory view showing the optical structure of imaging optical systems for left and right eyes used in the medical stereo observation system of the eighth embodiment, positions of individual optical members at a high magnification, an intersection of optical axes on the observation object side in the imaging optical systems for left and right eyes, and individual focal positions of the imaging optical systems for left and right eyes relative to a focal plane;

DETAILED DESCRIPTION OF THE PREFERRED EMBODIMENTS

Before undertaking the description of the embodiments, reference is made to fatigue that occurs in the stereo observation by using the medical stereo observation system.

In the stereo display unit of the stereo observation system, as shown in FIGS. 1A-1E, an observation object 6 is reproduced in accordance with the amount of parallax between the left and right images at various positions with respect to a display surface 5 of the stereo display unit. In this case, relations between a vergence distance of the viewer (a distance from a position where left and right lines of sight cross in viewing reproducing space to the eyes) and an adjusting distance (a distance from focal positions of the eyes in viewing the images to the eyes) are various in individual states. When the amount of parallax of the left and right images is zero (FIG. 1C), the vergence distance and the adjusting distance coincide with each other, while when the left and right images have the amount of parallax (FIGS. 1A, 1B, 1D, and 1E), they do not coincide.

In an ordinary natural observation, the vergence distance and the adjusting distance are coincident, and it is known that, in a state where there is a considerable difference between the vergence distance and the adjusting distance in the stereo observation, an unnatural observation is forced on the viewer and remarkably influence eyestrain and a feeling of discomfort. In order to enable the viewer to make the stereo observation without feeling fatigue and discomfort, it is necessary to hold the difference between the vergence distance and the adjusting distance within a certain limit.

Figure 23:
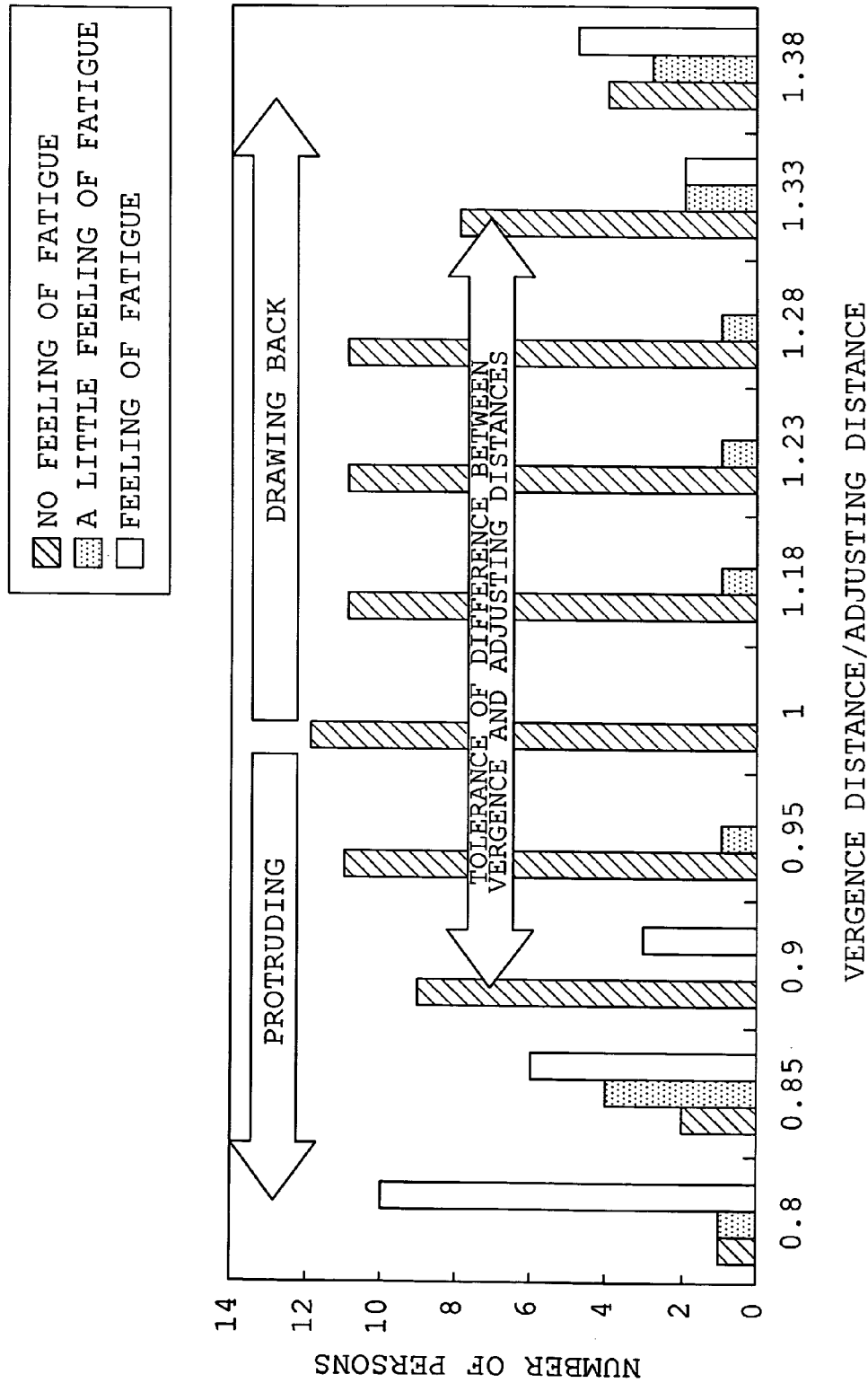
FIG. 23 is a view showing the result of the discussion on the tolerance of the difference between the vergence distance and the adjusting distance.

The result of the discussion on the tolerance of the difference between the vergence distance and the adjusting distance is shown in FIG. 23. In this discussion, twelve persons to be examined carry out stereo observations in various relations between the vergence distance and the adjusting distance of the stereo display device to evaluate whether they feel physical fatigue. By the above discussion, the conclusion of the tolerance of the difference between the vergence distance and the adjusting distance is obtained as follows:

$$0.9 \leq \text{vergence distance/adjusting distance} \leq 1.325$$

By the tolerance of the difference between the vergence distance and the adjusting distance, a spatial limit at a reproducing position where the observation object can be comfortably observed is provided close to the display surface. Space within this limit is thought of as a comfort observable range 7, which is narrow on the side of a viewer 8 in the proximity of the display surface and extends widely on the far side of the viewer.

Figure 1A:
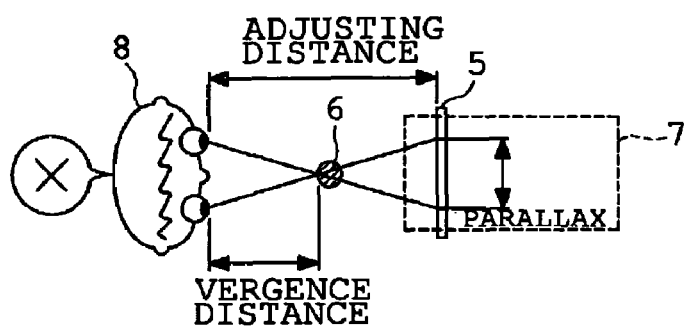
FIGS. 1A-1E are views showing states where an observation object is reproduced at various positions with respect to the display surface of a stereo display unit.
Figure 1B:
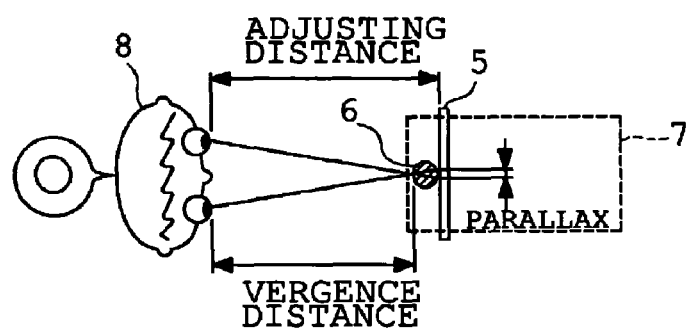
Figure 1C:
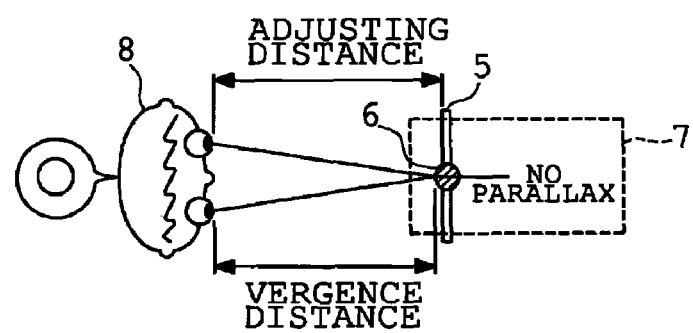
Figure 1D:
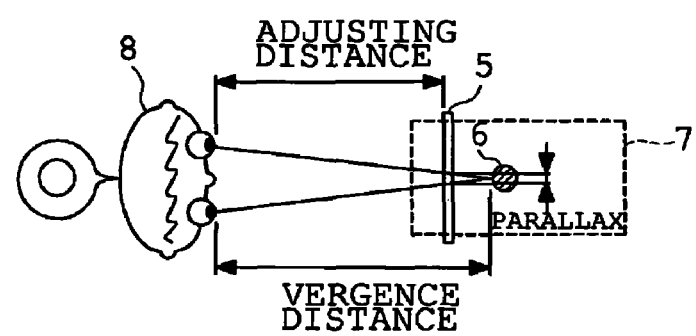
Figure 1E:
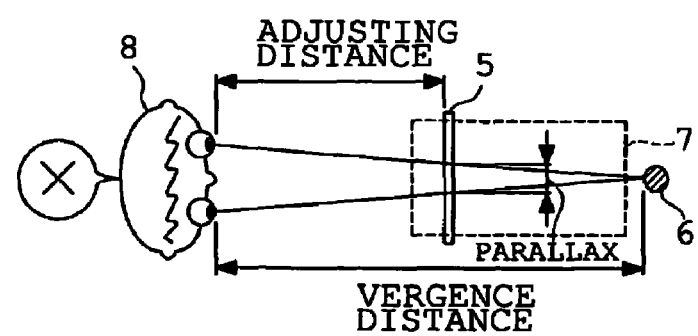
Figure 2:
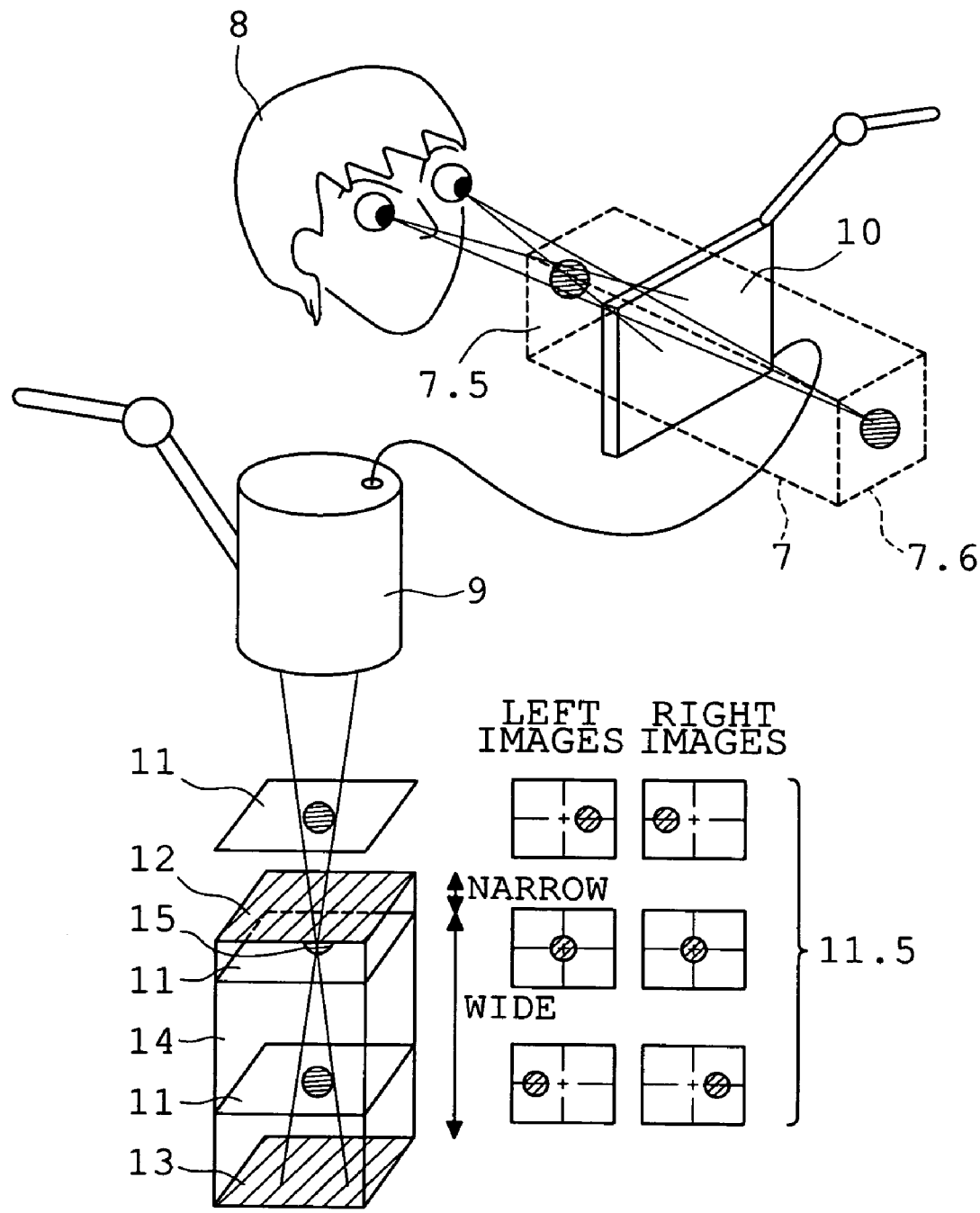
FIG. 2 is a view showing a process that a stereo imaging unit produces left and right images with parallax in accordance with the position of the observation object and supplies the images to the stereo display unit.

As shown in FIG. 2, a stereo imaging unit 9 that is another unit of the stereo observation system produces left and right images 11.5 with parallax in accordance with the position of an observation object 11 relative to the stereo imaging unit and supplies these images to a stereo display unit 10. Space sandwiched between a position 12 of the observation object relative to the stereo imaging unit 9 where the observation object is reproduced at a most viewer-side position 7.5 of the comfort observable range 7 and a position 13 of the observation object relative to the stereo imaging unit 9 where the observation object is reproduced at a most opposite-side position 7.6 of the comfort observable range 7 constitutes a comfort observable range 14 in "real space". The comfort observable range 14 in real space is narrow on the stereo-imaging-unit side and extends widely on the far side of the stereo imaging unit with respect to an intersection 15 of the optical axes of left and right imaging optical systems in the stereo imaging unit 9.

On the other hand, the stereo observation system used for medical treatment is chiefly used as an observation means in the surgical operation, and as shown in FIG. 3A, observation is often made in a state where the tissue is incised until an object 16, such as a tumor, in the body is reached. In this case, while the viewer carefully observes the object 16, he also devotes attention to an incision section 17 and must give great care to an issue of blood from the incision section. Thus, an observation range required for the viewer is a domain 18 surrounded by a dotted line in the figure and becomes space that has a depth extending from the object 16 to be most carefully observed toward the side of a viewer 19.

As shown in FIG. 3B, even in the case where a part 21 to be operated, situated on a body surface 20 is treated, the viewer must give great care to not only the part 21 to be operated, but also states of a gut 22 and treatment tools 23, such as needle holders, to proceed the treatment. Thus, a necessary observation range is a domain 24 surrounded by a dotted line in the figure and in this case also, becomes space that has a depth extending from the part 21 to be operated that must be most carefully observed toward the side of a viewer 25.

Figure 4:
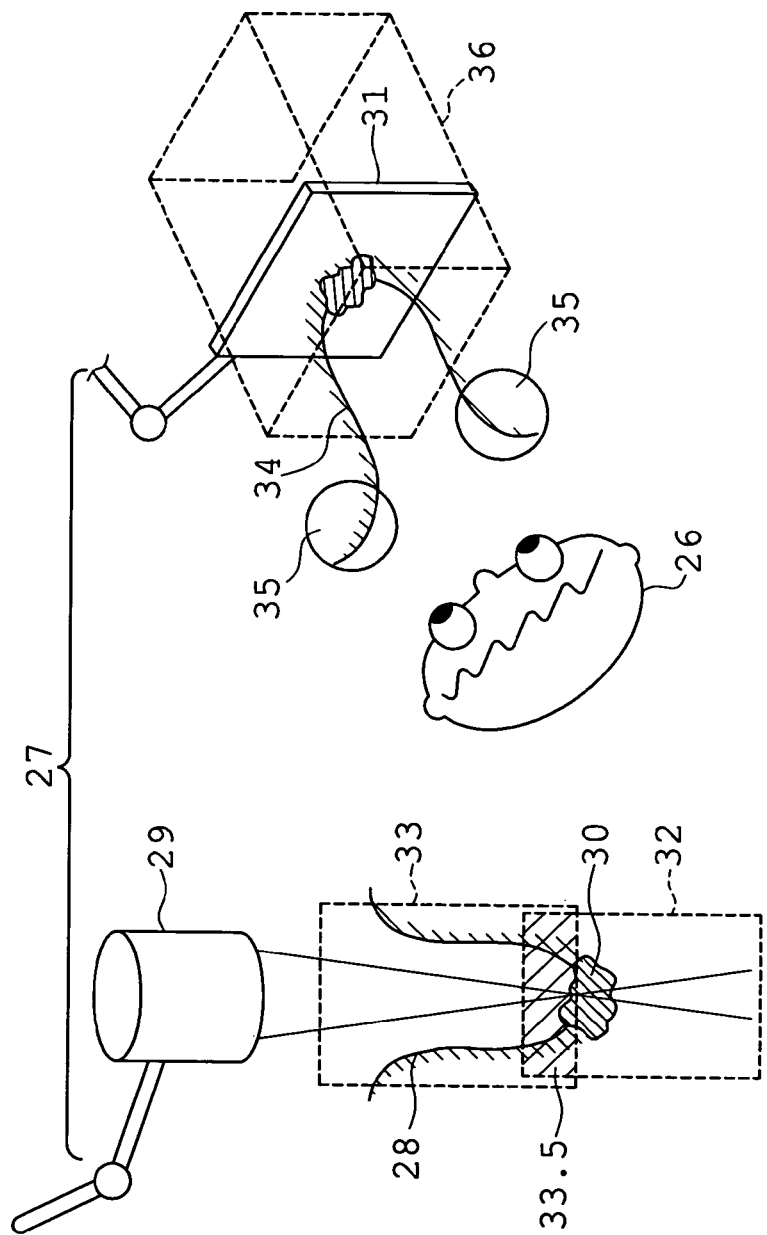
FIG. 4 is a view for explaining problems of a conventional stereo observation system.

FIG. 4 shows a case where a viewer 26 observes the observation object 16 such as that shown in FIG. 3A, using a stereo observation system 27. The viewer observes the observation image that is produced in such a way that a bottom 30 of the observation object having a depth in a depth direction is brought to a focus by a stereo imaging unit 29 and that is reproduced by a stereo display unit 31. In this case, a comfort observable range 32 in real space covered by the stereo imaging unit and a required range 33 for observation for the viewer (i.e., a range containing an incision section 28) overlap only in a portion 33.5 as shown in the figure. Consequently, a viewer-side portion 35 of an observation image space 34 reproduced in the stereo display unit 31 protrudes from a comfort observable range 36 covered by the stereo display unit, so that the viewer feels considerable fatigue when observing this protruded portion. This feeling of fatigue, as mentioned above, is created by a large shift exceeding the tolerance between the vergence distance and the adjusting distance and as a result, brings eyestrain and a feeling of discomfort to the viewer.

The present invention provides the medical stereo observation system in which the structure of the stereo imaging unit and a favorable relationship between the stereo imaging unit and the stereo display unit are established and thereby the stereo observation free from fatigue can be obtained.

The medical stereo observation system of the present invention comprises a stereo imaging unit producing a first image for a left eye and a second image for a right eye that mutually have parallax and a stereo display unit capable of displaying stereoscopically the images produced by the stereo imaging unit. In this case, the stereo imaging unit has a first imaging optical system producing the first image for the left eye and a second imaging optical system producing the second image for the right eye, and focal positions of individual imaging optical systems are located far away from the intersection of optical axes of individual imaging optical systems, viewed from the stereo imaging unit.

The optical axis of each of the imaging optical systems may be constructed as a straight line connecting the center of the entrance pupil of the imaging optical system with the object-side conjugate point of the center of the imaging area of an image sensor. The intersection of the optical axes of the first and second imaging optical systems may be replaced with a point where the optical axes approach nearest to each other.

Figure 5:
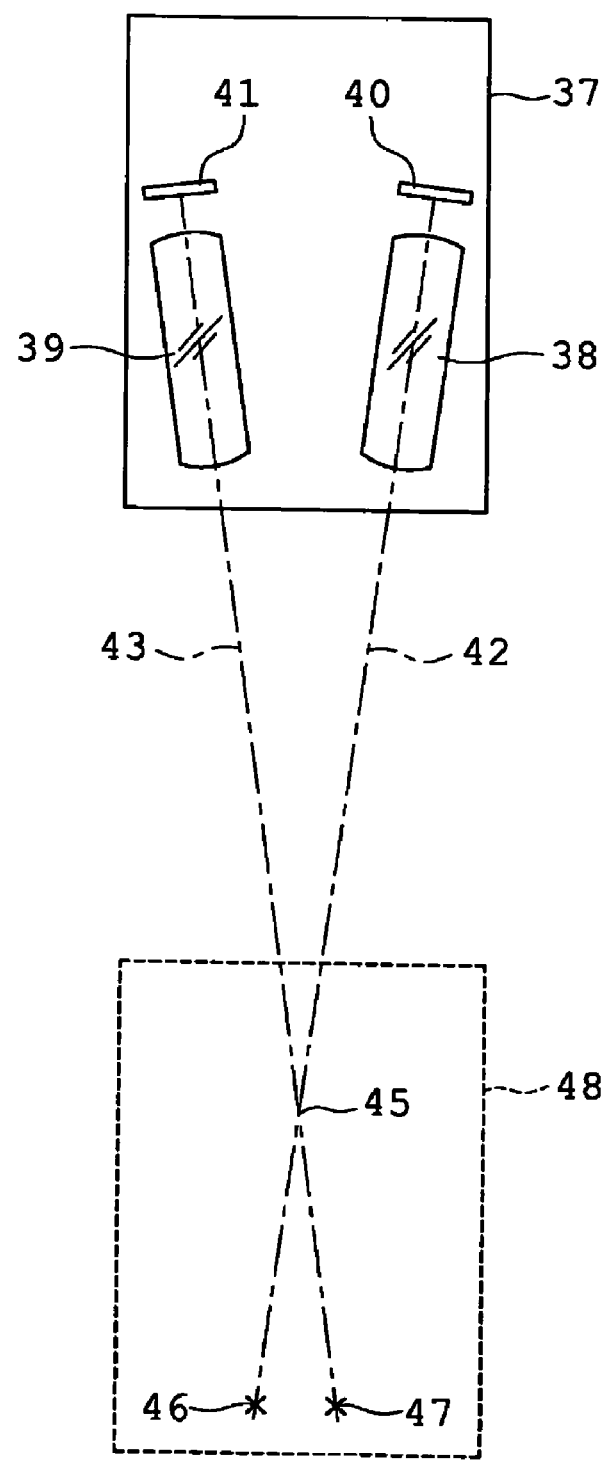
FIG. 5 is a view showing a fundamental structure of the stereo observation system according to the present invention.

Using FIG. 5, this arrangement will be explained. In this figure, reference numeral 37 denotes a stereo imaging unit, 38 denotes a second imaging optical system for acquiring an image for a right eye of the stereo imaging unit, 39 denotes a first imaging optical system for acquiring an image for a left eye, 40 and 41 denote imaging means, 42 denotes the optical axis of the second imaging optical system, 43 denotes the optical axis of the first imaging optical system, 45 denotes the intersection of the optical axes of the first and second imaging optical systems, 46 denotes the focal position of the second imaging optical system, 47 denotes the focal position of the first imaging optical system, and 48 denotes the comfort observable range in real space of the stereo imaging unit.

In the comfort observable range 48 in real space of the stereo imaging unit, its extension in the depth direction is governed by the amount of parallax between left and right images produced by the stereo imaging unit. Consequently, even when the focal positions 46 and 47 of the imaging optical systems that do not affect the occurrence of parallax are set at any positions, the positional relationship of the comfort observable range in real space of the stereo imaging unit to the stereo imaging unit 37 (more specifically, to the intersection 45 of the optical axes) remains unchanged.

According to this arrangement, the focal points 46 and 47 of the imaging optical systems are located far away from the intersection 45 of the optical axes, viewed from the stereo imaging unit 37, and thereby the comfort observable range 48 in real space can be widely ensured on the front side of the focal positions 46 and 47, viewed from the stereo imaging unit 37. When the observation object, such as that shown in FIG. 3A, is observed, the space 17 required for the viewer can be widely covered by the comfort observable range 18 in real space of a stereo imaging unit, and hence the viewer can observe the observation object without bringing about the feeling of fatigue.

In the medical stereo observation system of the present invention, when a distance from the intersection 45 of the optical axes of the first imaging optical system 39 and the second imaging optical system 38 to a straight line connecting the center of the object-side focal plane of the first imaging optical system with the center of the object-side focal plane of the second imaging optical system is denoted by x, the distance x satisfies the following condition:

$$\{5.9 \times WD \times \tan(\omega1/2)\}/\{L \times \tan(\alpha/2)+5.9 \times \tan(\omega1/2)\}$$
$$\leq x \text{ (mm)} \leq$$
$$\{21.7 \times WD \times \tan(\omega1/2)\}/\{L \times \tan(\alpha/2)+21.7 \times \tan(\omega1/2)\} \quad (1)$$

where WD is a working distance of the stereo imaging unit (a distance from the most object-side surface of the stereo imaging unit to object-side focal positions of the stereo imaging unit), ω1 is a diagonal field angle of each of the first and second imaging optical systems, α is an angle made on the object side by the optical axes of the first and second imaging optical systems, and L is a diagonal distance of the observation image in the stereo display unit.

Figure 6:
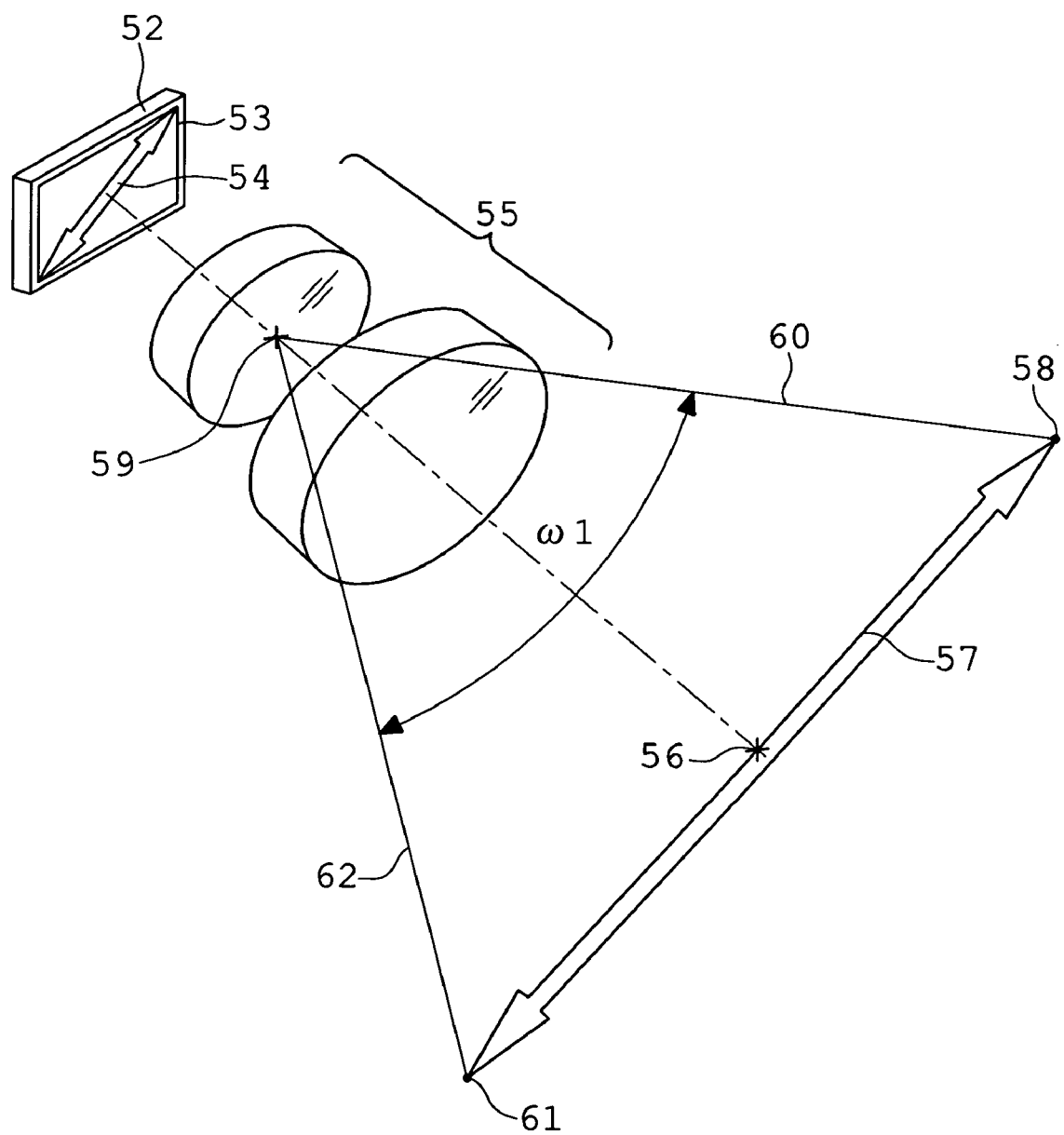
FIG. 6 is an explanatory view showing the diagonal field angle of an imaging optical system.

The angle ω1 will be described in detail with reference to FIG. 6. The angle ω1 represents a diagonal field angle of each of the imaging optical systems of the stereo imaging unit 37. More specifically, a diagonal straight line 54 of an imaging area 53 of an imaging means 52 for a left eye of the stereo imaging unit is projected at a position 56 on the object side (the subject side) by an imaging optical system 55 for a left eye, and the angle ω1 refers to an angle made by a straight line 60 connecting one end point 58 of a projected diagonal straight line 57 and a center 59 of the entrance pupil of the imaging optical system 55 for the left eye with a straight line 62 connecting the other end point 61 of the projected diagonal straight line 57 and the center 59 of the entrance pupil. The diagonal field angle for the right eye, not shown, is exactly the same as the above description and thus its explanation is omitted.

Also, when the imaging area of the imaging means 52 is limited to the shape of a stop or a round shape taken by an electrical means, a straight line of the maximum length in a limited imaging area is used instead of the diagonal straight line.

Figure 7A:
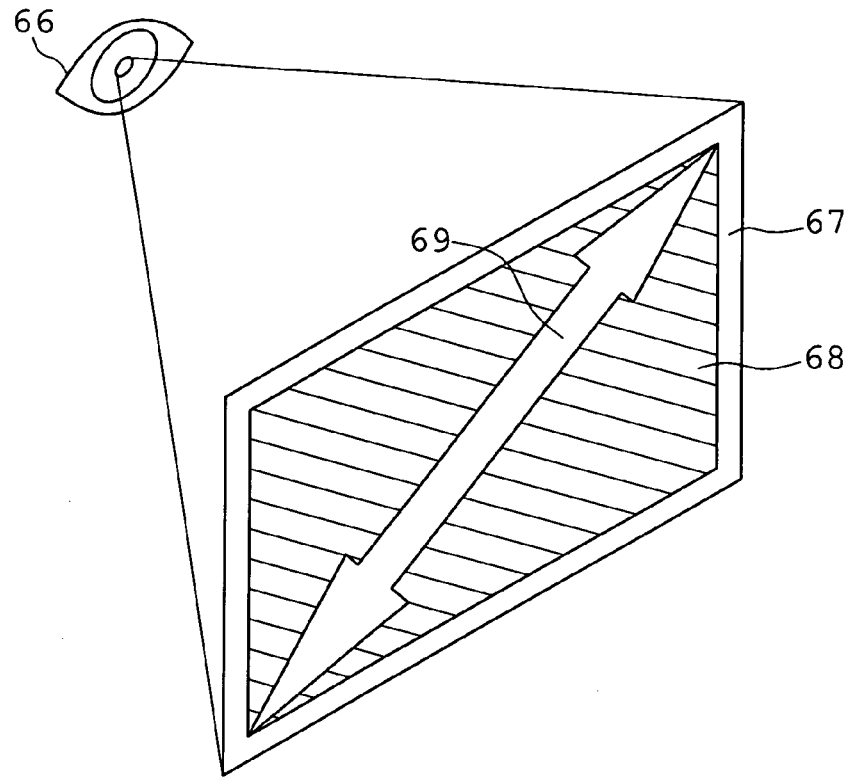
FIGS. 7A-7C are explanatory views, each showing the diagonal distance of the observation image in the stereo display unit.
Figure 7B:
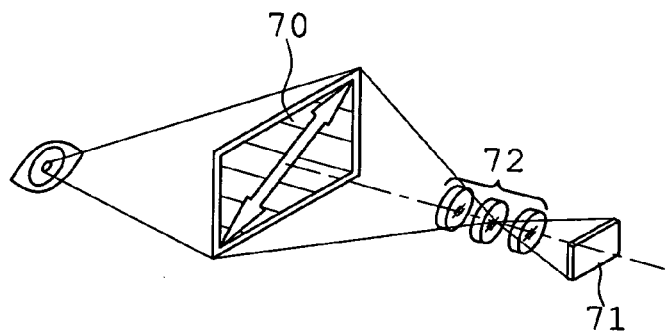
Figure 7C:
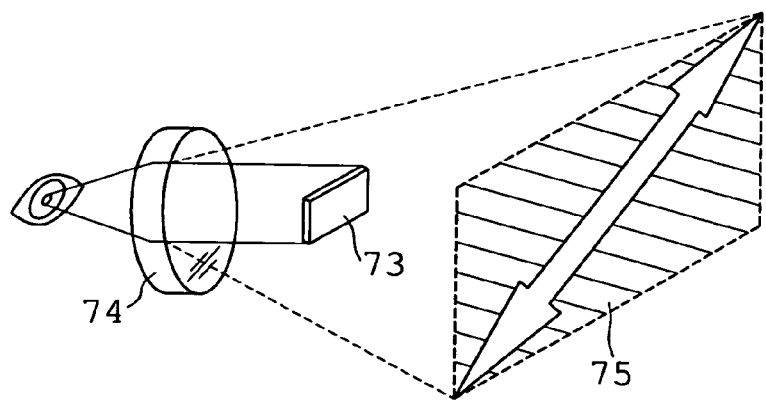

The distance L will be described in detail with reference to FIG. 7A. The distance L indicates the diagonal distance of the observation image in the stereo display unit. More specifically, it refers to the length of a diagonal line 69 across an observation image 68 displayed on an image display means 67 of the stereo display unit and observed by a viewer 66. Also, as shown in FIG. 7B, the observation image may be not an image itself displayed on the image display means, but a real image 70 such that an image displayed on an image display means 71 is projected by an optical means 72. Further, as shown in FIG. 7C, it may be a virtual image 75 such that an image displayed on an image display means 73 is projected by an optical means 74 such as an eyepiece optical system. In addition, when the observation image is limited to a round shape smaller than a display area of the image display means 67 and is displayed, the length of the maximum straight line in a limited display area is used instead of the diagonal straight line.

In the comfort observable range in real space of the stereo imaging unit, as mentioned above, the extension in the depth direction is governed by the amount of parallax between the left and right images produced by the stereo imaging unit and is secured before and behind the intersection of the optical axes of the first and second imaging optical systems of the stereo imaging unit on the basis of the intersection.

Condition (1) is provided to determine where the focal positions should be located with respect to the intersection of the optical axes of the first and second imaging optical systems. In other words, it determines where the focal positions should be located with respect to the comfort observable range in real space of the stereo imaging unit.

Figure 8:
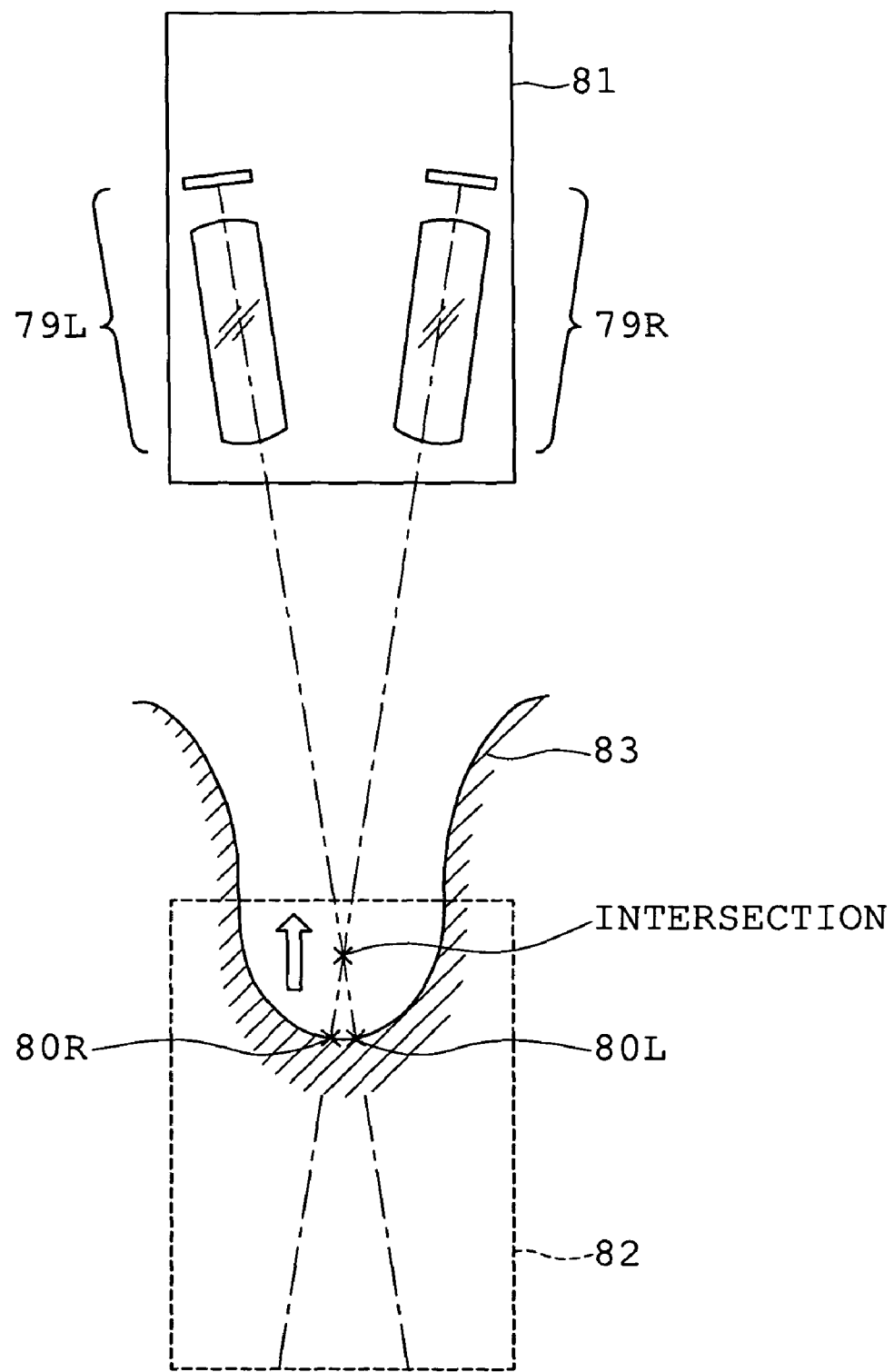
FIG. 8 is an explanatory view showing the comfort observable range where Condition (1) of the present invention is not satisfied.
Figure 9:
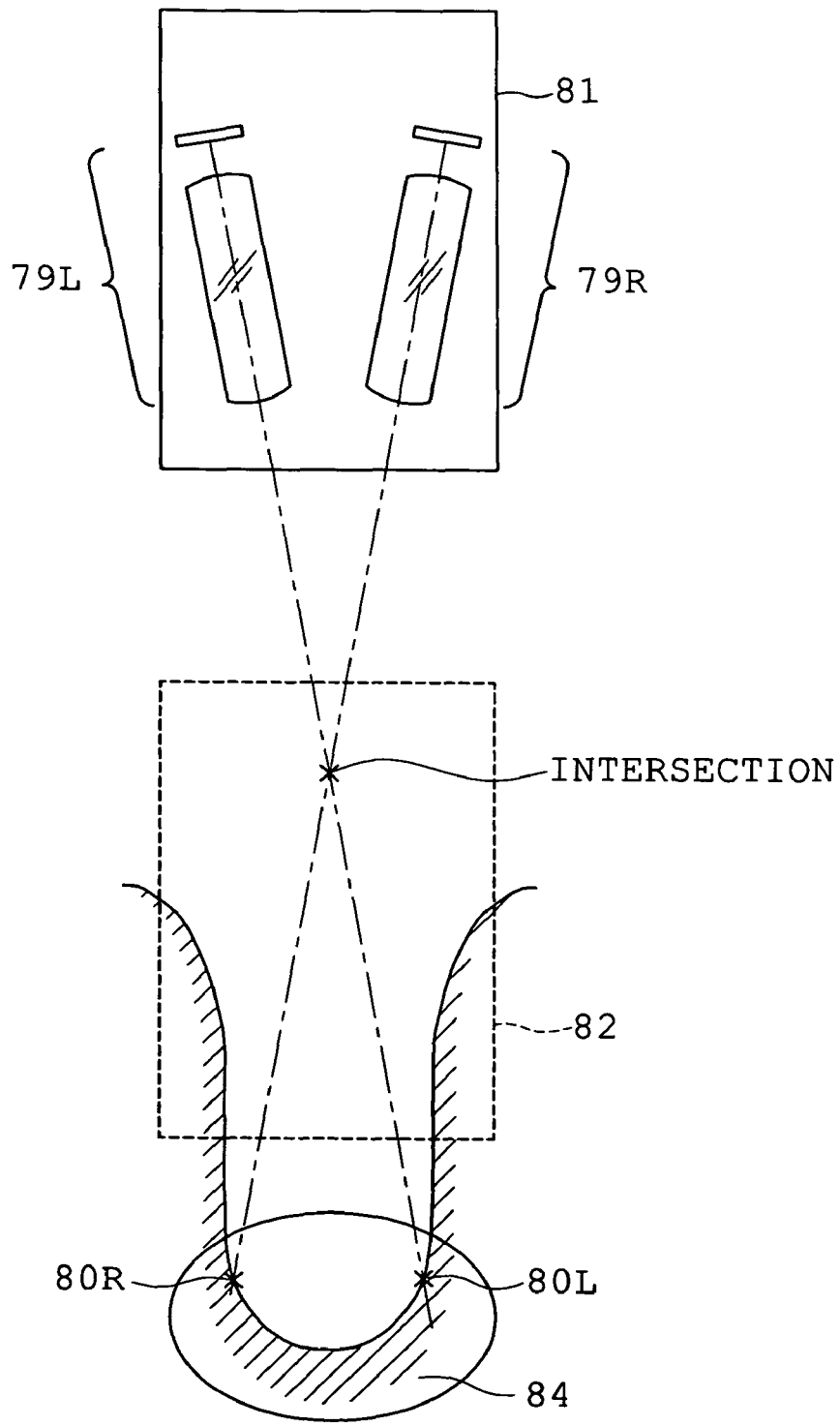
FIG. 9 is another explanatory view showing the comfort observable range where Condition (1) of the present invention is not satisfied.

If the locations of the focal positions of the first and second imaging optical systems are below the lower limit of Condition (1), as shown in FIG. 8, a comfort observable range 82 in real space of a stereo imaging unit 81 cannot be widely ensured on the upper side of individual focal positions 80R and 80L of first and second imaging optical systems 79R and 79L. As a result, a large-depth space 83 cannot be comfortably observed in a wide range. If they are beyond the upper limit of Condition (1), as shown in FIG. 9, the focal positions 80R and 80L of the first and second imaging optical systems 79R and 79L will protrude from the comfort observable range 82 in real space of the stereo imaging unit 81, and as such, a range 84 of a focused observation object cannot be comfortably observed.

Thus, when the medical stereo observation system is designed to satisfy Condition (1), the focal positions of the first and second imaging optical systems of the stereo imaging unit are located at optimum positions within the comfort observable range in real space of the stereo imaging unit. In this way, the large-depth space can be comfortably observed in a wide range and the viewer can observe the observation object without bringing about the feeling of fatigue.

The medical stereo observation system of the present invention comprises a stereo imaging unit producing a first image for a left eye and a second image for a right eye that mutually have parallax and a stereo display unit for a first viewer and a stereo display unit for a second viewer, capable of displaying stereoscopically the images produced by the stereo imaging unit. In this case, a vergence angle αA where the stereo display unit for the first viewer is observed and a vergence angle αB where the stereo display unit for the second viewer is observed satisfy the following condition:

$$0.5 \leq \alpha A/\alpha B \leq 2 \quad (2)$$

Figure 22:
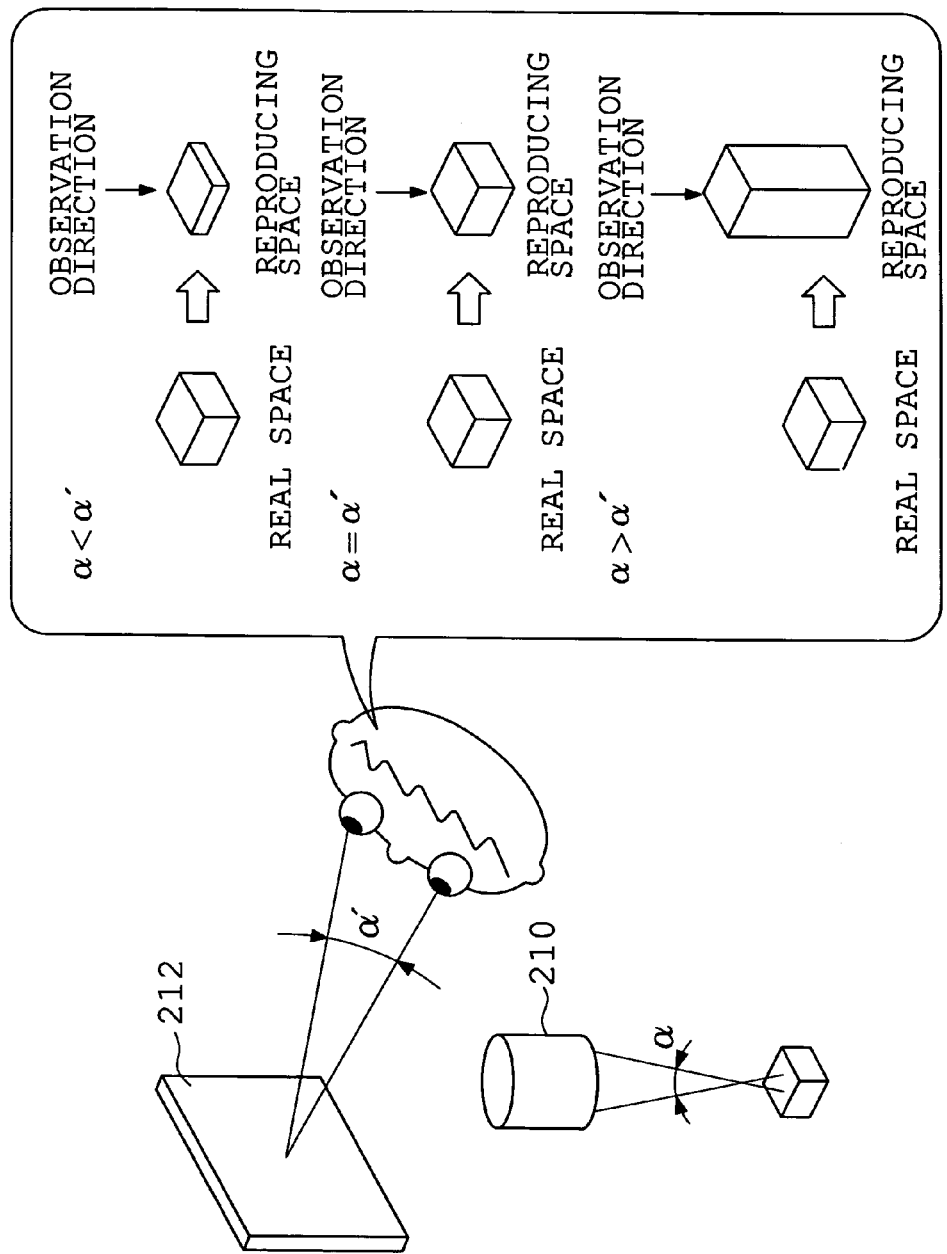
FIG. 22 is a view showing that reproducing space by the stereo observation system according to the present invention is distorted, with respect to the real space to be observed, by the relationship between an internal inclination angle α of the imaging unit and a vergence angle α' at which the display unit is observed.

The reproducing space obtained by the stereo observation system, as illustrated in FIG. 22, is reproduced so that the real space to be observed is distorted by the relationship between an internal inclination angle α of an imaging unit 210 and a vergence angle α' at which a display unit 212 is observed. When the internal inclination angle α of the imaging unit and the vergence angle α' of the display unit have the relation of α<α', the reproducing space distorted so as to collapse in an observation direction is observed when a cube in real space is observed. When the angles α and α' have the relation of α>α', the reproducing space distorted in so as to extend in an observation direction is observed when the cube in real space is observed. When the angles α and α' have the relation of α=α', the cube in real space is not distorted and is observed as the reproducing space magnified.

Not only does the distortion of the reproducing space give the observation of a spatially distorted observation object, but also it affects the treatment work that a part to be operated is touched, incised, and sutured with treatment tools in the surgical operation. For example, when the reproducing space is distorted so as to extend in the observation direction, the treatment tools slightly moved are enhanced and appear to be considerably moved in the reproducing space to be observed. This obstructs the induction of the treatment tools to a target. However, when a certain time is taken by the feedback from the observation image, the viewer can grow familiar with the relationship between the distortion of the reproducing space and the treatment work (motion). However, in the stereo observation system in which a plurality of display units (a first display unit and a second display unit) are connected to a single imaging unit so that a plurality of viewers can observe a part to be operated, a problem arises when the value of the vergence angle of the first display unit is largely different from the value of the vergence angle of the second display unit, and viewers using the first display unit and the second display unit often change places. In the surgical operation, the viewer may often change places with another in accordance with the progress of the operation.

Such a problem is that a distortion state of the reproducing space determined by the relationship between the internal inclination angle α of the imaging unit and the vergence angle of the first display unit is different from that of the reproducing space determined by the relationship between the internal inclination angle α of the imaging unit and the vergence angle of the second display unit, and thus when a viewer shifts from the first display unit to the second display unit, the viewer will create a feeling of discomfort with respect to the treatment work until he grows familiar with the distortion of the reproducing space of the second display unit. This feeling of discomfort of the treatment work is produced whenever the viewer shifts the display unit to be used, giving a feeling of fatigue to the viewer as a result.

Experiments show that when the vergence angle of the first display unit and that of the second display unit satisfy Condition (2), the feeling of discomfort of the treatment work in shifting the display unit is lessened. As such, when the medical stereo observation system satisfying Condition (2) is provided, the viewer can shift the display unit without producing the feeling of fatigue and the progress of the operation is not retarded.

In the conventional stereo observation apparatus, when the observation object of a hole-like shape, such as a part to be operated, is observed, the domain within the image fusion limit cannot be effectively utilized.

Thus, the applicant of the present invention has discussed methods such as those shown in FIGS. 36A-36D, described below, so that when the observation object has a hole-like shape, the domain within the image fusion limit is effectively utilized and the viewer can always easily make the stereo observation.

Figure 36A:
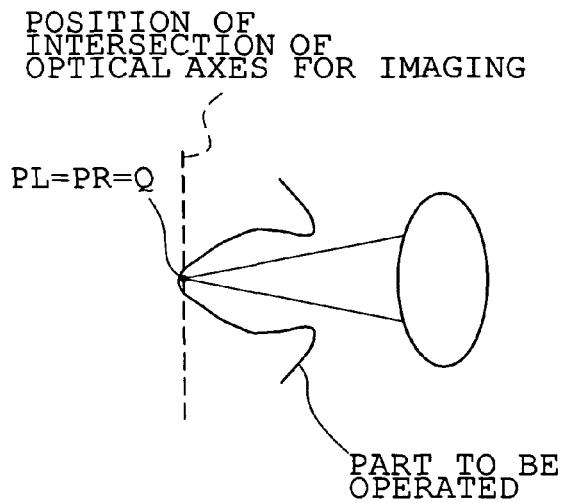
FIGS. 36A, 36B, 36C, and 36D are explanatory views showing the focal positions of the imaging optical systems for left and right eyes in the imaging section of the stereo observation system and the positional relationships between the intersection of the optical axes of the imaging optical systems and the observation object and between the observation object reproduced in an image display section and the display panel.
Figure 36B:
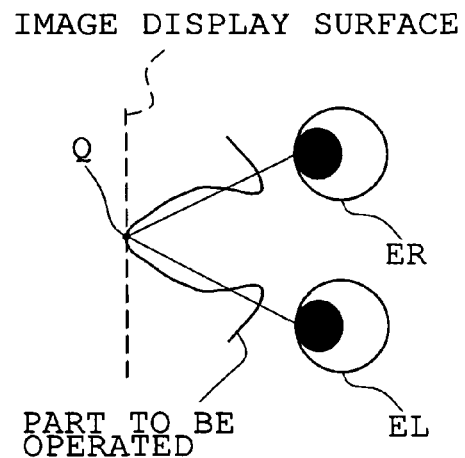
Figure 36C:
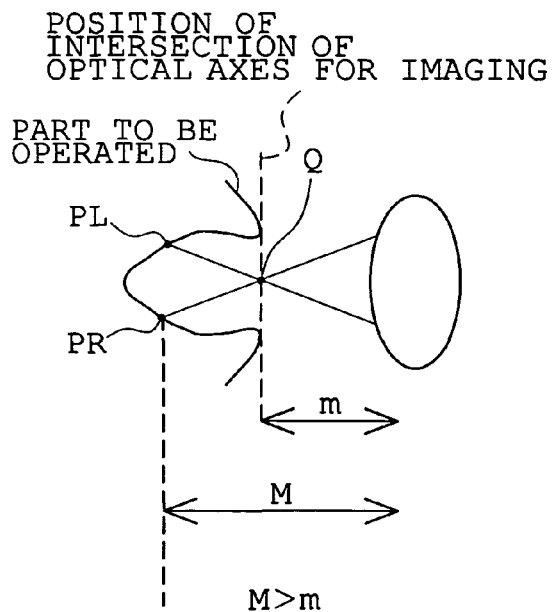
Figure 36D:
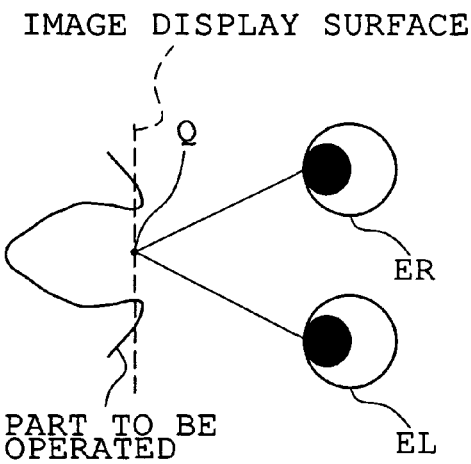
Figure 37:
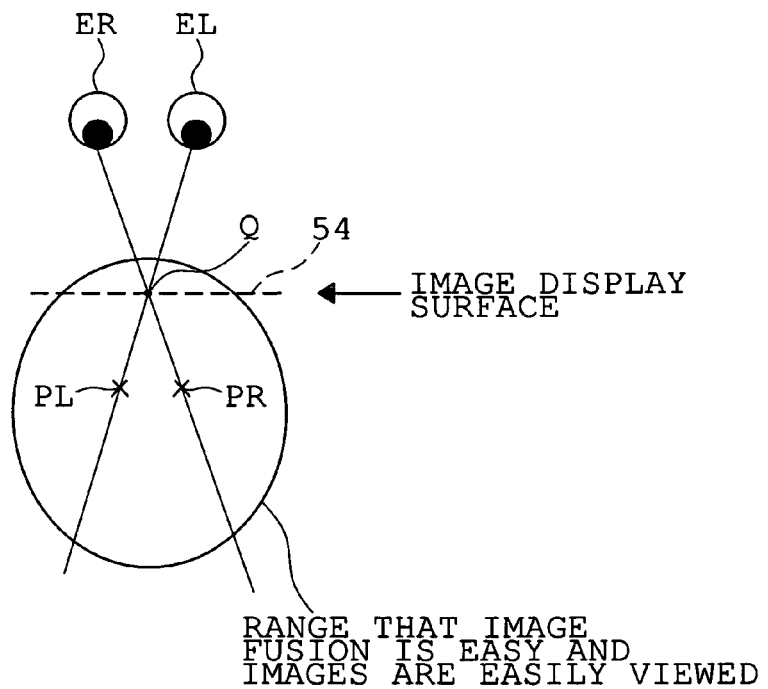
FIG. 37 is an explanatory view showing the positional relationship between the focal position of an image reproduced on the display panel in the same structure as in FIG. 36C and the range in which image fusion is easy and images are easily viewed.

FIGS. 36A-36D are explanatory diagrams for showing the positional relationship, in imaging sections, among focal positions of imaging optical systems for left and right eyes, an intersection of the optical axes of the imaging optical systems, and an observation object, and the positional relationship between an image of the observation object as reproduced in an image display section and a display panel. FIG. 36A shows the positional relationship, in an imaging section of a conventional stereo observation apparatus, among focal positions of imaging optical systems for left and right eyes, an intersection of optical axes of the imaging optical systems, and an observation object. FIG. 36B shows the positional relationship between an image of the observation object of FIG. 36A as reproduced and a display panel. FIG. 36C shows the positional relationship where the focal positions of the imaging optical systems for left and right eyes and the intersection of the optical axes of the imaging optical systems are shifted from one another. FIG. 36D shows the positional relationship between an image of the observation object as produced in the imaging section of FIG. 26C and reproduced and the display panel. In FIG. 36C, the symbol m represents a distance from the principal point of an objective lens located at the most observation-object-side position in the imaging optical systems for left and right eyes to the intersection Q of the optical axes of the imaging optical systems for left and right eyes and M represents a distance (a focal length) from the principal point of the objective lens to individual focal points of the imaging optical systems for left and right eyes. FIG. 37 shows the positional relationship between in-focus positions of images reproduced on the image display surface 54 of the display panel in the same structure as in FIG. 36C and a region in which image fusion is easy and images are easily viewed.

As illustrated in FIGS. 36C and 36D, when the focal points PL and PR of the imaging optical systems for left and right eyes are shifted toward the observation object side of the intersection Q of the optical axes of the imaging optical systems (in other words, the positional relationship is set to be M>m), focused parts in the observation object are always reproduced on a far side of the display surface of the display panel. Hence, as shown in FIG. 37, the stereo observation system can be optimized to take advantage of the range in which image fusion is easy and images are easily viewed, with respect to the display panel.

Figure 38A:
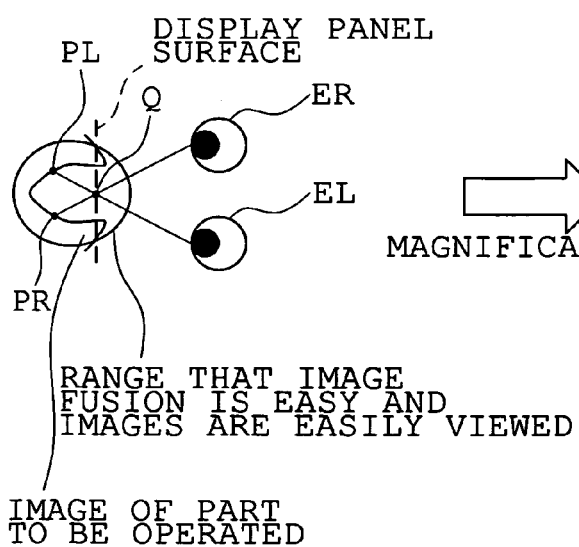
FIGS. 38A and 38B are explanatory views showing changes of the positional relationship between the focal position of an image reproduced on the display panel, before the magnification change (at a low magnification) and after the magnification change (at a high magnification), respectively, in the structure of FIG. 36C.
Figure 38B:
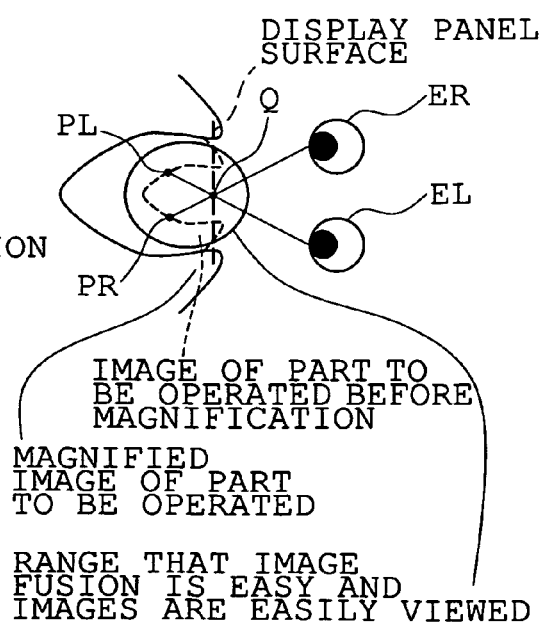

However, as shown in FIG. 36C, when an arrangement is made so that the focal positions PL and PR of the imaging optical systems for left and right eyes are shifted toward the observation object side of the intersection Q of the optical axes of the two imaging optical systems, the magnification change is brought about through the imaging optical systems for left and right eyes with respect to the focal points PL and PR of the imaging optical systems for left and right eyes. Here, consider the case where the system is changed from the low magnification to the high magnification. In the display section, as shown in FIG. 38A, the focal positions PL and PR of the two imaging optical systems on the observation object side are not changed and images projected on the display panel surface are magnified so that the images of the observation object are, reproduced outside the range in which image fusion is easy and images are easily viewed. Consequently, the amount of parallax between the image for the left eye and the image for the right eye on the display panel surface is increased and the image fusion limit is exceeded, with the problem of causing considerable fatigue to the viewer.

Thus, the applicant of the present invention has considered the medical stereo observation system of the present invention so that in order to effectively utilize the image fusible range in the case where a narrow hole-like domain is observed, even when the focal positions of the left and right imaging optical systems are shifted toward the observation object side of the intersection of the optical axes of the imaging optical systems and the magnification change is carried out, the viewer can easily make the stereo observation without feeling fatigue.

Specifically, the medical stereo observation system of the present invention has the imaging optical system for the left eye and the imaging optical system for the right eye, including objective optical systems, variable magnification optical systems, image-forming optical systems, and image sensors, one for each imaging optical system, required to produce an image that a part to be operated is magnified and the observation can be made stereoscopically. In this case, the intersection of the optical axes of the two imaging optical systems is located on the imaging side of a preset depth position required for the observation in the observation object with a depth and individual focal positions of the two imaging optical systems are located on the object side of the intersection of the optical axes of the two imaging optical systems at the low magnification. In addition, the focal positions of the two imaging optical systems are shifted by a preset amount between the intersection of the optical axes of the two imaging optical systems and the focal positions of the two imaging optical systems at the low magnification in association with the magnification change by the variable magnification optical systems. At the same time, the focal positions are each located at the preset depth position required for the observation in the observation object with a depth.

By doing so, the focal positions of the left and right imaging optical systems are shifted toward the observation object side of the intersection of the optical axes of the imaging optical systems, and thus when a narrow hole-like domain is observed, the image fusible range can be effectively utilized. Furthermore, even when the magnification change is carried out, the focal positions of the two imaging optical systems are shifted by a preset amount between the intersection of the optical axes of the two imaging optical systems and the focal positions of the two imaging optical systems at the low magnification in association with the magnification change by the variable magnification optical systems so that the focal positions are each located at the preset depth position required for the observation in the observation object with a depth. As such, even though images projected on the display panel surface are magnified, the image of the observation object can be reproduced in the range in which image fusion is easy and images are easily viewed, and the amount of parallax between the image for the left eye and the image for the right eye can be suppressed so that the image fusion limit is not exceeded.

According to the medical stereo observation system of the present invention, the image fusible range can be effectively utilized and even when the magnification change is made, the viewer can easily perform the stereo observation without feeling fatigue.

In accordance with the embodiments, the structure, function, and effect of the present invention, mentioned above, will be described in detail below.

First Embodiment

Figure 10:
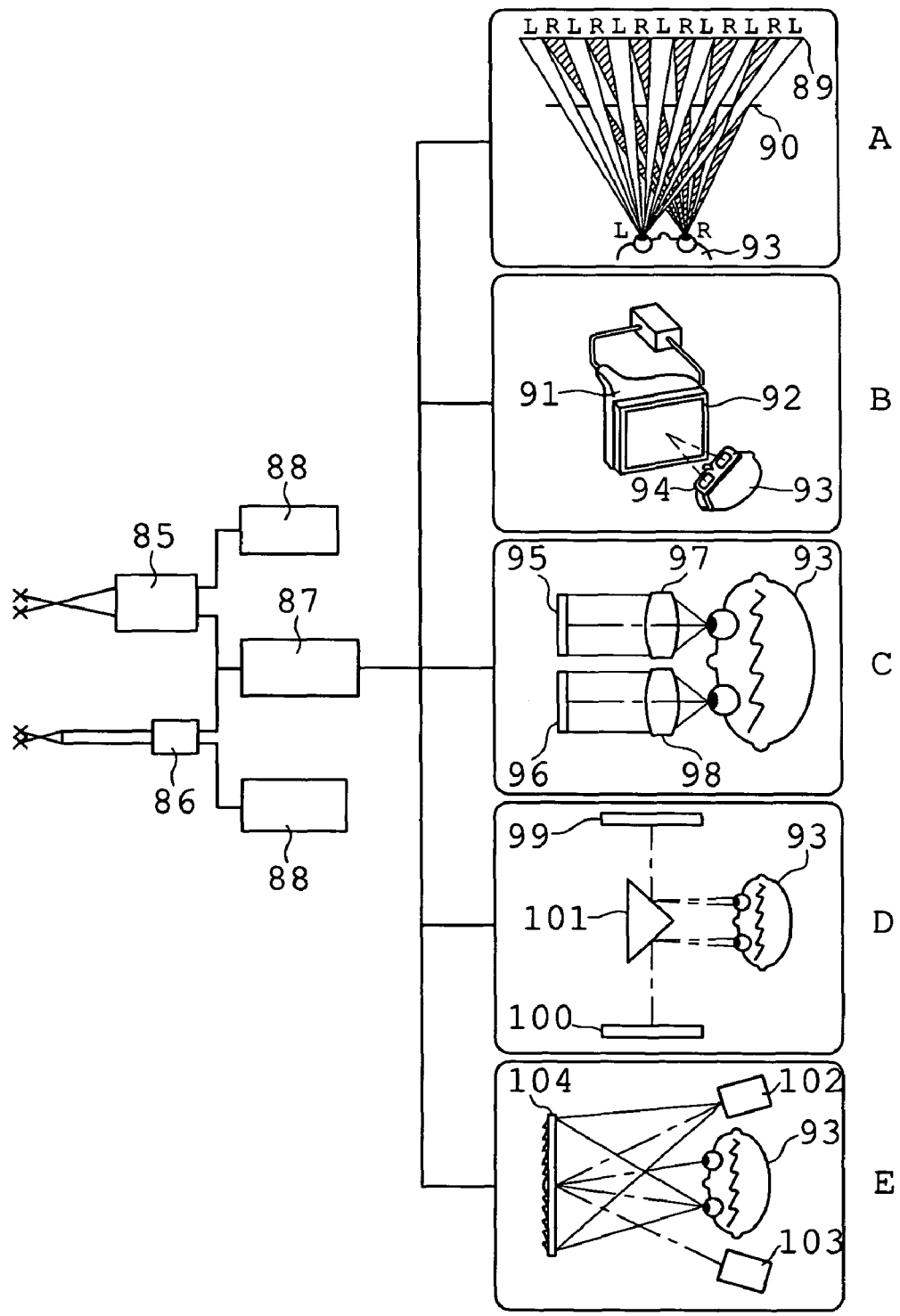
FIG. 10 is a block diagram showing the structure of a first embodiment of the stereo observation system according to the present invention.

FIG. 10 shows a medical stereo observation system according to this embodiment.

The stereo observation system of the first embodiment includes stereo imaging units such as an electronic image surgical microscope 85 and an electronic image stereoendoscope 86; an image signal processing unit 87; light source units 88 supplying illumination light to the stereo imaging units; and one of various stereo display units denoted by symbols A-E in the figure.

The display unit denoted by symbol A in the figure indicates a parallax barrier system no-spectacles stereo display device. Left and right images are arranged in a strip-like array on an LCD 89 and a barrier 90 is placed before the images to introduce selectively corresponding images into the left and right eyes of a viewer 93 so that the stereo observation can be made.

The display unit by B indicates a polarizing spectacles type stereo display device. A polarizing shutter 92 converting in turn a polarizing direction is placed in front of a CRT 91 and the viewer 93 wears polarizing spectacles 94 to thereby introduce the left and right images into the corresponding left and right eyes so that the stereo observation can be made.

The display unit by C indicates a virtual image observation type stereo display device. Left and right eyepiece optical systems 97 and 98 are arranged before left and right small-sized LCDs 95 and 96, respectively, so that the viewer 93 observes virtual images produced by the eyepiece optical systems and thereby the stereo observation can be made.

The display unit by D indicates a direct observation type stereo display device. Images displayed on left and right LCDs 99 and 100 are introduced into the viewer's eyes by a mirror 101 so that the viewer observes the images displayed on the left and right LCDs directly with the corresponding eyes and thereby the stereo observation can be made.

The display unit by E indicates a projection type stereo display device. From left and right projectors 102 and 103, the left and right images are projected on a screen 104 constructed with a Fresnel concave mirror so that the left and right images are introduced into the corresponding eyes of the viewer and thereby the stereo observation can be made.

Figure 11:
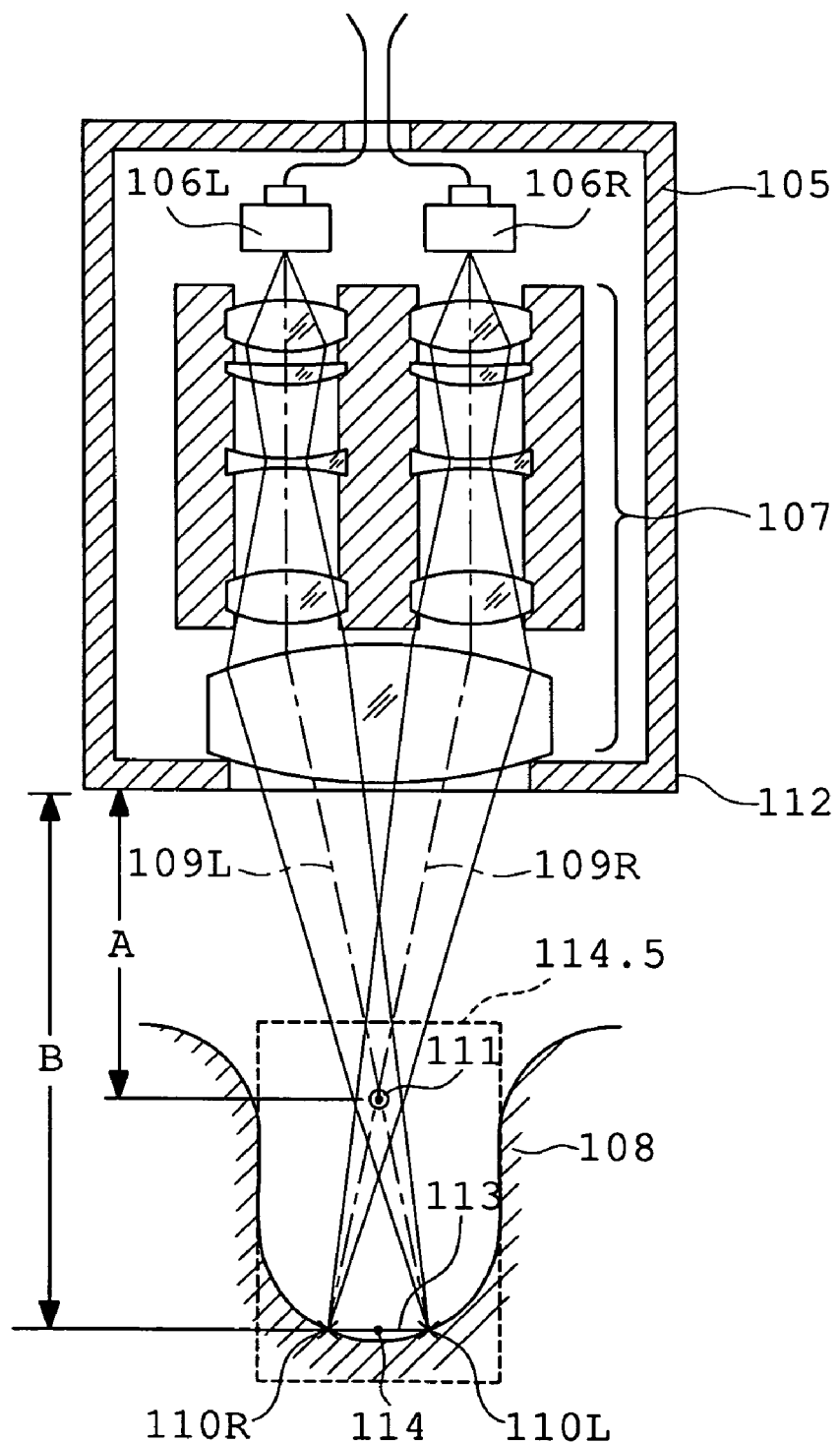
FIG. 11 is a view showing the structure of the optical system of an electronic image surgical microscope used in the first embodiment of the present invention.

In FIG. 11, the structure of the optical system of the electronic image surgical microscope 85 in FIG. 10 is shown. An electronic image surgical microscope 105 that is a stereo imaging apparatus has left and right CCDs 106L and 106R and an imaging optical system 107 forming images that mutually have parallax on the CCDs with respect to an observation object 108. Object-side focal points 110L and 110R of the imaging optical system are located far away from an intersection 111 of left and right optical axes 109L and 109R of the imaging optical system, viewed from the scope section of the electronic image surgical microscope 105. Specifically, when a distance from a lower surface 112 of the scope section of the electronic image surgical microscope to the intersection 111 of the left and right optical axes of the imaging optical system is represented by A and a distance from the lower surface 112 of the scope section to a middle point 114 of a straight line 113 connecting the left and right object-side focal points 110L and 110R of the imaging optical system is represented by B, the imaging optical system is constructed to have the relation of A<B.

According to this construction, a comfort observable range 114.5 in real space can be widely provided on the front side (namely, on the electronic image surgical microscope side) of the object-side focal points 110L and 110R of the electronic image surgical microscope.

Figure 12:
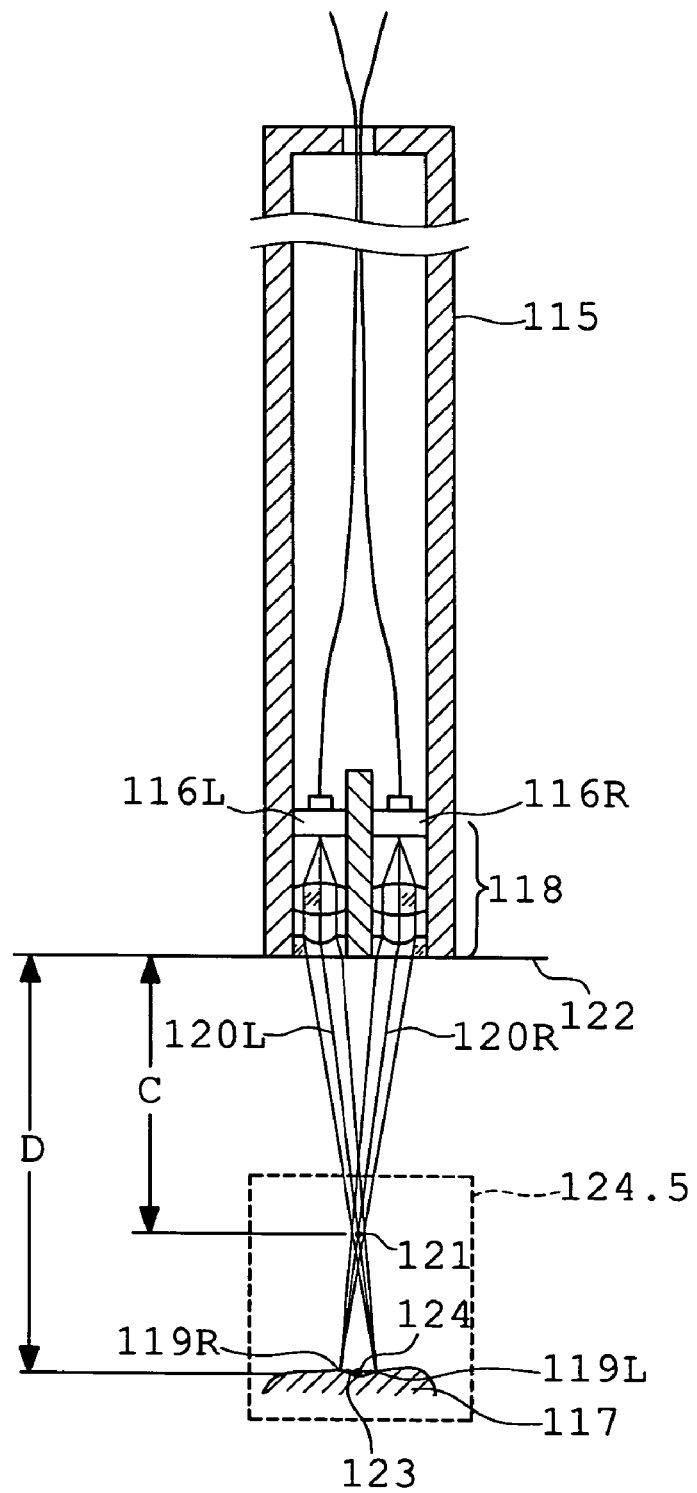
FIG. 12 is a view showing the structure of the optical system of an electronic image stereoendoscope used in the first embodiment of the present invention.

In FIG. 12, the structure of the electronic image stereoendoscope 86 of FIG. 10 is shown. An electronic image stereoendoscope 115 that is the stereo imaging apparatus has left and right CCDs 116L and 116R and an imaging optical system 118 forming images that mutually have parallax on the CCDs with respect to an observation object 117. Object-side focal points 119L and 119R of the imaging optical system are located far away from an intersection 121 of left and right optical axes 120L and 120R of the imaging optical system, viewed from the scope section of the electronic image stereoendoscope 115. Specifically, when a distance from a lower surface 122 of the electronic image stereoendoscope to the intersection 121 of the left and right optical axes of the imaging optical system is represented by C and a distance from the lower surface 122 of the electronic image stereoendoscope to a middle point 124 of a straight line 123 connecting the left and right object-side focal points 119L and 119R of the imaging optical system is represented by D, the imaging optical system is constructed to have the relation of C<D. According to this construction, a comfort observable range 124.5 in real space can be widely provided on the front side (namely, on the electronic image stereoendoscope side) of the object-side focal points 119L and 119R of the electronic image stereoendoscope.

According to the stereo observation system including a combination of the stereo imaging apparatuses with the stereo display device, constructed as mentioned above, even when the viewer observes an observation object provided with space in a depth direction, required for the viewer, such as that shown in each of the devices A and B of FIG. 10, the viewer adjusts focal points of a stereo imaging apparatus to deep parts of an observation object, and thereby the observation object can be widely covered within a comfort observable range in real space according to the stereo imaging apparatus. As a result, an observation object reproduced by a display device is widely covered within a comfort observable range by the display device and the viewer can thus observe the observation object reproduced, without strongly feeling fatigue caused by a positional shift between the adjusting distance and the vergence distance.

Second Embodiment

Figure 13:
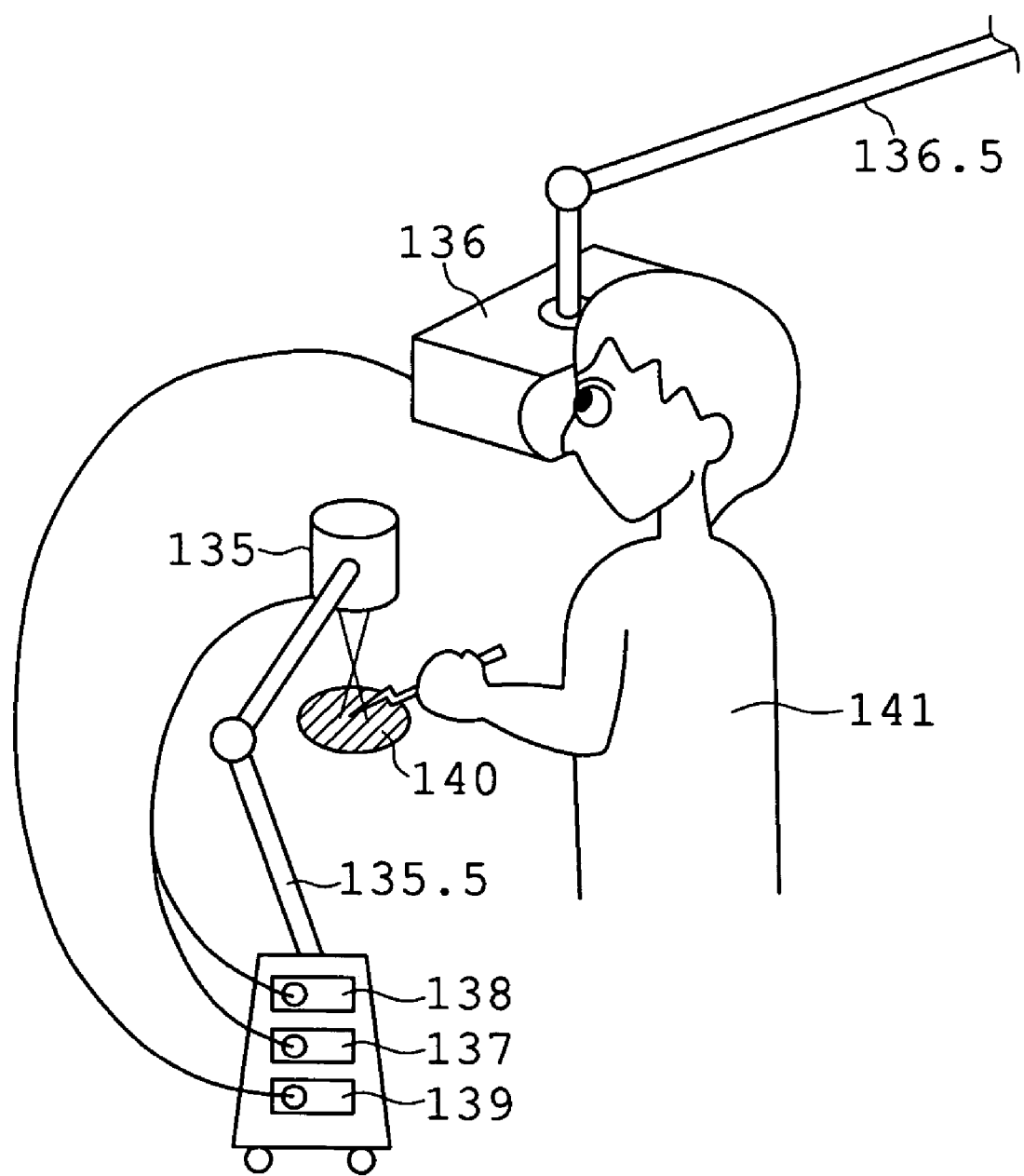
FIG. 13 is a view showing the structure of a second embodiment of the stereo observation system according to the present invention.

FIG. 13 shows a medical stereo observation system according to this embodiment.

The stereo observation system of the second embodiment comprises an electronic image surgical microscope 135 constructed as an imaging unit, a holding arm 135.5 holding the electronic image surgical microscope, a virtual image observation type stereo display unit 136, a holding arm 136.5 holding the stereo display unit, a light source unit 137 providing the electronic image surgical microscope with illumination light, an image signal processing unit 138 processing an image signal produced by the electronic image surgical microscope, and an image signal supplying unit 139 supplying the image signal to the stereo display unit. Images of a part 140 to be operated that mutually have parallax are produced by the electronic image surgical microscope 135 and are displayed on the stereo display unit 136 through the image signal processing unit 138 and the image signal supplying unit 139. A viewer 141 observes the images displayed on the stereo display unit and thereby the stereo observation of the part to be operated is carried out.

Figure 14:
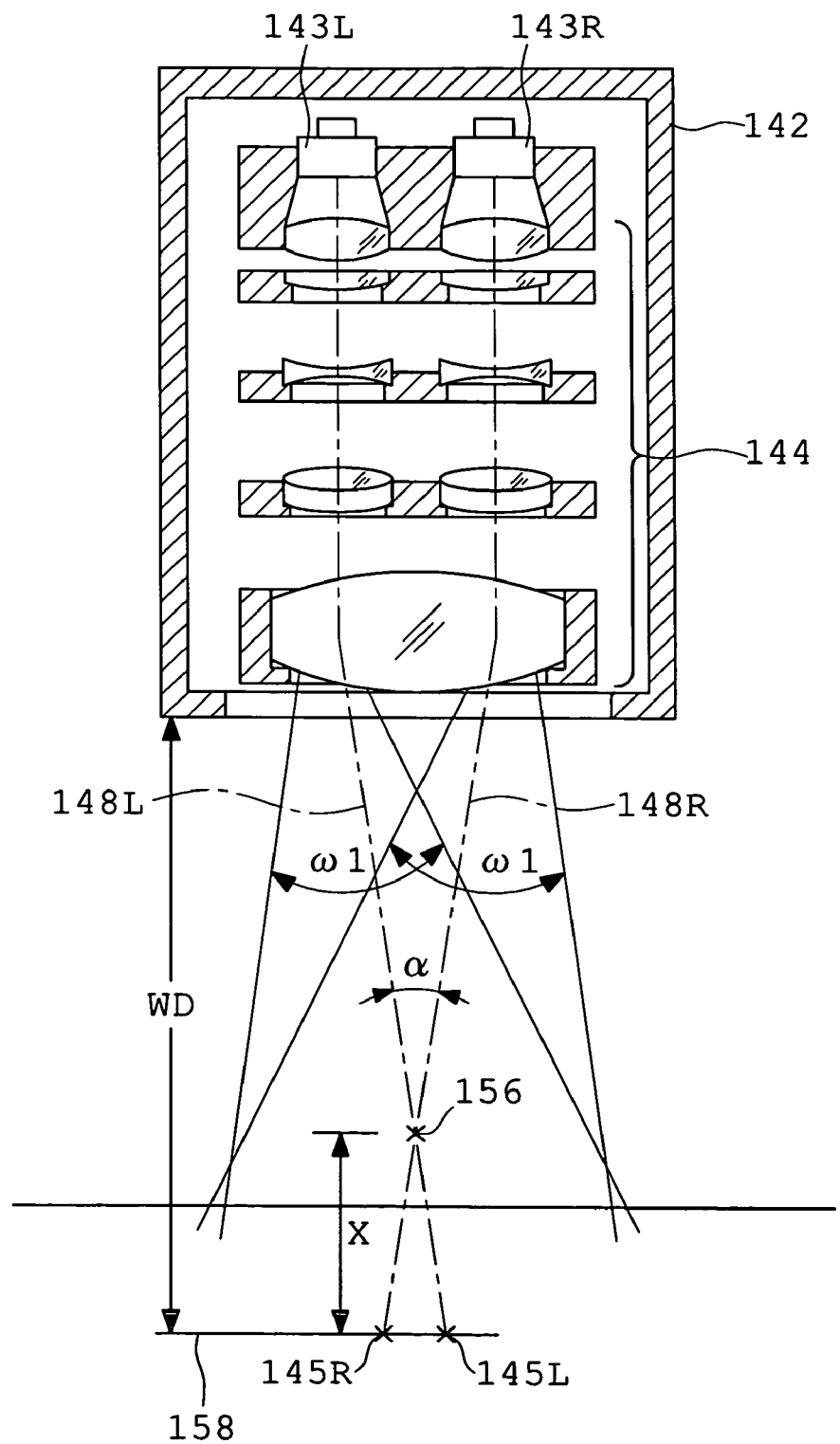
FIG. 14 is a view showing the structure of the optical system of an electronic image surgical microscope used in the second embodiment of the present invention.

FIG. 14 shows the structure of the optical system of the electronic image surgical microscope. In this figure, reference numeral 142 denotes a scope section of the electronic image surgical microscope, 143L and 143R denote CCDs, 144 denotes an imaging optical system, 145R denotes a focal position of the right-eye optical path of the imaging optical system, 145L denotes a focal position of the left-eye optical path of the imaging optical system, 148R denotes an optical axis of the right-eye optical path of the imaging optical system, 148L denotes an optical axis of the left-eye optical path of the imaging optical system, and 156 denotes an intersection of the optical axes of the right-eye and left-eye optical paths. Also, in the figure, symbol WD represents a working distance, indicating a distance from the most object-side surface of the scope section 142 of the electronic image surgical microscope to the focal positions 145L and 145R of the imaging optical system. Symbol a represents an internal inclination angle, indicating an angle made by the optical axis 148R of the right-eye optical path of the imaging optical system with the optical axis 148L of the left-eye optical path. Symbol $\omega_1$ represents an individual diagonal field angle of the imaging optical system. Symbol x represents the amount of shift of the focal positions, indicating a distance from the intersection 156 of the optical axes of the imaging optical system to the focal points of the imaging optical system.

In the electronic image surgical microscope of the second embodiment, individual parameters mentioned above are set as described below.

$WD=250$ mm, $\alpha=4°$, $\omega_1=20°$, and $x=40$ mm

Figure 15:
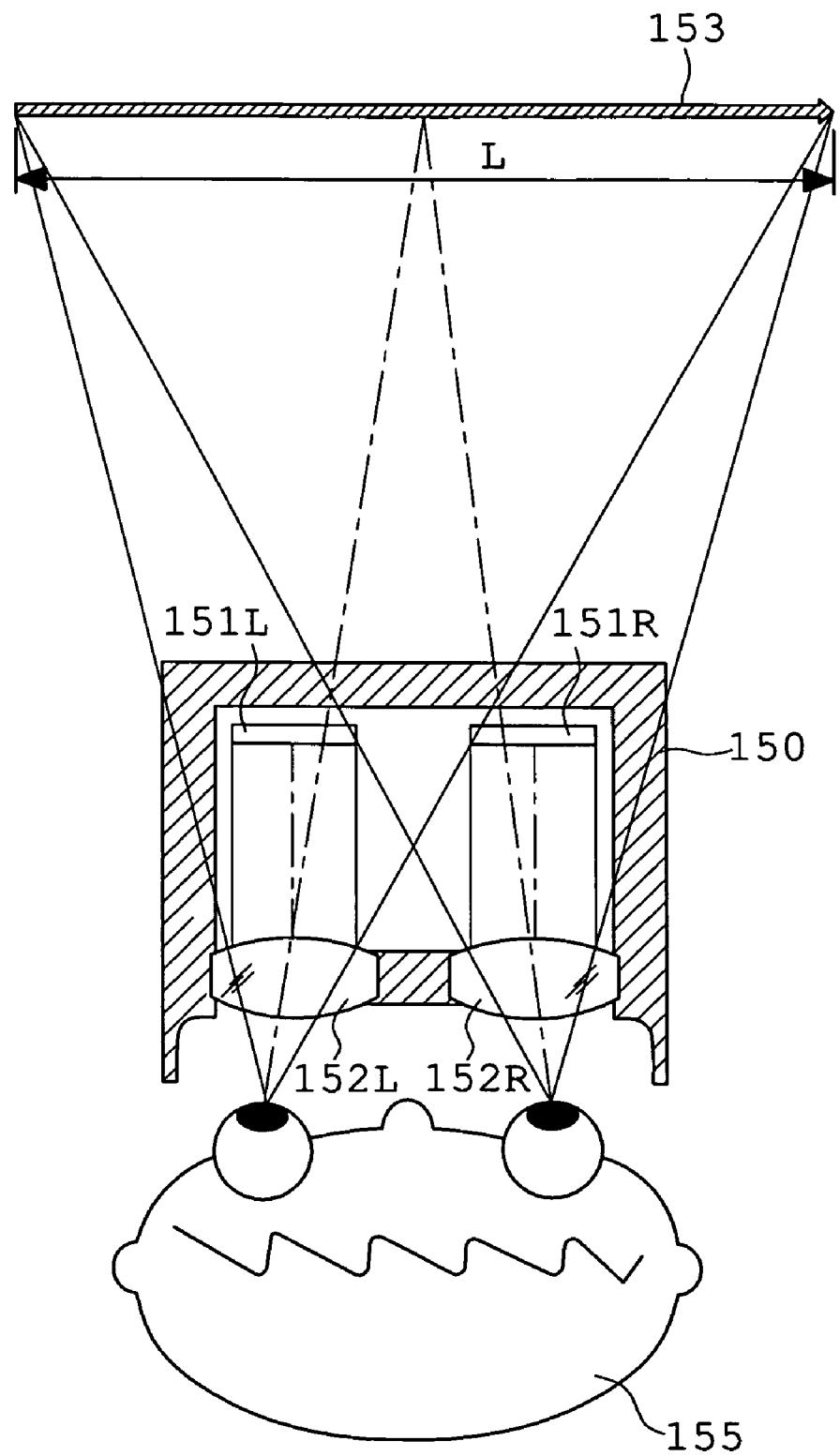
FIG. 15 is a view showing the structure of the optical system of a stereo display device used in the second embodiment of the present invention.

FIG. 15 shows the structure of the optical system of the stereo display device.

In this figure, reference numeral 150 represents a scope section of the stereo display device, 151L and 151R represent LCDs, 152L and 152R represent eyepiece optical systems, 153 represents a virtual image where images displayed on the LCDs by the eyepiece optical systems are projected, and symbol L represents a diagonal distance of an image observed by a viewer 155. In the display device of the second embodiment, the above parameter is set as described below.

$L=508$ mm

Substitution of the parameters of the electronic image surgical microscope and the stereo display device mentioned above in Condition (1) of the present invention gives 13.85 mm$\leq x \leq$44.3 mm.

Figure 16:
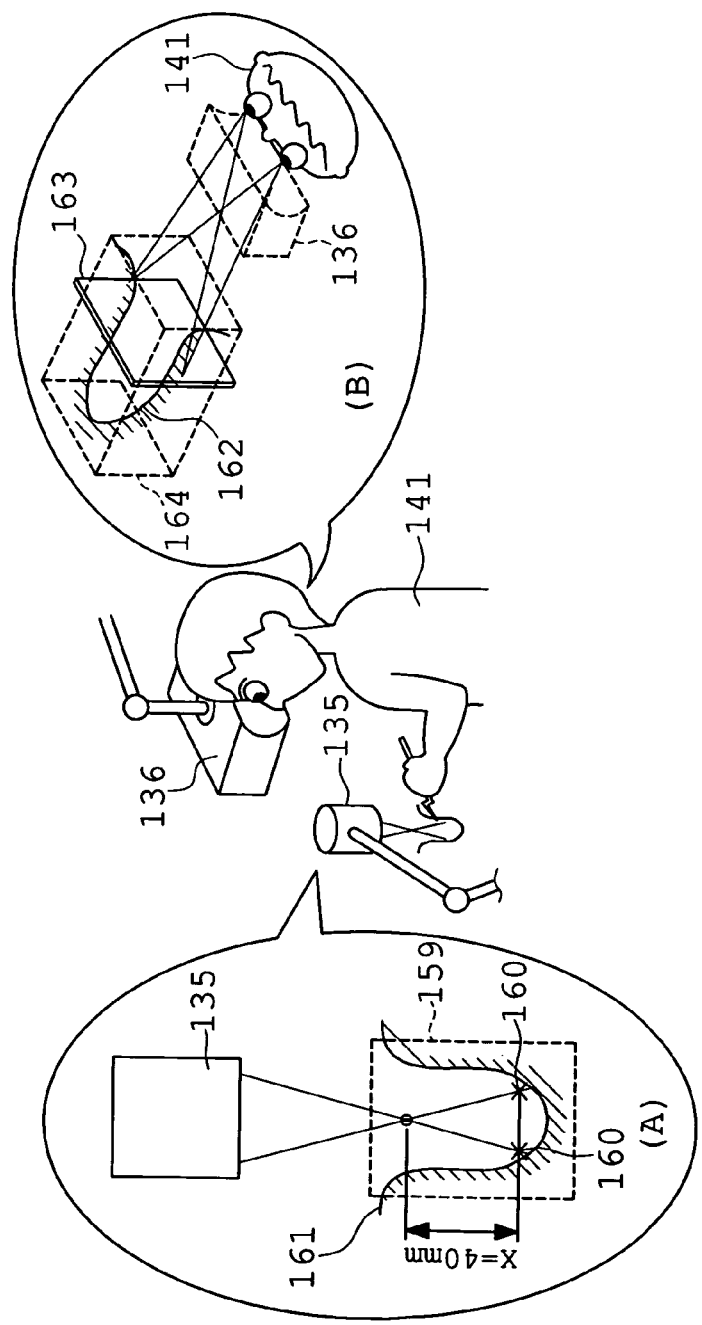
FIG. 16 is a view showing the effect of the second embodiment of the present invention.

The value of the amount of shift x in the second embodiment is 40 mm, which satisfies the above condition. The second embodiment satisfying the condition, as shown in (A) of FIG. 16, is capable of widely ensuring a comfort observable range 159 in real space of the electrical image surgical microscope 135 on the front side (namely, on the electronic image surgical microscope side) of focal points 160 of the electronic image surgical microscope. Thus, when the viewer 141 uses the electronic image surgical microscope to observe an observation object 161 provided with space in the depth direction, the observation object 161 is widely covered by the comfort observable range 159 in real space of the electrical image surgical microscope. Consequently, as shown in (B) of FIG. 16, an observation object 162 reproduced around a virtual position 163 by the stereo display device 136 is widely covered within a comfort observable range 164 produced by the display device, likewise around the virtual position 163. The viewer can thus observe the observation object reproduced, without strongly feeling fatigue caused by a positional shift between adjustment and vergence.

Third Embodiment

Figure 17:
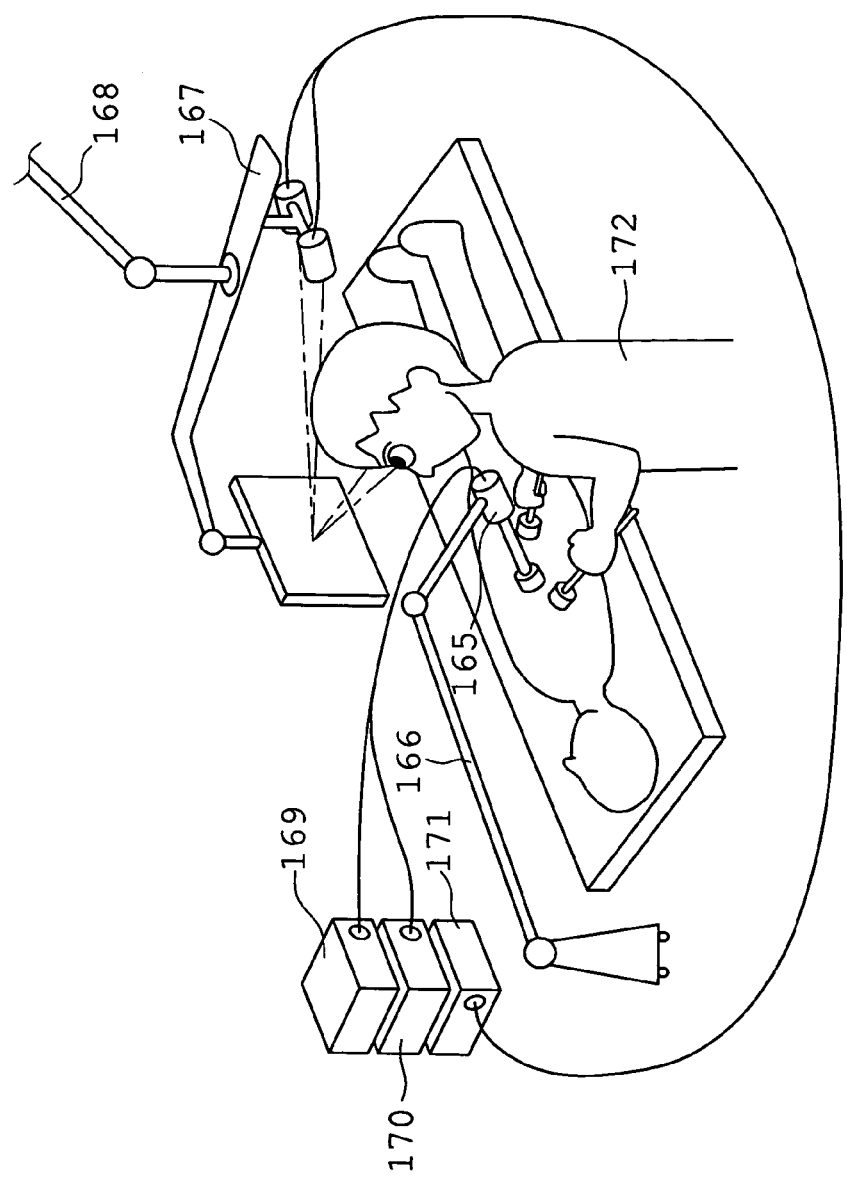
FIG. 17 is a view showing the structure of a third embodiment of the stereo observation system according to the present invention.

FIG. 17 shows the medical stereo observation system of this embodiment. The stereo observation system of the third embodiment comprises an electronic image stereoendoscope 165 constructed as an imaging unit, a holding arm 166 holding the electronic image stereoendoscope, a projection type stereo display unit 167, a holding arm 168 holding the stereo display unit, a light source unit 169 providing the electronic image stereoendoscope with illumination light, an image signal processing unit 170 processing an image signal produced by the electronic image stereoendoscope, and an image signal supplying unit 171 supplying an image signal to the stereo display unit. The electronic image stereoendoscope 165 produces images of a part to be operated that mutually have parallax, and the images are displayed on the stereo display unit 167 through the image signal processing unit 170 and the image signal supplying unit 171. A viewer 172 observes the images displayed on the stereo display unit, and thereby the stereo observation of the part to be operated is carried out.

Figure 18:
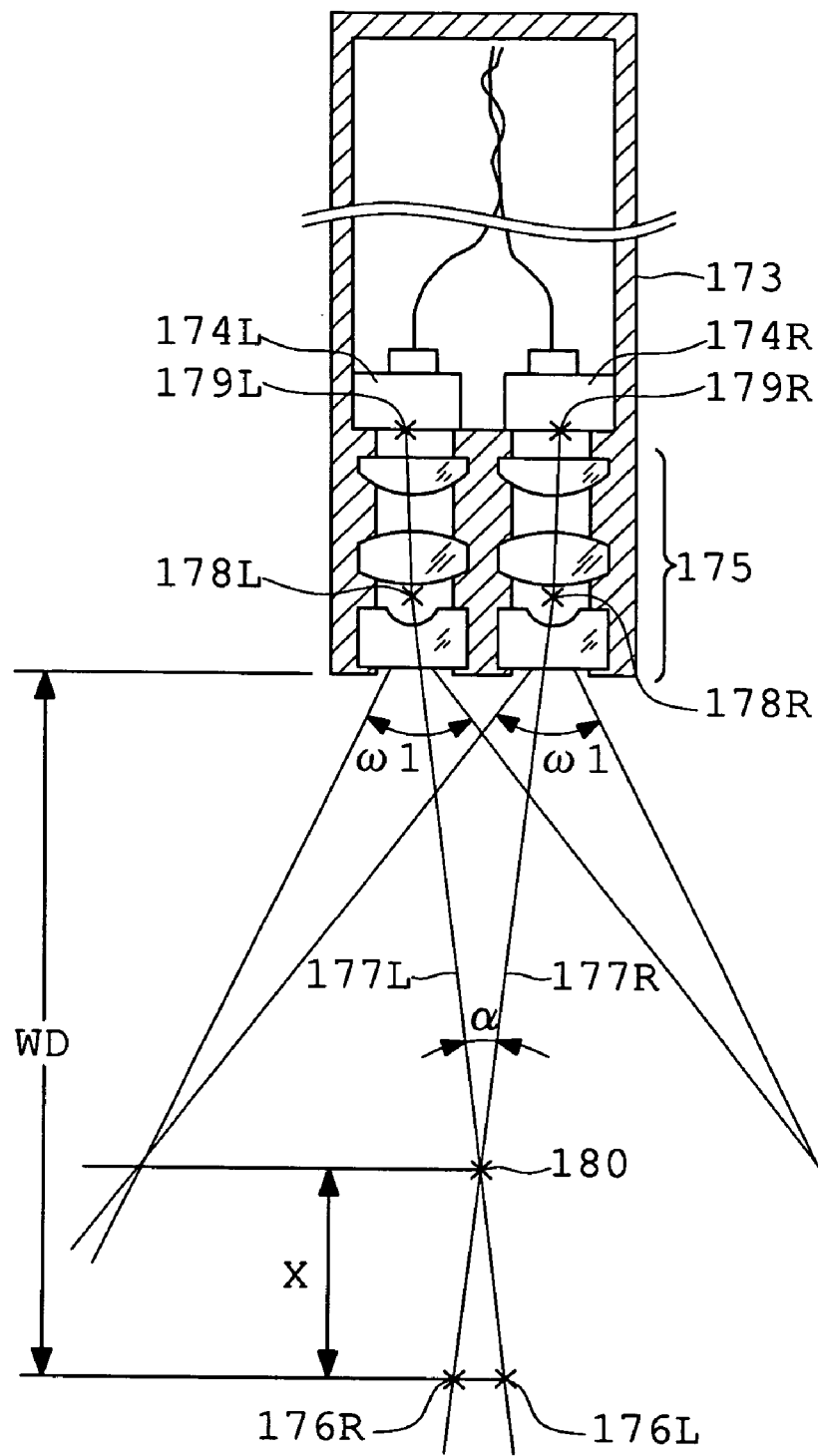
FIG. 18 is a view showing the structure of the optical system of the electronic image stereoendoscope used in the third embodiment of the present invention.

FIG. 18 shows the structure of the optical system of the electronic image stereoendoscope. In this figure, reference numeral 173 denotes a scope section of the electronic image stereoendoscope, 174L and 174R denote CCDs, 175 denotes an imaging optical system, 176R denotes a focal point of the right-eye optical path of the imaging optical system, 176L denotes a focal point of the left-eye optical path of the imaging optical system, 177R denotes an optical axis of the right-eye optical path of the imaging optical system (a straight line connecting a center 178R of the entrance pupil of the right-eye optical path with an object-side conjugate point 176R of a center 179R of the imaging area of the CCD), 177L denotes an optical axis of the left-eye optical path of the imaging optical system (a straight line connecting a center 178L of the entrance pupil of the left-eye optical path with an object-side conjugate point 176L of a center 179L of the imaging area of the CCD), and 180 denotes an intersection of the optical axes of the imaging optical system. Also, in the figure, symbol WD represents a working distance, indicating a distance from the most object-side surface of the scope section 173 of the electronic image stereoendoscope to the focal positions 176L and 176R of the imaging optical system. Symbol α represents an internal inclination angle, indicating an angle made by the optical axis 177R of the right-eye optical path of the imaging optical system with the optical axis 177L of the left-eye optical path. Symbol $\omega_1$ represents an individual diagonal field angle of the imaging optical system. Symbol x represents the amount of shift of the focal position, indicating a distance from the intersection 180 of the optical axes of the imaging optical system to the focal points of the imaging optical system. In the electronic image stereoendoscope of the third embodiment, individual parameters mentioned above are set as described below.

WD=50 mm, α=6.9°, $\omega_1$=60°, and x=12 mm

Figure 19:
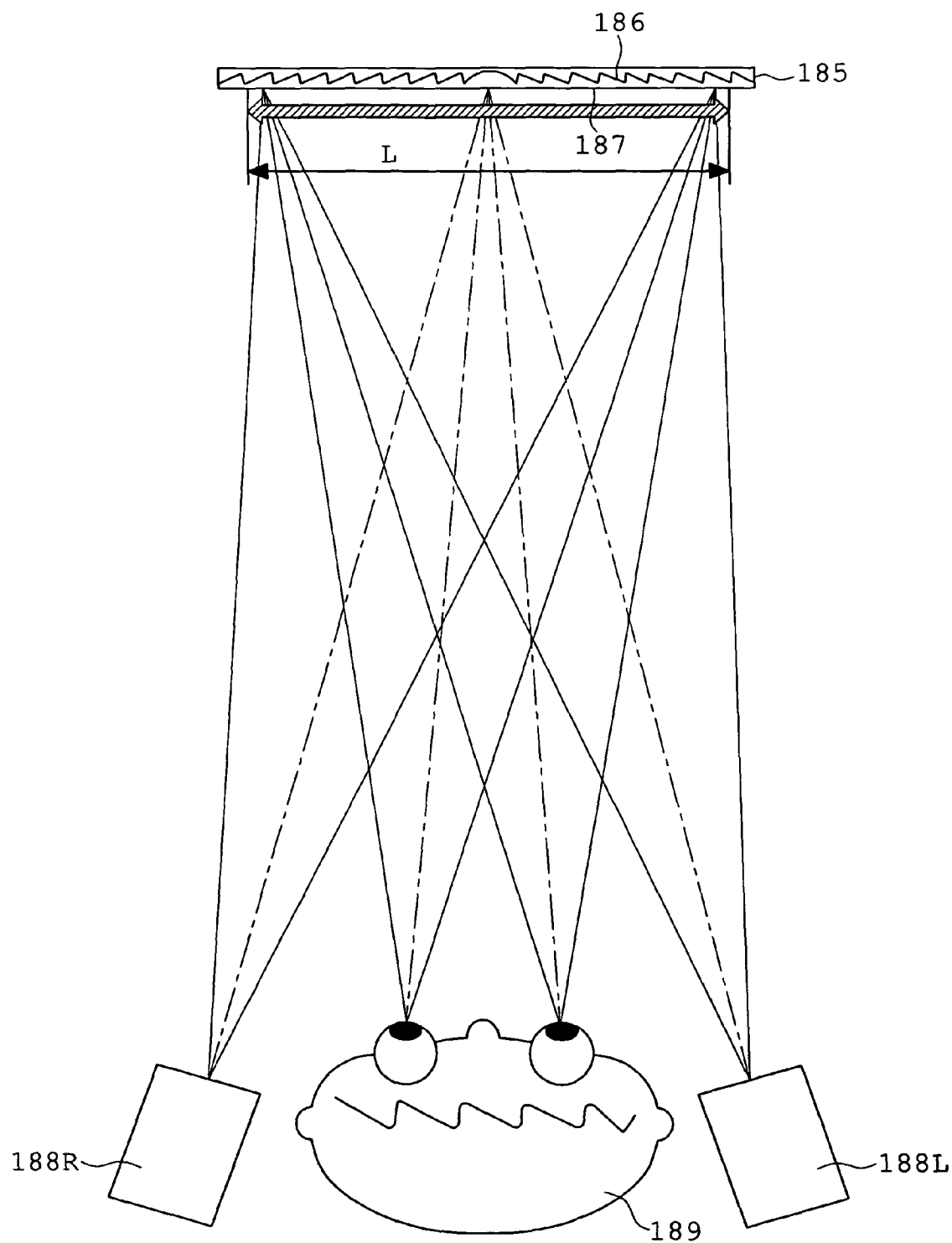
FIG. 19 is a view showing the structure of the optical system of the stereo display device used in the third embodiment of the present invention.

FIG. 19 shows the arrangement of the optical system of the stereo display device.

In this figure, reference numeral 185 represents an image projection screen including a Fresnel concave mirror 186 and a diffuser 187 and numerals 188L and 188R represent projectors projecting left and right images on the image projection screen. An image projected by the right-eye image projector 188R is introduced into the right eye of a viewer 189 by means of the action of the Fresnel concave mirror 186 and is observed with the right eye of the viewer. Similarly, an image projected by the left-eye image projector 188L is observed with the left eye of the viewer. In this way, the viewer can observe the left and right images with the corresponding eyes and the stereo observation can be made. In the figure, symbol L represents a diagonal distance of the observation image observed by the viewer. In the display device of the third embodiment, the above parameter is set as described below.

L=478 mm

Substitution of the parameters of the electronic image stereoendoscope and the stereo display device mentioned above in Condition (1) of the present invention gives 5.28 mm≦x≦15.15 mm. The value of the amount of shift x in the third embodiment is 12 mm, which satisfies the above condition.

Figure 20:
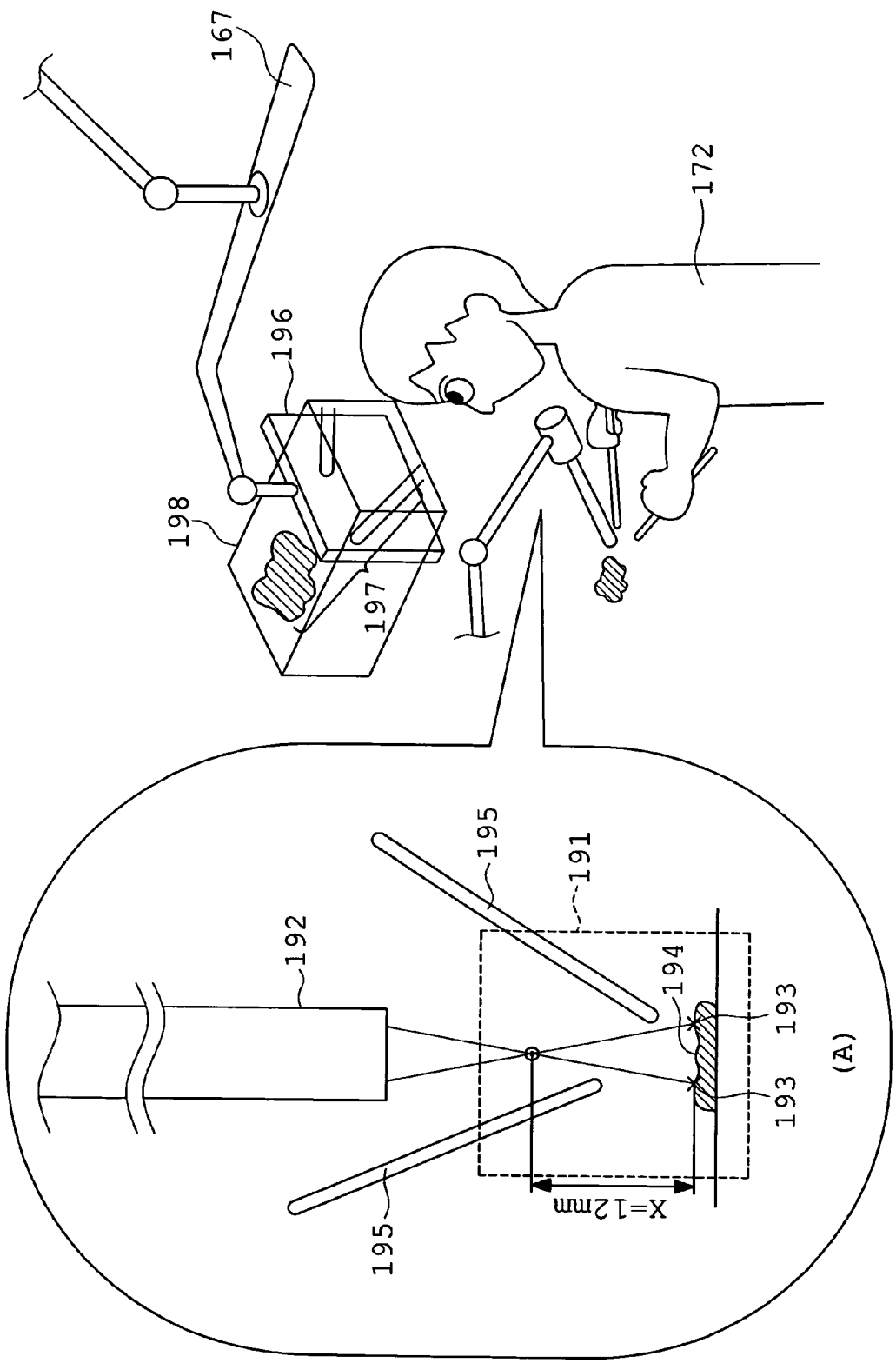
FIG. 20 is a view showing the effect of the third embodiment of the present invention.

The third embodiment satisfying the condition, as shown in (A) of FIG. 20, is capable of widely ensuring a comfort observable range 191 in real space of the electrical image stereoendoscope 192 on the front side (namely, on the electronic image stereoendoscope side) of focal positions 193 of the electronic image stereoendoscope. Thus, when the viewer uses the electronic image stereoendoscope to observe a part 194 to be operated and observation space provided with space in the depth direction, including treatment tools 195, the observation space is widely covered by the comfort observable range 191 in real space of the electrical image stereoendoscope. Consequently, as shown in FIG. 20, an observation space 197 reproduced around an image projection screen 196 by the stereo display device 167 is widely covered within a comfort observable range 198 produced by the display device, likewise around the image projection screen. The viewer can thus observe the observation object reproduced, without strongly feeling fatigue caused by a positional shift between the adjusting distance and the vergence distance.

Fourth Embodiment

Figure 21:
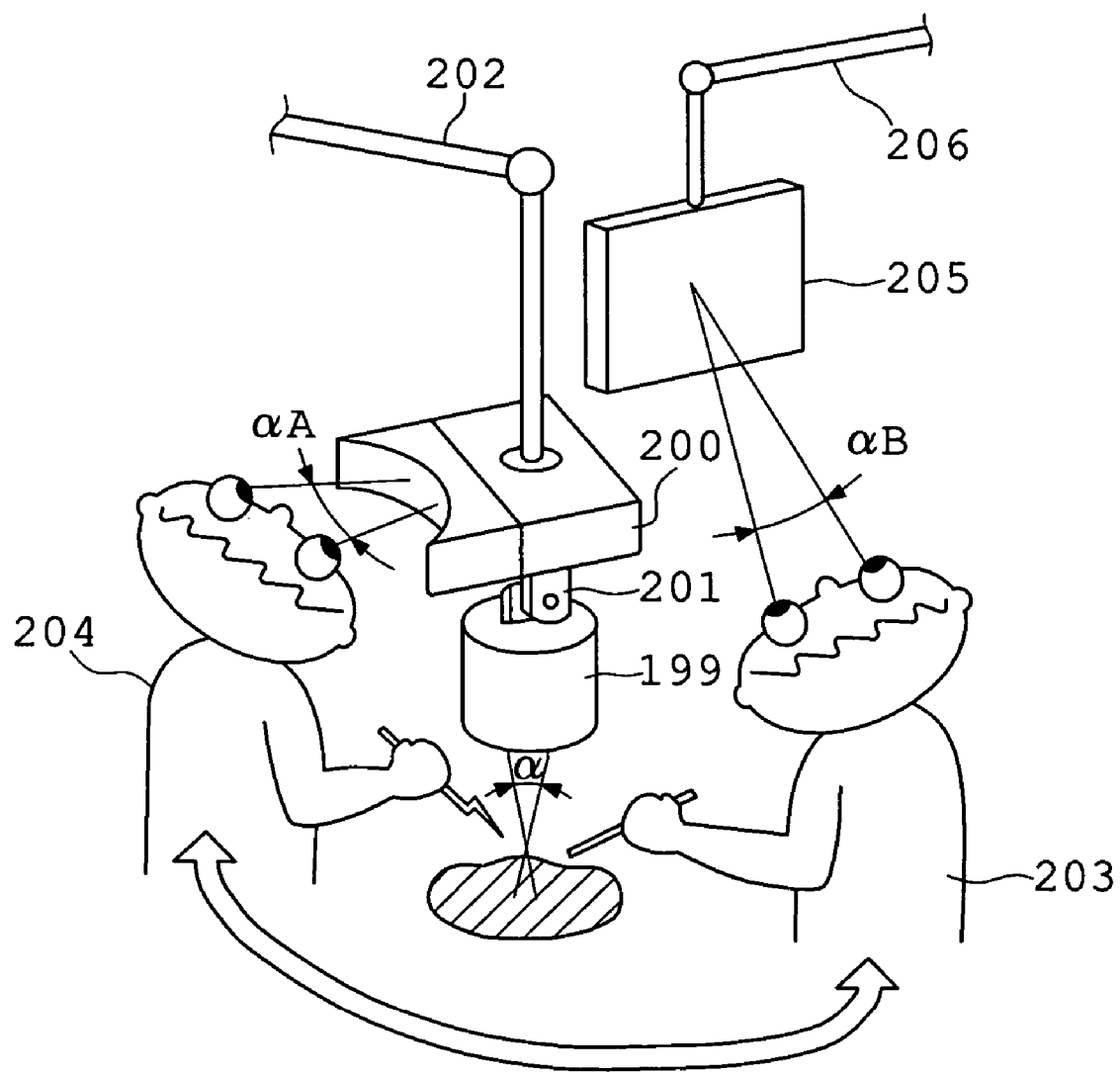
FIG. 21 is a view showing the structure of a fourth embodiment of the stereo observation system according to the present invention.

FIG. 21 shows the medical stereo observation system of this embodiment.

The stereo observation system of the fourth embodiment comprises an electronic image surgical microscope 199 constructed as an imaging unit, a virtual image observation type stereo display device 200 for a first viewer 204, a connection 201 connecting the electronic image surgical microscope with the stereo display device, a holding arm 202 holding the stereo display device, a parallax barrier type no-spectacles stereo display device 205 for a second viewer 203, and a holding arm 206 holding the parallax barrier type no-spectacles stereo display device.

In the figure, reference symbol αA denotes a vergence angle at which the first viewer observes the virtual image observation type stereo display device for the first viewer; αB, a vergence angle at which the second viewer observes the parallax barrier type no-spectacles stereo display device for the second viewer; and α, an internal inclination angle made by the optical axes of the left and right optical paths of the electronic image surgical microscope.

In the medical stereo observation system of the fourth embodiment, the above parameters are set as described below.

αA=3.5°, αB=2°, and α=4°

Consequently, αA/αB=1.75, which satisfies Condition (2) of the present invention.

Condition (2) of the present invention is provided for the purpose of setting the parameters so that even when two display devices of different vergence angles are alternately used, the viewer has no feeling of physical disorder with respect to work.

Consequently, even though a viewer changes places with another in accordance with the progress of the surgical operation, another viewer has no feeling of physical disorder of treatment work relative to the display device and thus can continue the observation and treatment work without the feeling of fatigue.

Fifth Embodiment

Figure 24:
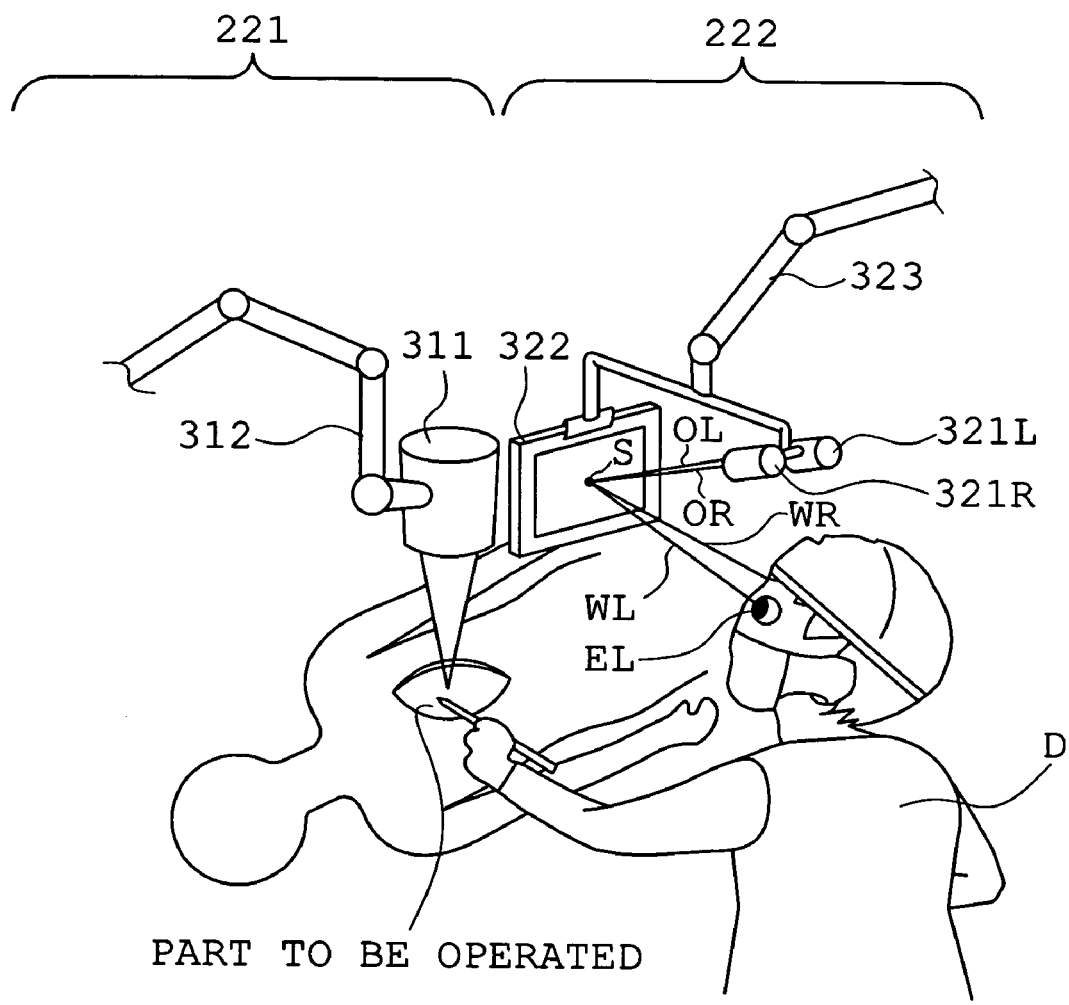
FIG. 24 is an explanatory view showing a fundamental structure common to the medical stereo observation systems of individual embodiments of the present invention.
Figure 25:
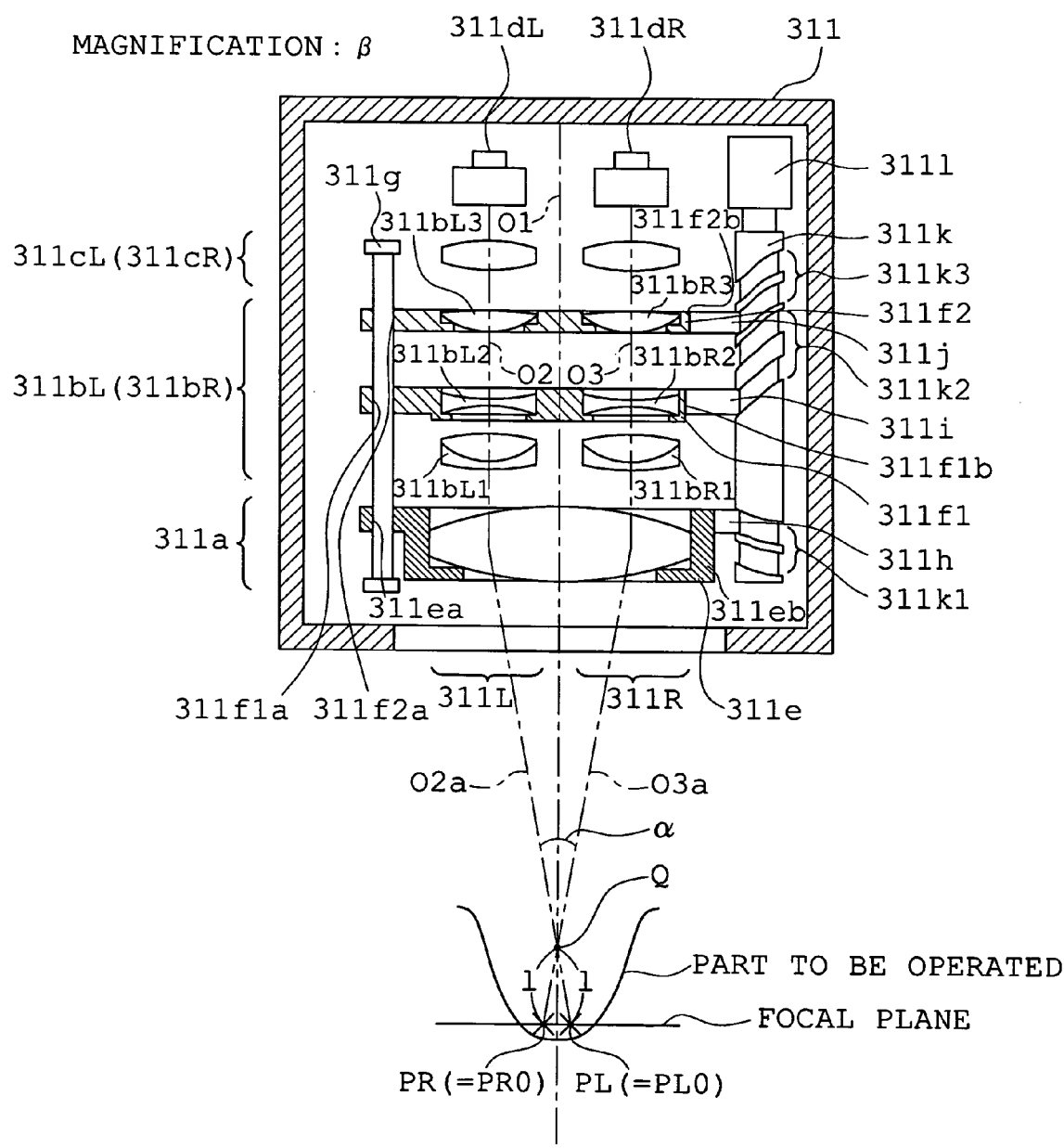
FIG. 25 is an explanatory view showing the optical structure of imaging optical systems for left and right eyes used in the medical stereo observation system of a fifth embodiment, positions of individual optical members at a low magnification, an intersection of optical axes on the observation object side in the imaging optical systems for left and right eyes, and individual focal positions of the imaging optical systems for left and right eyes relative to a focal plane.
Figure 26:
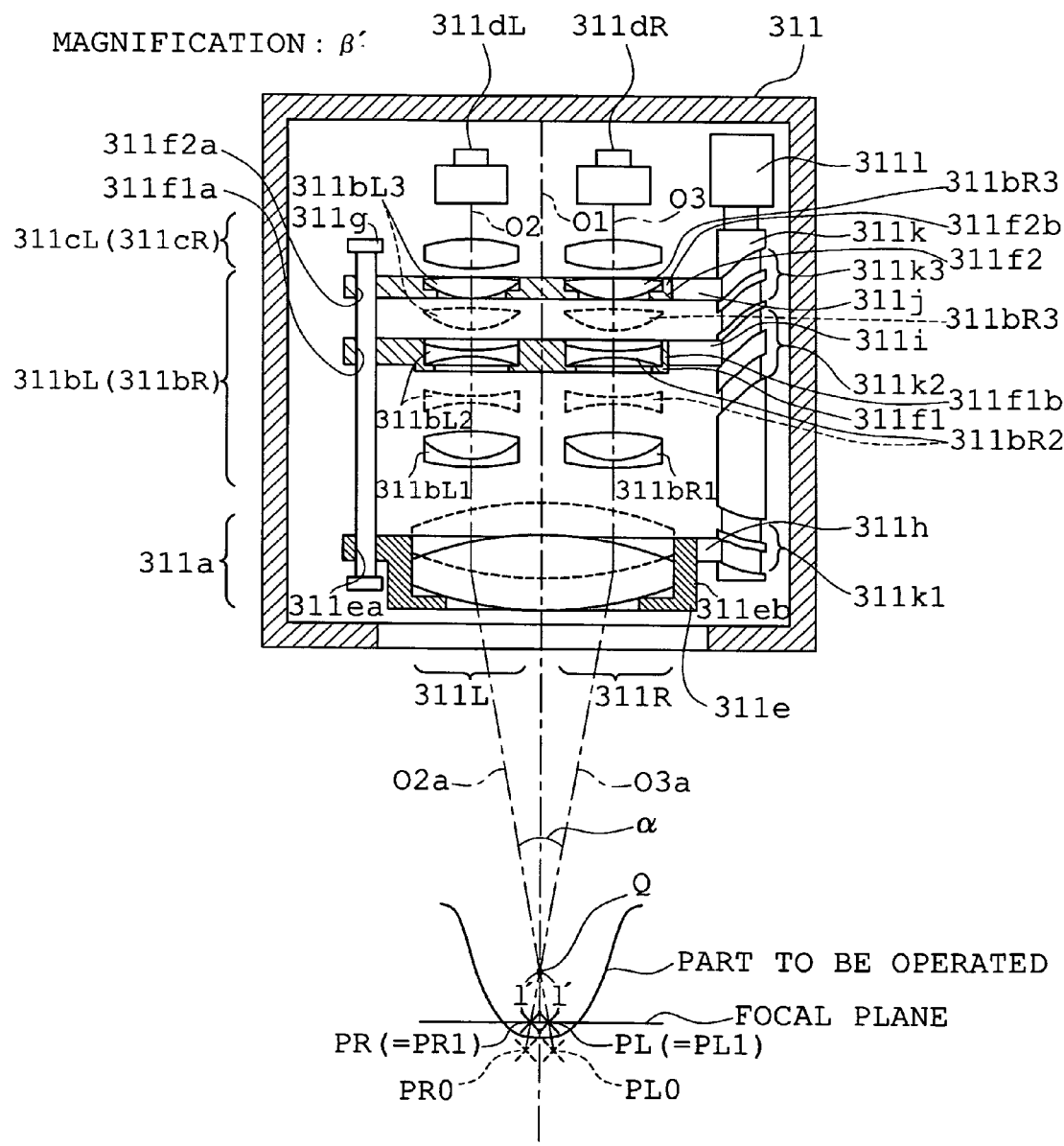
FIG. 26 is an explanatory view showing the optical structure of imaging optical systems for left and right eyes used in the medical stereo observation system of the fifth embodiment, positions of individual optical members at a high magnification, an intersection of optical axes on the observation object side in the imaging optical systems for left and right eyes, and individual focal positions of the imaging optical systems for left and right eyes relative to a focal plane.
Figure 27A:
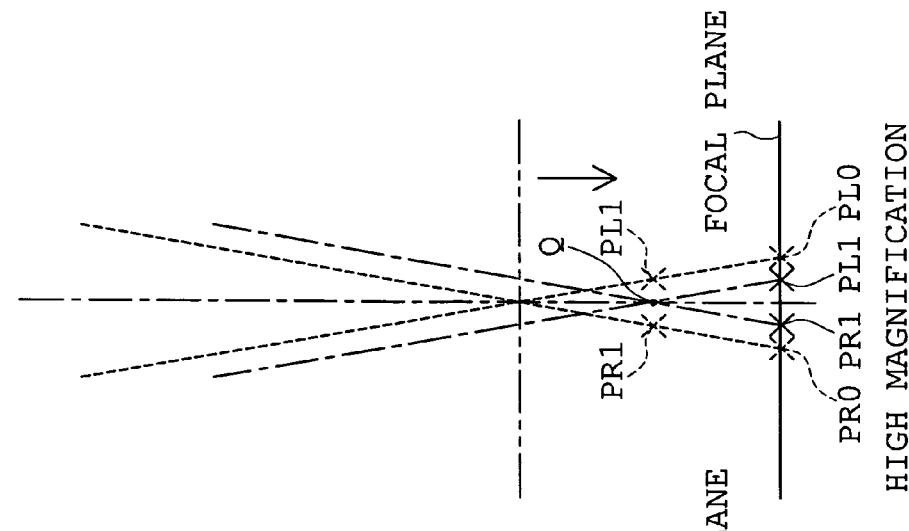
FIGS. 27A, 27B, and 27C are explanatory views, each showing focal points of the imaging optical systems for left and right eyes by the magnification change and the position of the intersection of the optical axes of the two imaging optical systems, at a low magnification, in a case where focal positions on left and right optical axes by the magnification change (at a high magnification) are shifted with respect to the position of the intersection of the optical axes of the two imaging optical systems, and at a high magnification, respectively, in the medical stereo observation system of the fifth embodiment.
Figure 27B:
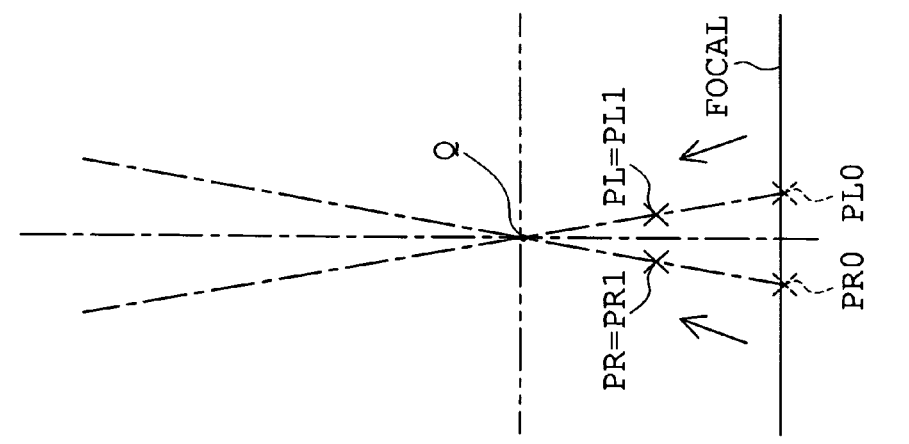
Figure 27C:
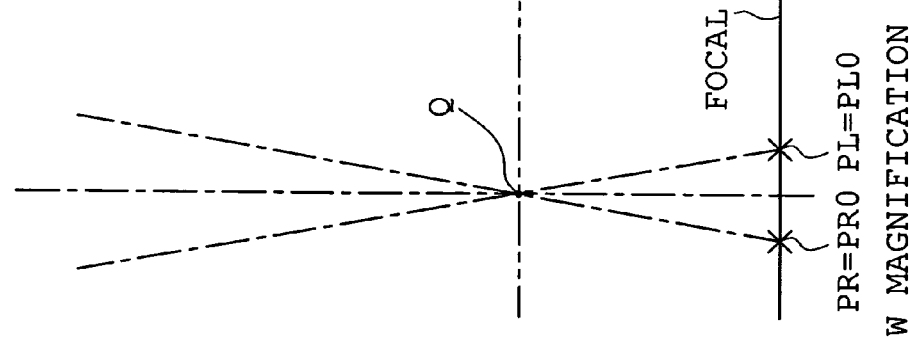
Figure 28A:
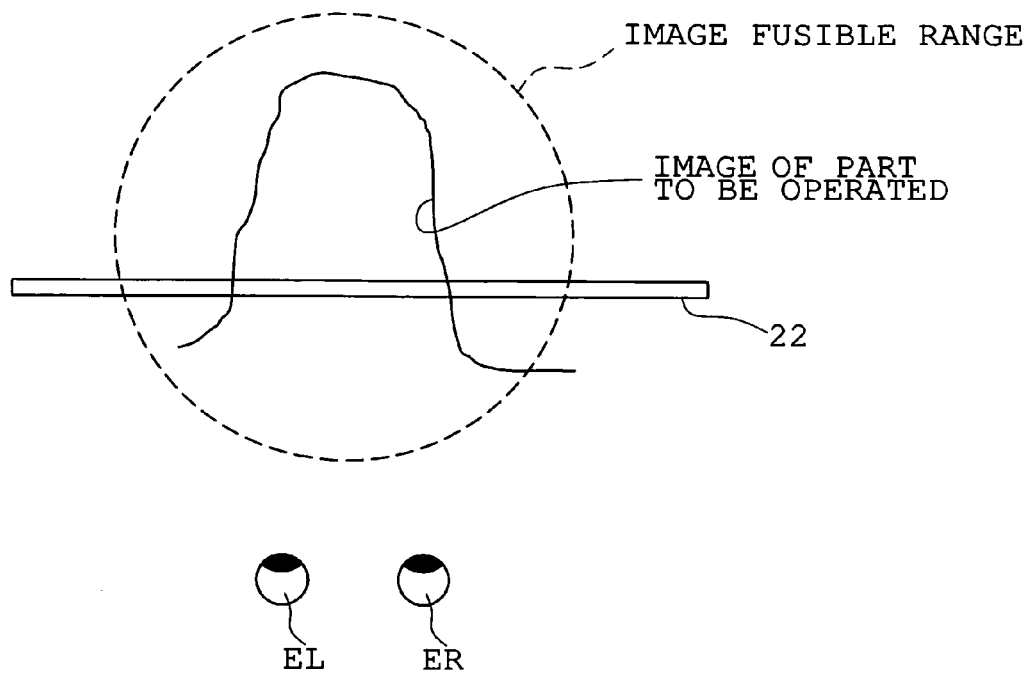
FIGS. 28A and 28B are explanatory views showing the relationship between a panel surface to be displayed and a part to be reproduced, at low and high magnifications, respectively, in the medical stereo observation system of the fifth embodiment.
Figure 28B:
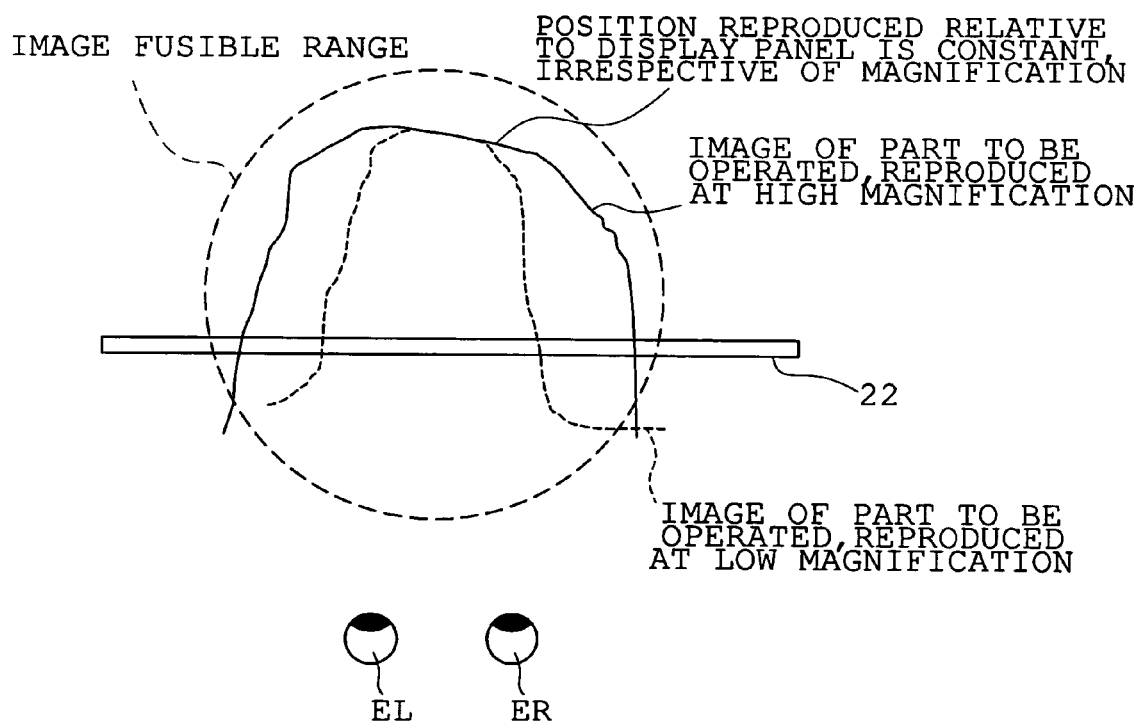

FIG. 24 is an explanatory view showing a fundamental structure common to the medical stereo observation systems of individual embodiments of the present invention; FIG. 25 is an explanatory view showing the optical structure of imaging optical systems for left and right eyes used in the medical stereo observation system of a fifth embodiment, positions of individual optical members at a low magnification, an intersection of optical axes on the observation object side in the imaging optical systems for left and right eyes, and individual focal positions of the imaging optical systems for left and right eyes relative to a focal plane; FIG. 26 is an explanatory view showing the optical structure of imaging optical systems for left and right eyes used in the medical stereo observation system of the fifth embodiment, positions of individual optical members at a high magnification, an intersection of optical axes on the observation object side in the imaging optical systems for left and right eyes, and individual focal positions of the imaging optical systems for left and right eyes relative to a focal plane; FIG. 27 is an explanatory view showing focal points of the imaging optical systems for left and right eyes by the magnification change and the position of the intersection of the optical axes of the two imaging optical systems; FIG. 27A shows a position at a low magnification; FIG. 27B shows a state in a case where focal positions on left and right optical axes by the magnification change (at a high magnification) are shifted with respect to the position of the intersection of the optical axes of the two imaging optical systems; FIG. 27C shows a position at a high magnification, in the medical stereo observation system of the fifth embodiment; FIG. 28 is an explanatory view showing the relationship between a panel surface to be displayed and a part to be reproduced; FIG. 28A shows a state at a low magnification, and FIG. 28B shows a state at a high magnification, respectively, in the medical stereo observation system of the fifth embodiment;

The medical stereo observation system of the present invention is constituted by a stereo imaging apparatus 221 and a stereo image display device 222. The stereo imaging apparatus 221 comprises a mirror part 311 having an imaging optical system for picking up an image for left eye and for right eye and a support means 312, such as a multi-articulated arm, for supporting the mirror part 311 to be freely movable. The imaging optical system for left eye and for right eye comprises an objective optical system, a variable magnification optical system, an image-forming optical system, and an image sensor (omitted in FIG. 24), to enlarge and pick up an observation object such as a part to be operated as a three-dimensionally observable electronic image.

The stereo image display device 222 comprises image projectors 321L and 321R for left and right eyes for projecting an image for left and right eye imaged through the stereo imaging apparatus 221, a display panel 322, and a support means 323, such as a multi-articulated arm, for supporting the image projectors 321L and 321R and the display panel 322 to be freely movable. The image projectors 321L and 321R for left and right eyes have projection optical systems (illustration is omitted), each of which has an image display element and a projection lens. It is arranged so that exit-side optical axes OL and OR of the respective projection optical systems meet each other at the center S of the display surface of the display panel 322, and observation images from the image projectors 321L and 321R for left and right eyes are projected on the display panel 322 as corresponding to each other.

The display panel 322 is constituted with, for example, a Fresnel concave mirror and a diffusion board. (illustration is omitted).

And it is constituted such that exit pupils of the projection optical systems of the image projectors 321L and 321R for left and right eyes are enlarged at a position having a predetermined distance from the center S of the display surface of the display panel 322, and are formed separately in right and left by the lens function of the Fresnel concave mirror of the display panel 322, and the optical diffusion function of the diffusion board.

By setting left and right eyes EL and ER of a viewer D (a person carrying out surgical operation) within left and right exit pupils, an observation image from the image projector 321L for left eye is transmitted into the left eye EL of the viewer D looking at the display panel 322 with a reflecting light axis WL being at the center of the image, and an observation image from the image projector 321R for right eye is transmitted into the right eye ER of the viewer D with a reflecting light axis WR being at the center of the image. Consequently, an observation image projected on the display panel 322 from the image projectors for left and right eyes 321L and 321R can be observed stereoscopically by the viewer D. These constitutions are common in embodiments to be described later.

The medical stereo observation system of the fifth embodiment, as shown in FIG. 25, comprises, in the mirror part 311 of the stereo imaging system 221, one objective optical system 311*a* common to left and right eyes, two variable magnification optical systems 311*b*L and 311*b*R for left and for right eyes, two image-forming optical systems for left and right eyes 311*c*L and 311*c*R, two image sensors for left and right eyes 311*d*L and 311*d*R, an objective lens holding component 311*e*, a magnification lens holding components 311*f*2 and 311*f*2, a guide component 311*g*, an objective lens guide shaft 311*h*, a magnification lens guide shafts 311*i* and 311*j*, a cam shaft 311*k*, and a motor 311*l*.

Further, an imaging optical system for left eye 311L is constituted with the objective optical system 311*a*, the variable magnification optical system for left eye 311*b*L, the image-forming optical system for left eye 311*c*L, and the image sensor for left eye 311*d*L, while an imaging optical system for right eye 311R is constituted with the objective optical system 311*a*, the variable magnification optical system for right eye 311*b*R, the image-forming optical system for right eye 311*c*R, and the image sensor for right eye 311*d*R. The variable magnification optical systems 311*b*L and 311*b*R, the image-forming optical systems 311*c*L and 311*c*R, the image sensors for left and right eyes 311*d*L and 311*d*R are arranged on optical axes O2 and O3 which are parallel at imaging side to the central optical axis O1 of the objective optical system 311*a*. The objective optical system 311*a* is constituted with a convex lens, and has a function which ejects incident light as parallel light.

The two variable magnification optical systems for left and right eyes 311*b*L and 311*b*R, comprise lens groups 311*b*L1, 311*b*L2, 311*b*R1, 311*b*R2, 311*b*L3, and 311*b*R3, respectively. The image-forming optical systems for left and right eyes 311*c*L and 311*c*R are constituted with image-forming-lens, respectively. The two image-forming optical systems for left and right eyes 311*c*L and 311*c*R, has a function which carries out image forming of the observation image of a part to be operated on the two image sensors for left and right eyes 311*d*L and 311*d*R. The image sensors for left and right eyes 311*d*L and 311*d*R are constituted with CCD etc.

The objective holding component 311*e* holds the object optical system 311*a*. The variable magnification lens holding component 311*f*1 holds the second lens group for left and right eyes 311*b*L2 and 311*b*R2. The variable magnification lens holding component 311*f*2 holds the third lens groups 311*c*L3 and 311*c*R3 for left and right eyes. The guide component 311*g* is constituted with a cylinder-shape component arranged in parallel with optical axes O1, O2 and O3 at an image pickup side of the objective optical system 311*a*. The guide component 311*g* is inserted through a pore 311*ea* arranged at the one end part of the objective holding component 311*e*, a pore 311*f*1*a* arranged at the one end part of the magnification lens holding component 311*f*, and a pore 311*f*2*a* arranged at one end part of the magnification lens holding component 311*f*2, and furthermore, it is constituted so that the guide component 311*g* can guide an objective holding component 311e, the objective lens held on the variable magnification lens holding components 311f1 and 311f2, and the variable magnification lens along (here, in parallel to) the central optical axis O1 of the objective optical system 311a.

Guide shafts 311h, 311i and 311j are fixed at other end part 311eb of the objective holding component 311e, and other end parts 311f1b and 311f2b of the variable magnification lens holding components 311f1 and 311f2, respectively. Moreover, each free end of them is fitted into a predetermined part of the guide grooves 311k1, 311k2 and 311k3 arranged on a cam shaft 311k, respectively. And, it has a function that transmits power by which the objective holding components 311e, and the variable magnification lens holding components 311f1 and 311f2 are moved along (here, in parallel to) the central optical axis O1 of the objective optical system 311a, cojointly with a guide component 311g, by being guided toward a predetermined direction via the guide grooves 311k1, 311k2 and 311k3 when the cam shaft 311k is rotated.

The guide grooves 311kl, 311k2 and 311k3 are spirally formed in a predetermined direction at an predetermined angle so that a predetermined amount of movement of the objective holding components 311e and 311f of the variable magnification lens holding components 311f1 and 311f2 can be carried out in the predetermined direction (a direction in which the components approach to or depart from an observation object, that is, a part to be operated), respectively. A motor 311l is constituted so that the cam shaft 311k may be rotated. By driving the motor 311l, the second and third lens groups 311bL2, 311bL3, 311bR2 and 311bR3 of variable magnification optical systems 311bL and 311bR, and the objective optical system 311a, are moved by a predetermined amount in parallel with the central optical axis O1 of the objective optical system 311a, and thus, adjustment of magnification change and a focal position are carried out.

Optical axes O2a and O3a at an observation object side of the imaging optical systems 311L and 311R for left and right eyes cross at the image pickup side departed from the focal plane (a position where a viewer desires for observation of a part to be operated) of an observation object. Further, each of focal planes PL and PR of the two imaging optical systems 311L and 311R can be moved between an intersection Q of the optical axes O2a and O3a at the observation object side in the two imaging optical systems 311L and 311R, and focal planes PL0 and PR0 at a low magnification, in association with magnification change through variable magnification optical systems 311bL and 311bR. And it is constituted such that focal positions PL and PR are always located at a focal plane at magnification change.

As to this point, it will be explained in detail using FIGS. 26 and 27. FIG. 25 shows a state at a low magnification. The intersection Q of the optical axis at the observation object side in the imaging optical systems for left and for right eyes 311L and 311R is located at the imaging system side rather than the focal plane in the observation object. The focal positions PL and PR of the imaging optical systems 311L and 311R of the right and left sides at this time are located in predetermined positions PL0 and PR0 on a focal plane, respectively. In this state, if a magnification-change-switch which is not illustrated, is pushed by a person carrying out a surgical operation, the motor 311l is driven, the cam shaft 311k is rotated, the guide axes 311h, 311i and 311j are moved toward a predetermined direction via the guide grooves 311k1, 311k2 and 311k3, and then as shown in FIG. 26, the objective optical system 311a, and the second and third lens groups 311bL2, 311bL3, 311bR2 and 311bR3 in the variable magnification optical systems 311bL and 311bR are moved toward the position shown by the solid line from the position shown by the dashed line at a low magnification.

Here, a case where a magnification change is carried out by moving only a conventional variable magnification optical system is supposed. In this case, only the magnification will become large without changing a focal position at a low magnification. Accordingly, as shown in FIG. 25, the amount of parallax of an image for left eye and an image for right eye become large too much. Consequently, it is apt to be unable to make an image fusion.

On the other hand, in the medical stereo observation apparatus of the fifth embodiment, as mentioned above, each of focal positions PL and PR of the two imaging optical systems 311L and 311R can be moved between the intersection Q of the optical axes O2a and O3a at the observation object side in the two imaging optical systems 311L and 311R, and focal planes PL0 and PR0 at a low magnification, in association with magnification change through variable magnification optical system 311bL and 311bR. And the focal positions PL and PR are always positioned at the focal plane when magnification is changed. Therefore, the amount of parallax on a display panel surface can be kept within an image fusible range.

The relationship between magnification and focal position when magnification is changed will be explained. It is assumed that a magnification at low magnification as shown in FIG. 25 is β; a distance from the intersection Q of the optical axes O2a and O3a at the observation object side in the two imaging optical systems 311L and 311R to a focal plane as shown in FIG. 25 is l; a magnification at high magnification as shown in FIG. 26 is β'; a distance from the intersection Q of the optical axes O2a and O3a at the observation object side in the two imaging optical systems 311L and 311R to a focal plane as shown in FIG. 26 is l'. When an angle at which two optical axes O2a and O3a intersect is represented by α, this angle α becomes constant irrespective of magnification change in the medical stereo observation apparatus of the fifth embodiment. In this case, the following condition is satisfied.

$$l \cdot \beta \cdot \sin(\alpha/2) = l' \cdot \beta' \cdot \sin(\alpha/2)$$

In the medical stereo observation system of the fifth embodiment, it is constituted such that the focal positions PL and PR are always positioned at the focal plane by shifting the intersection Q of the optical axes O2a and O3a at the observation object side in the two imaging optical systems 311L and 311R toward the observation object side, in the magnification change from a low magnification to a high magnification. As to an adjustment operation of the focal position by this magnification change, it will be explained in detail using FIGS. 27 and 28.

At the state of a low magnification shown in FIG. 25, each of focal positions PL and PR of the two imaging optical systems 311L and 311R for left and right eyes, is located at positions PL0 and PR0 on the focal plane, as shown in FIG. 27A. When magnification is changed from this state to a high magnification as shown in FIG. 26, focal positions PL and PR, as shown in FIG. 27B, are moved toward predetermined positions PL1 and PR1 where these positions approach to the intersection Q from the focal plane. Thereby, the amount of parallax on a panel surface can be kept at a constant rate in which image is fusible, and the image of an observation object can be reproduced. However, if a focal position is shifted to the front side from a focal plane, a blur will arise in the observation image in the depth position at which observation is desired. Then, in order to prevent the blur of this image, when magnification change operation is carried out from a low magnification to a high magnification, and at the same time, by shifting the objective optical system 311a toward the observation object side by the amount of movement of the focal positions PL and PR which have moved toward the imaging surface side in the magnification change, as shown in FIG. 27C, while keeping the relative spatial relationship of the intersection Q and focal position PL1 and PR1 shown in FIG. 27B, the focal positions PL and PR are made coincided with the focal plane. In order to eliminate such image blur, in the fifth embodiment, it is constituted such that only the objective optical system 311a is moved in association with magnification change via the variable magnification optical systems 311bL and 311bR. However, it may be constituted so that the mirror part 311 whole is moved.

As for a reproduction state on the surface of the display panel 322 of an image which has been picked up when magnification is changed from a low magnification to a high magnification, it will be explained. It is assumed that FIG. 28A is an image of a part to be operated which has been picked up at a low magnification, as shown in FIG. 27A, and has been reproduced on the surface of the display panel 322. The image of the part to be operated picked up at a high magnification as shown in FIG. 27C has the same focal position to the focal position at a low magnification as shown by a solid line in FIG. 28B, and it is enlarged and reproduced in a state having coincided with the focal plane at a low magnification. Therefore, according to the medical stereo observation system of the fifth embodiment, even if magnification ratio of the magnification change at the time of picking up an image differs, images for left and right eyes can be reproduced on a surface of the display panel 322, suppressing the amount of parallax within a limit in which an image is fusible. Thus, a viewer can observe by making an image fusion comfortably. Further, according to the medical stereo observation system of the fifth embodiment, even if the objective optical system 311a is moved, an angle of intersection of the optical axes O2 and O3 at the observation object side in the two imaging optical systems 311L and 311R is not changed. Therefore, an observation image with a constant stereoscopic effect can be obtained irrespective of change of magnification.

Sixth Embodiment

Figure 29:
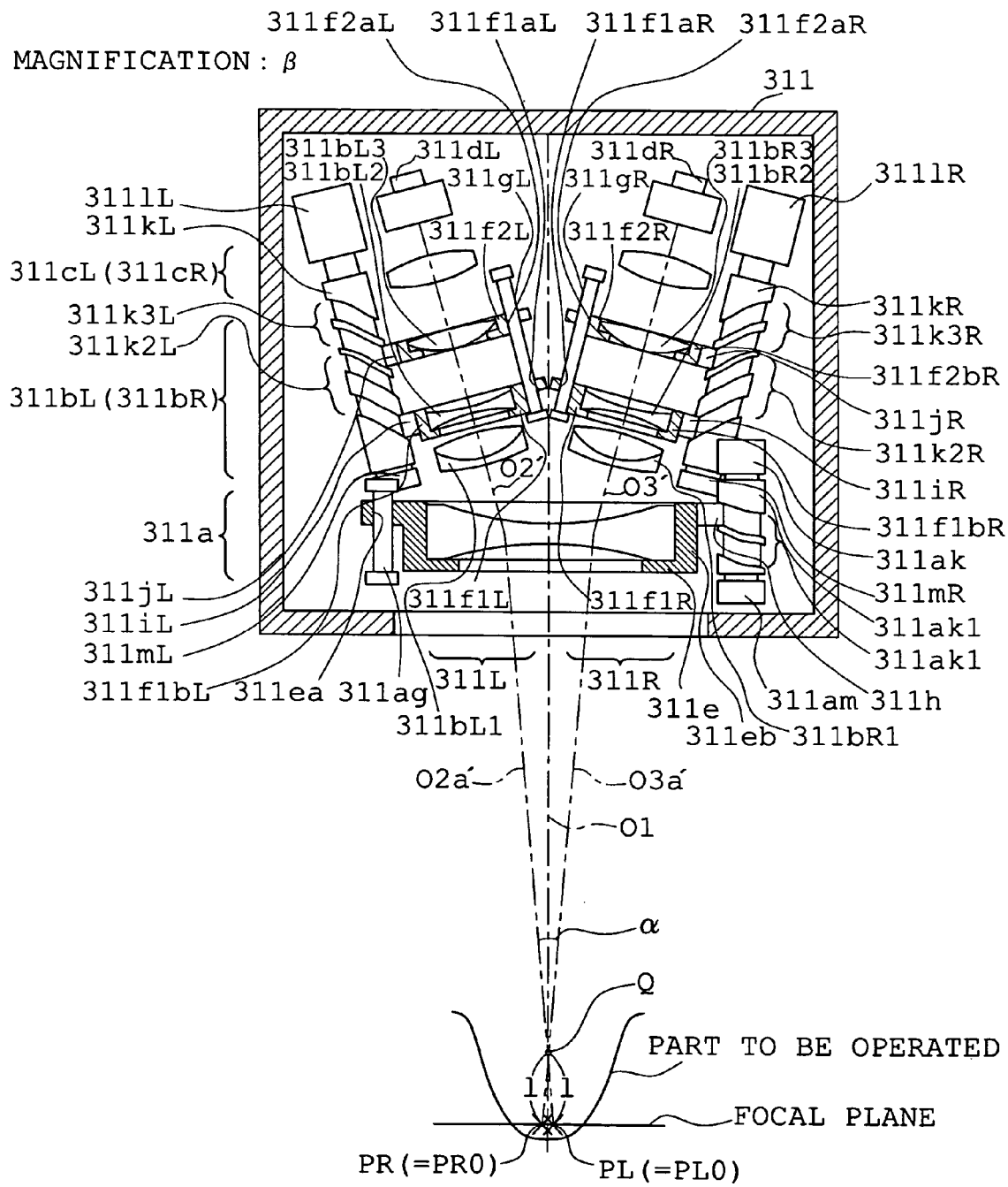
FIG. 29 is an explanatory view showing the optical structure of imaging optical systems for left and right eyes used in the medical stereo observation system of a sixth embodiment of the present invention, positions of individual optical members at a low magnification, an intersection of optical axes on the observation object side in the imaging optical systems for left and right eyes, and individual focal positions of the imaging optical systems for left and right eyes relative to a focal plane.
Figure 30:
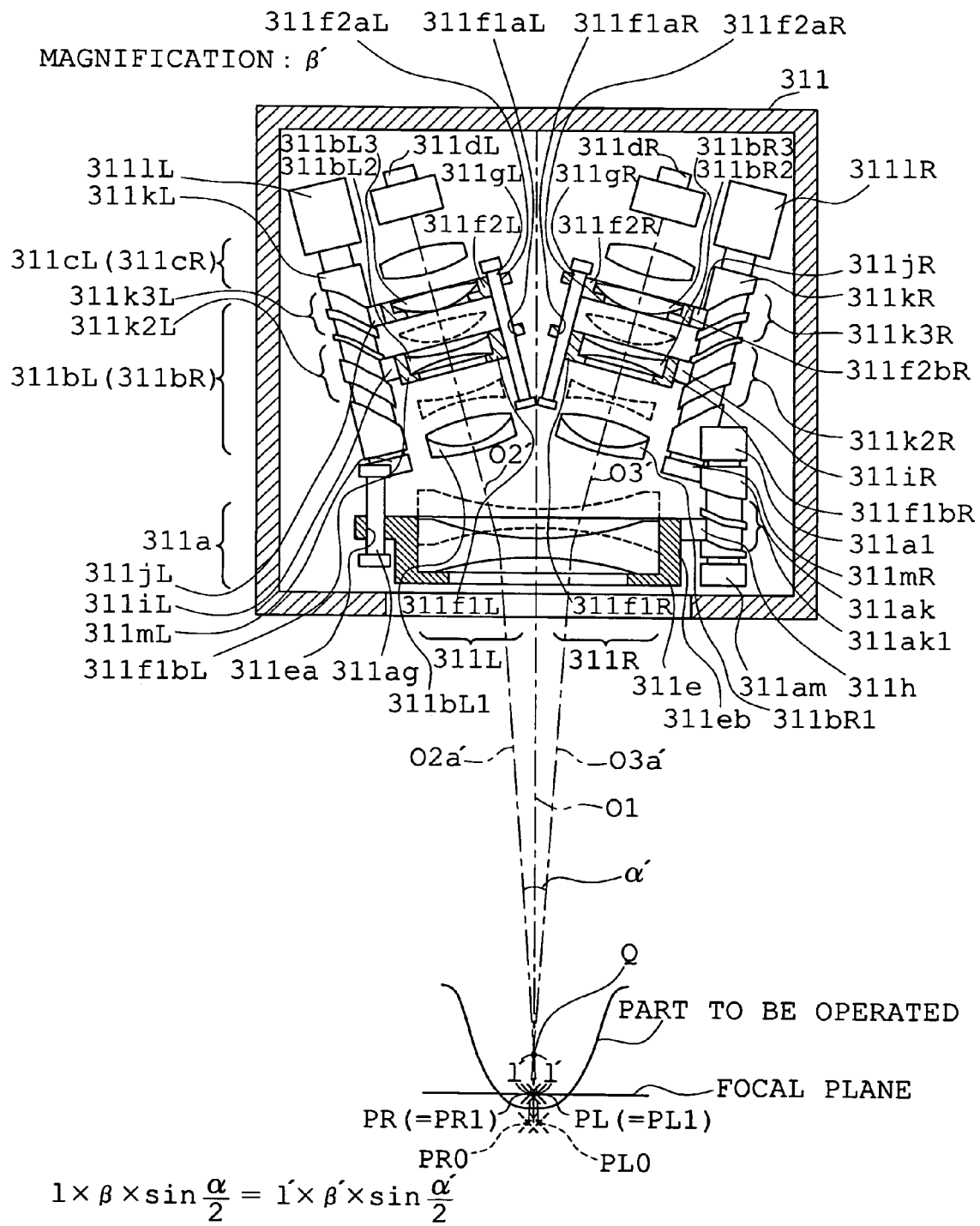
FIG. 30 is an explanatory view showing the optical structure of imaging optical systems for left and right eyes used in the medical stereo observation system of the sixth embodiment, positions of individual optical members at a high magnification, an intersection of optical axes on the observation object side in the imaging optical systems for left and right eyes, and individual focal positions of the imaging optical systems for left and right eyes relative to a focal plane.

FIG. 29 is an explanatory view showing the optical structure of imaging optical systems for left and right eyes used in the medical stereo observation system of a sixth embodiment of the present invention, positions of individual optical components at a low magnification, an intersection of optical axes on the observation object side in the imaging optical systems for left and right eyes, and individual focal positions of the imaging optical systems for left and right eyes relative to a focal plane; FIG. 30 is an explanatory view showing the optical structure of imaging optical systems for left and right eyes used in the medical stereo observation system of the sixth embodiment, positions of individual optical components at a high magnification, an intersection of optical axes on the observation object side in the imaging optical systems for left and right eyes, and individual focal positions of the imaging optical systems for left and right eyes relative to a focal plane.

In the medical stereo observation system of the sixth embodiment, the objective optical system 311a arranged at the inside of the mirror part 311 in the stereo imaging apparatus 311 comprises a concave lens, and has a function that ejects incident light as diverging light. The two variable magnification optical systems 311bL and 311bR for left and for right eyes, the image-forming optical systems 311cL and 311cR, and the image sensors 311dL and 311dR are arranged on optical axes O2' and O3' at an imaging side, at an angle to the central optical axis O1 of the objective optical system 311a. The objective optical system 311a, and the variable magnification optical system for left eye 311bL and the variable magnification optical system for right eye 311bR have individually and independently, a guide, a guide shaft, a cam, a motor, and an encoder.

An object optical system guide component 311ag is constituted with a cylinder-shape component arranged in parallel with the central optical axis O1 of the objective optical system 311a. The object optical system guide component 311ag is inserted through a pore 311ea arranged at the one end part of the objective holding component 311e, and the objective lens held at the objective lens holding component 311e can be guided in parallel along the central optical axis O1 of the objective optical system 311a.

An objective optical system guide shaft 311h is fixed to other end part 311eb of the objective holding component 311e, and each free end is fitted into a predetermined part of an object optical system guide groove 311ak1 arranged at an object optical system cam shaft 311ak, respectively. And, it has a function to transmit the power by which the objective holding component 311e is moved in parallel along the central optical axis of the objective optical system 311a, cojointly with the object optical system guide component 311ag, by the free end being guided to a predetermined direction through the object optical system guide groove 311ak1, when the object optical system cam shaft 311ak is rotated, An object optical system guide groove 311ak1 is spirally formed in a predetermined direction and at a predetermined angle so that the objective holding component 311e may be moved in a predetermined direction (a direction in which the components approach to or depart from an observation object, that is, a part to be operated) and by a predetermined amount. An objective optical system motor 311al is constituted so as to rotate the object optical system cam shaft 311ak. An objective optical system encoder 311am is constituted so as to detect the amount of rotation of the object optical system cam shaft 311ak by driving of the objective optical system motor 311al. It is constituted such that a signal of the amount of rotation detected by the objective optical system encoder 311am is fed back to the control part in which illustration is omitted, and it is used, for example, for control of driving-stop of objective optical system motor 311al and the like.

The magnification lens guide components for left and right eyes 311gL and 311gR are constituted with cylinder-shape components arranged in parallel with optical axes O2' and O3' at the image pickup side of the objective optical system 311a, respectively. And these are inserted through pores 311f1aL and 311f1aR arranged at one end part of magnification lens holding components 311f1L and 311f1R for left and right eyes, respectively, and inserted through pores 311f2aL and 311f2aR arranged at one end part of magnification lens holding components for left and right eyes 311f2L and 311f2R. Further, these are constituted such that magnification change lenses for left and right eyes arranged at magnification lens holding components for left and right eyes 311f1L, 311f2L, 311f1R and 311f2R may be guided along optical axes of the two variable magnification optical systems for left and for right eyes 311bL and 311bR, respectively (here, these axes are coincided with optical axes O2' and O3' at the image pickup side of the objective optical system 311a).

The magnification lens guide shafts for left and right eyes 311jL, 311iR and 311jR are fixed at other end parts 311f1bL, 311f2bL, 311f1bR and 311f2bR of the magnification lens holding components for left and right eyes 311f1L, 311f2L, 311f1R and 311f2R, and each free end is fitted into a predetermined part of the magnification lens guide grooves for left eye and right eyes 311k2L, 311k3L, 311k2R, and 311k3R which are arranged at magnification lens drive cam shafts for left and right eyes 311kL and 311kR, respectively. The constitution has a function to transmit a power for moving magnification lens holding components for left and right eyes 311f1L, 311f2L, 311f1R and 311f2R along the optical axes of the two variable magnification optical systems for left and for right eyes 311bL and 311bR via magnification lens guide grooves for left and for right eyes 311k2L, 311k3L, 311k2R and 311k3R, by the free end being guided to a predetermined direction, cojointly with magnification lens guide components for left and right eyes 311gL and 311gR, (here, these are coincided with optical axes O2' and O3' at the image pickup side of the objective optical system 311a) when magnification lens drive cam shafts for left and right eyes 311kL and 311kR are rotated.

The magnification lens guide grooves for left and right eyes 311k2L, 311k3L, 311k2R and 311k3R are spirally formed in a predetermined direction and at a predetermined angle so that the magnification lens holding components for left and right eyes 311f1L, 311f2L, 311f1R and 311f2R are moved toward a predetermined direction (a direction in which the components approach to or depart from an observation object, that is, a part to be operated) by a predetermined amount. The magnification lens drive motors for left and right eyes 311lL and 311lR are constituted so as to rotate the magnification lens drive cam shafts for left and right eyes 311kL and 311kR. Encoders for detecting the amount of magnification changes for or left and right eyes 311mL and 311mR are constituted so as to detect the amount of rotation of the magnification lens drive cam shafts for left and right eyes 311kL and 311kR by driving of the magnification lens drive cam shafts for left and right eyes 311lL and 311lR, And by driving the magnification lens drive motors for left and right eyes 311lL and 311lR, and the objective optical system motor 311ak, the second and third lens groups 311bL2, 311bL3, 311bR2 and 311bR3 of the variable magnification optical systems 311bL and 311bR, and the objective optical system 311a are moved by a predetermined amount along each of optical axes O2', O3' and O1. Thus, adjustments of magnification change and focal position are carried out.

Optical axes O2a' and O3a' at the observation object side of the imaging optical systems 311R and 311L for left and right eyes cross at the imaging side rather than the focal plane (a position where a viewer desires for observation of a part to be operated) of an observation object. Further, each of focal planes PL and PR of the two imaging optical systems 311L and 311R is moved between the intersection Q of the optical axes O2a' and O3a' at the observation object side in the two imaging optical systems 311L and 311R, and focal positions PL0 and PR0 at a low magnification in association with magnification change via the variable magnification optical systems 311bL and 311bR. And the focal positions PL and PR are always positioned at the focal plane when magnification is changed.

FIG. 29 shows a state at a low magnification. The intersection Q of optical axes O2a' and O3a' at the observation object side in the imaging optical systems 311L and, 311R for left and for right eyes is located at the image pick-up side rather than the focal plane in an observation object. The focal positions PL and PR of the imaging optical systems 311L and 311R for right and left eyes at this time are located at predetermined positions PL0 and PR0 on the focal planes, respectively. In this state, if a magnification-change-switch which is not illustrated, is pushed by a person carrying out a surgical operation, magnification lens drive motor for left and right eyes 311lL and 311lR are driven, and magnification lens drive cam shafts for left and right eyes 311kL and 311kR are rotated, via the magnification lens guide grooves for left and for right eyes 311k2L, 311k3L, 311k2R and 311k3R. Then, the magnification lens guide shafts for left and right eyes 311jL, 311iR and 311jR are moved toward a predetermined direction, and as shown in FIG. 30, the second and third lens groups 311bL2, 311bL3, 311bR2 and 311bR3 in the variable magnification optical systems 311bL and 311bR are moved toward the position shown by a solid line from the position shown by a dashed line at a low magnification. Thereby, magnification change is carried out.

At this time, encoders for detecting an amount of magnification changes for right and left eyes 311mL and 311mR detect the amount of rotation of the magnification lens drive cam shafts for left and right eyes 311kL and 311kR, and transmits to a control part which is not illustrated, as a signal. According to an inputted signal, the control part computes the amount of movement of the objective optical system 311a, and computes also the number of rotation of the objective optical system motor 311a1 which is necessary for movement of the computed predetermined amount, and transmits the signal of the computed amount of rotation to the objective optical system motor 311ak. The objective optical system motor 311a1 is driven based on the amount of rotation transmitted, and the object optical system cam shaft 311ak is rotated, and the objective optical system guide shaft 311h is moved toward a predetermined direction via the object optical system guide groove 311ak1. Thus, as shown in FIG. 30, the objective optical system 311a is moved to the position shown by the solid line from the position shown by the dashed line at a low magnification.

Here, the amount of movement of the objective optical system 311a in the medical stereo observation system of the sixth embodiment can be calculated as follows. In the medical stereo observation system of the sixth embodiment, also it is constituted such that in association with magnification change of the variable magnification optical system 311bL and 311bR, each of focal positions PL and PR of the two imaging optical systems 311L and 311R are moved between an intersection Q of the optical axes O2a' and O3a' at the observation object side in the two imaging optical systems 311L and 311R and the focal positions PL0 and PR0 at a low magnification. And, the focal positions PL and PR are always positioned at the focal plane when magnification is changed. Therefore, the amount of parallax on a display panel surface can be kept within an image fusible range.

The relationship between magnification and focal position when magnification is changed will be explained. In the medical stereo observation system of the sixth embodiment, the two variable magnification optical systems 311bL and 311bR for left and for right eyes, the image-forming optical systems 311cL and 311cR, and the image sensors 311dL and 311dR are arranged on the optical axes O2' and O3' at image pickup side, at an angle to the central optical axis O1 of the objective optical system 311a. Therefore, according to the variable magnification optical systems 311bL and 311bR, an intersected angle of the optical axes O2a and O3a at an observation object side in the imaging optical systems 311L and 311R for left and right eyes are changed. It is assumed that for example, the magnification in the at a low magnification as shown in FIG. 29 is β; a distance from an intersection Q of the optical axes O2a' and O3a' at the observation object side in the two imaging optical systems 311L and 311R to a focal plane as shown in FIG. 29 is l; an angle at which two optical axes O2a and O3a cross is α; the magnification at a high magnification shown in FIG. 30 is β'; a distance from an intersection Q of the optical axes O2a' and O3a' at the observation object side in the two imaging optical systems 311L and 311R to a focal plane as shown in FIG. 30 is l; and an angle at which two optical axes O2a' and O3a' cross is α'. At this time, the following condition is made up.

$$l \cdot \beta \cdot \sin(\alpha/2) = l' \cdot \beta' \cdot \sin(\alpha'/2)$$

In the medical stereo observation system of the sixth embodiment, it is constituted such that the focal positions PL and PR are always positioned at the focal plane by shifting the intersection Q of the optical axes O2a' and O3a' at the observation object side in the two imaging optical systems 311L and 311R toward the object side in the magnification change from low magnification to high magnification An adjustment operation of the focal position by this magnification change is the same as explained in detail using FIGS. 27 and 28.

In the state at the low magnification shown in FIG. 29, the focal positions PL and PR of the imaging optical systems 311L and 311R for right and left eyes at this time are located at predetermined positions PL0 and PR0 on the focal planes, as shown in FIG. 27A. When magnification is changed from this state to a high magnification as shown in FIG. 30, the focal positions PL and PR are moved toward predetermined positions PL1 and PR1 where these positions approach to the intersection Q from the focal plane as shown in FIG. 27B. Thereby, the amount of parallax on a panel surface is kept constant so as to be fusible, and the image of an observation object can be reproduced. However, if a focal position is shifted to the front side from a focal plane, a blur in the observation image will generate in the depth position at which observation is desired. Then, in order to prevent such image blur, the focal positions PL and PR are made coincided with the focal plane when magnification change operation is carried out from low magnification to high magnification, at the same time, as shown in FIG. 27C, by shifting the objective optical system 311a toward the observation object side by the amount of movement of the focal positions PL and PR which have moved toward the imaging surface side in the magnification change, as shown in FIG. 27C, while maintaining the relative spatial relationship of the intersection Q and focal position PL1 and PR1 shown in FIG. 27B.

In order to eliminate such image blur, according to the sixth embodiment, it is constituted such that only the objective optical system 311a is moved in association with magnification change via the variable magnification optical systems 311bL and 311bR. However, it may be constituted such that the mirror part 311 whole is moved according to the output of encoders 311mL and 311mR.

According to the medical stereo observation system of the sixth embodiment, by changing relative positions of lenses constituting the variable magnification optical systems 311bL and 311bR, the objective optical system 311a, the intersected angle of the optical axes O2a' and O3a' at an observation object side in the imaging optical systems for left and right eyes 311L and 311R is changed. Therefore, comparing with the fifth embodiment, the amount of movement of the intersection Q of the two optical axes to movement of the objective optical system 311a can be made large, (an effect of the objective optical system 311a is strengthened), and accordingly, the amount of movement of an objective lens can be made small.

Seventh Embodiment

Figure 31:
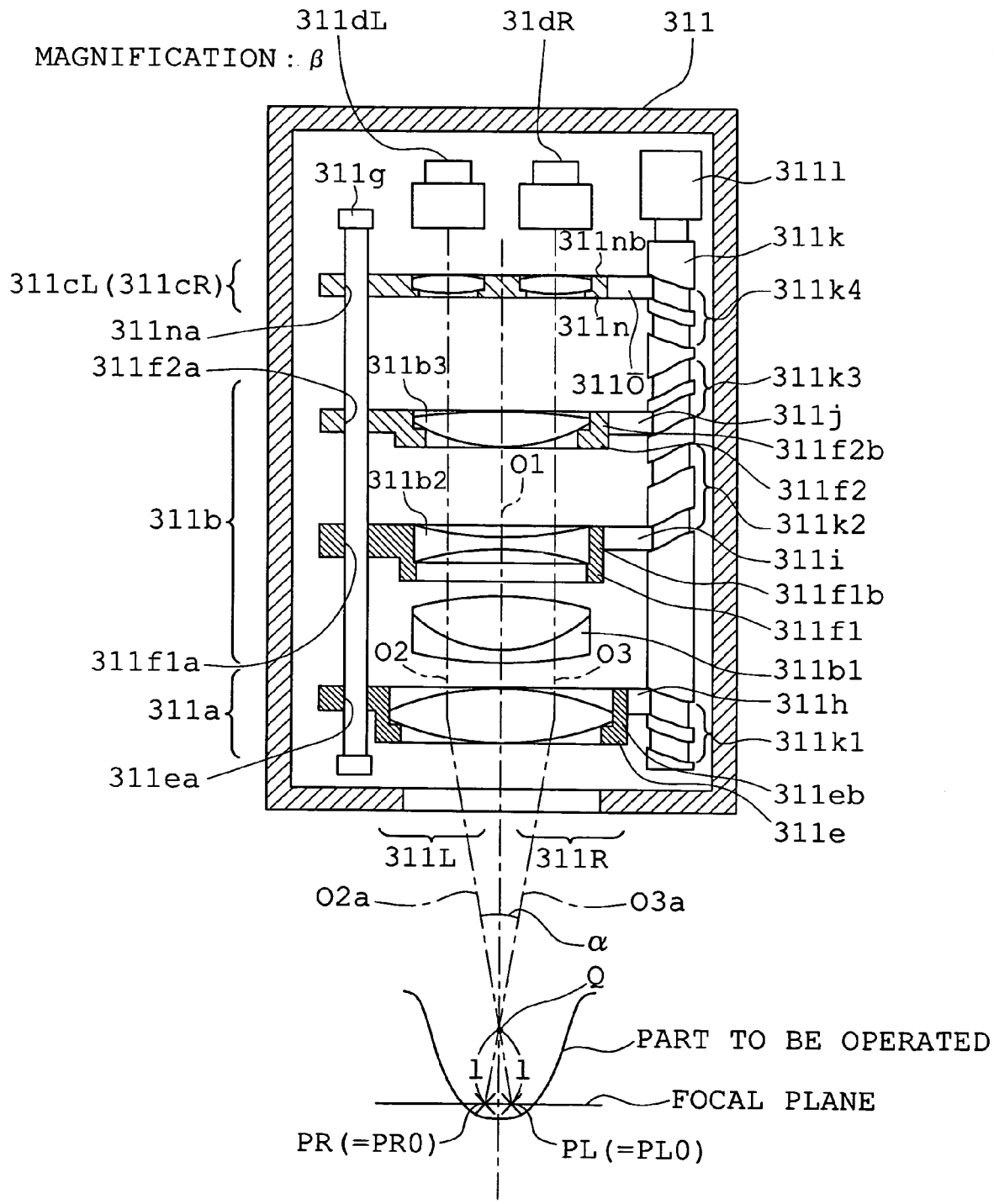
FIG. 31 is an explanatory view showing the optical structure of imaging optical systems for left and right eyes used in the medical stereo observation system of a seventh embodiment of the present invention, positions of individual optical members at a low magnification, an intersection of optical axes on the observation object side in the imaging optical systems for left and right eyes, and individual focal positions of the imaging optical systems for left and right eyes relative to a focal plane.
Figure 32:
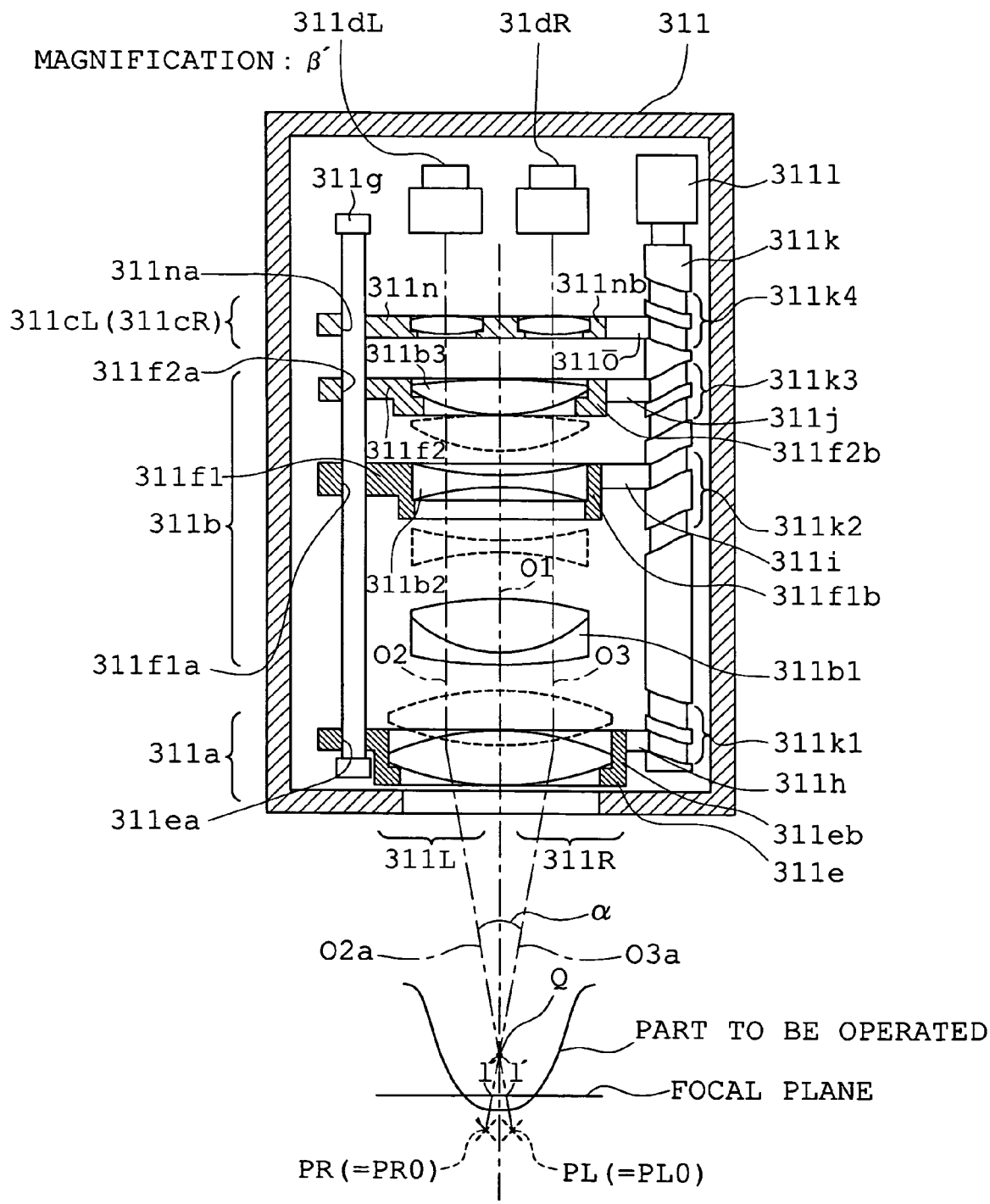
FIG. 32 is an explanatory view showing the optical structure of imaging optical systems for left and right eyes used in the medical stereo observation system of the seventh embodiment, positions of individual optical members at a high magnification, an intersection of optical axes on the observation object side in the imaging optical systems for left and right eyes, and individual focal positions of the imaging optical systems for left and right eyes relative to a focal plane.

FIG. 31 is an explanatory view showing the optical structure of imaging optical systems for left and right eyes used in the medical stereo observation system of a seventh embodiment of the present invention, positions of individual optical components at a low magnification, an intersection of optical axes on the observation object side in the imaging optical systems for left and right eyes, and individual focal positions of the imaging optical systems for left and right eyes relative to a focal plane; FIG. 32 is an explanatory view showing the optical structure of imaging optical systems for left and right eyes used in the medical stereo observation system of the seventh embodiment, positions of individual optical components at a high magnification, an inter-section of optical axes on the observation object side in the imaging optical systems for left and right eyes, and individual focal positions of the imaging optical systems for left and right eyes relative to a focal plane;

In the medical stereo observation system of the seventh embodiment, the variable magnification optical system 311b at the inside of the mirror part 311 in the stereo imaging apparatus 221 is constituted using a single zoom lens common to left and right eyes. The image-forming optical systems 311cL and 311cRa for left and right eyes are held by the image-forming-lens holding component 311n. In a pore 311na arranged at the one end part of the image-forming-lens holding component 311n, a guide component 311g is inserted through. The image-forming-lens guide shaft 311o is fixed to the other end part 311nb of the image-forming-lens component 311n. The image-forming-lens guide shaft 311o is being fixed. In a cam shaft 311k, an image-forming-lens guide groove 311k4 is formed, and a free end part of an image-forming-lens guide shaft 311o fixed to an image forming holding component 311n is fitted into. And it is constituted such that when the object optical system cam shaft 311k is rotated, the free end part is guided to a predetermined direction via the image-forming-lens guide 311k4, cojointly with a guide component 311g, and accordingly the image-forming optical systems 311cL and 311cR for left and right eyes are moved along the optical axes O2 and O3 at the image pickup side of the objective optical system 311a.

When magnification is changed from a low magnification to a high magnification by moving the variable magnification optical system 311b, the image-forming optical systems 311cL and 311cR are moved so that the focal positions PL and PR for left and right eyes approach to the intersection Q of the optical axes O2a and O3a at the observation object side of the imaging optical systems 311R and 311L. And, the focal positions PL and PR are always positioned at the focal plane when magnification is changed. In order to eliminate an image blur generated by movement of a focal position, as the same to the fifth embodiment, the objective lens 311a is moved in association with magnification change of the variable magnification optical system 311b. That is, in the medical stereo observation systems of the seventh embodiment, it is constituted so that the image-forming optical systems 311cL, 311cR, and the objective optical system 311a are moved in association with magnification change. According to the medical stereo observation system of the seventh embodiment, normal single zoom can be used and the constitution can be simplified. Furthermore, it becomes unnecessary to carry out adjustment to the variable magnification optical system for left eye and right eyes.

Other constitutions, performances and effects are almost the same as the medical stereo observation system of the fifth embodiment.

Eighth Embodiment

Figure 33:
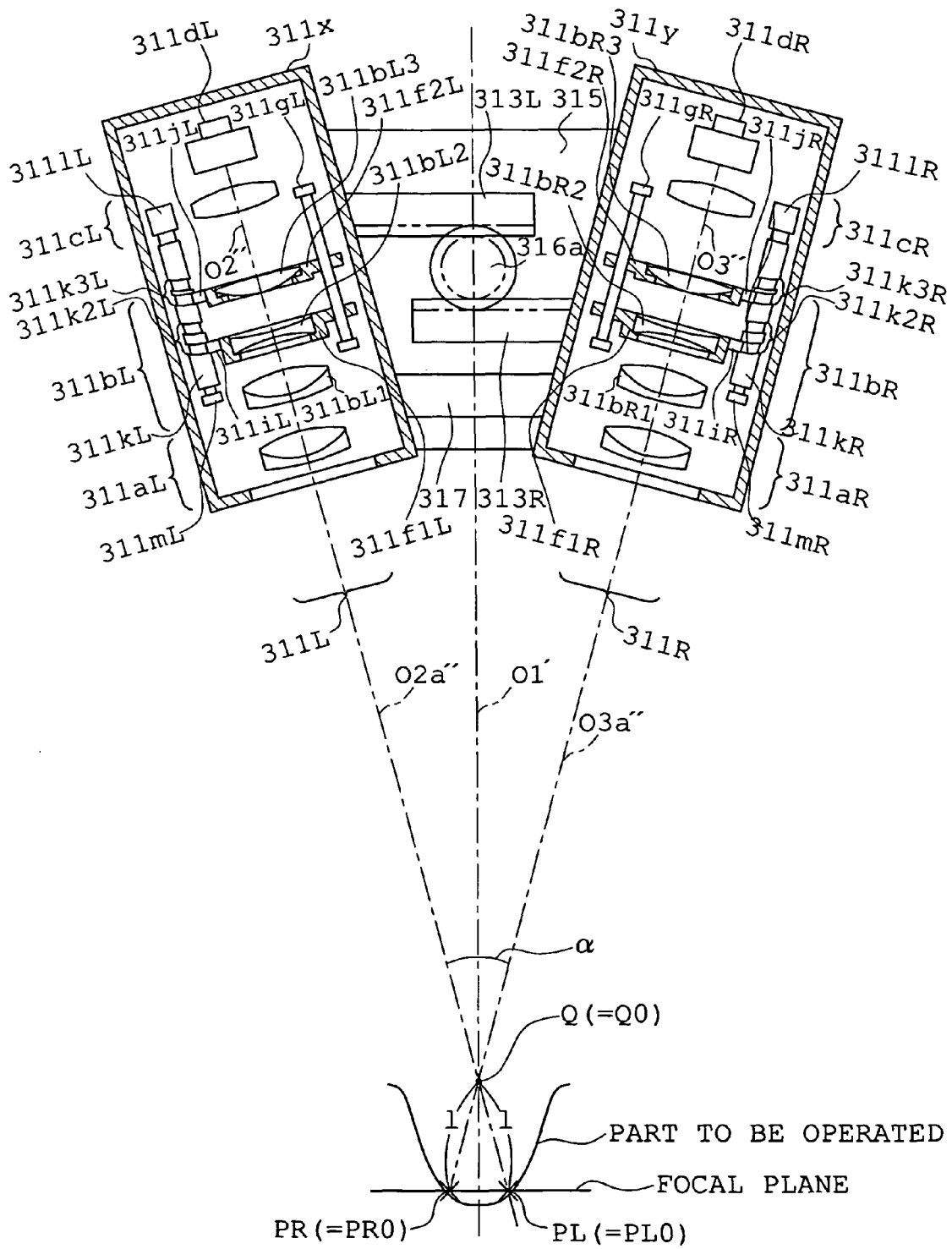
FIG. 33 is an explanatory view showing the optical structure of imaging optical systems for left and right eyes used in the medical stereo observation system of an eighth embodiment of the present invention, positions of individual optical members at a low magnification, an intersection of optical axes on the observation object side in the imaging optical systems for left and right eyes, and individual focal positions of the imaging optical systems for left and right eyes relative to a focal plane.
Figure 35A:
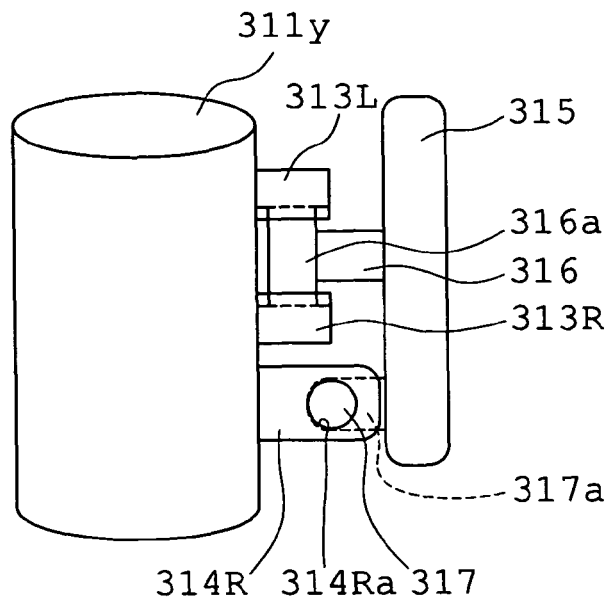
FIGS. 35A and 35B are side views of FIGS. 33 and 34, indicating a right side view and a left side, respectively.
Figure 35B:
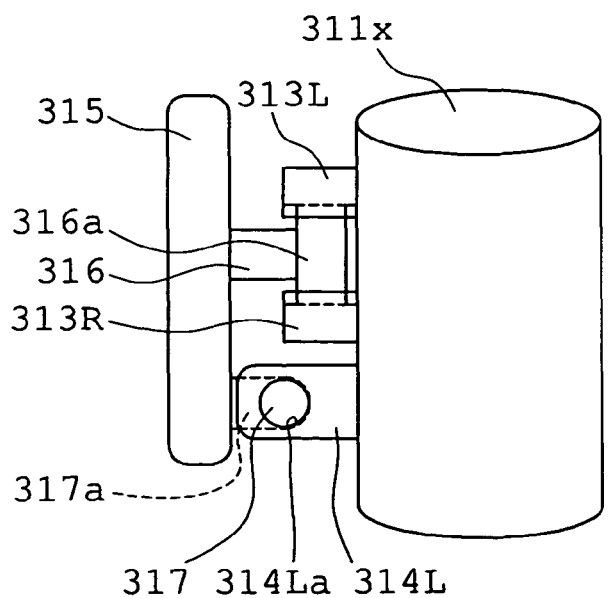

FIG. 33 is an explanatory view showing the optical structure of imaging optical systems for left and right eyes used in the medical stereo observation system of an eighth embodiment of the present invention, positions of individual optical components at a low magnification, an intersection of optical axes on the observation object side in the imaging optical systems for left and right eyes, and individual focal positions of the imaging optical systems for left and right eyes relative to a focal plane; FIG. 34 is an explanatory view showing the optical structure of imaging optical systems for left and right eyes used in the medical stereo observation system of the eighth embodiment, positions of individual optical components at a high magnification, an inter-section of optical axes on the observation object side in the imaging optical systems for left and right eyes, and individual focal positions of the imaging optical systems for left and right eyes relative to a focal plane; FIG. 41 is a side elevation of FIGS. 33 and 34; FIG. 35A shows right side views of these: and FIG. 35B shows left side views of these.

In the medical stereo observation system of the eighth embodiment, mirror parts of the stereo imaging apparatus 221 are constituted independently for left and right eyes.

At the inside of a mirror part 311x for left eye, there are an objective optical system for left eye 311aL; a variable magnification optical system for left eye 311bL; an image-forming optical system for left eye 311cL; an image sensor for left eye 311dL; magnification lens holding components for left eye 311f1L and 311f2L; a magnification lens guide component for left eye 311gL; magnification lens guide shafts for left eye 311iL and 311jL; a magnification lens drive cam shaft for left eye 311kL; a magnification lens drive motor for left eye 311IL; and an encoder for detecting an amount of magnification changes for left eye 311mL. The objective optical system for left eye 311aL; the variable magnification optical system for left eye 311bL; the image-forming optical system for left eye 311cL; and the image sensor for left eye 311dL are arranged on the central optical axis O2″ of the objective optical system 311aL for left eye at the inside of the mirror part for left eye.

At the inside of a mirror part 311y for right eye, there are an objective optical system for right eye 311aR; a variable magnification optical system for right eye 311bR; an image-forming optical system for right eye 311cR; an image sensor for right eye 311dR; magnification lens holding components for right eye 311f1R and 311f2R; a magnification lens guide component for right eye 311gR; magnification lens guide shafts for right eye 311iR and 311jR; a magnification lens drive cam shaft for right eye 311kR; a magnification lens drive motor for right eye 311IR; and an encoder for detecting an amount of magnification changes for right eye 311mR. The objective optical system for right eye 311aR; the variable magnification optical system for right eye 311bR; the image-forming optical system for right eye 311cR; and the image sensor for right eye 311dR are arranged on the central optical axis O3″ of the objective optical system 311aR for right eye at the inside of the mirror part for right eye.

The optical axes O2″ and O3″ are arranged at the same angle ($\alpha/2$) to a virtual line O1′ perpendicular to a focal plane. Therefore, the imaging optical system for left eye 311L and the imaging optical system for right eye 311R are arranged at an angle and at line symmetry to the virtual line O1′.

Detailed constitutions with respect to the magnification lens holding components for left eye 311f1L and 311f2L; the magnification lens guide component for left eye 311gRL; the magnification lens guide shafts for left eye 311iL and 311jL; the magnification lens drive cam shaft 311kL for left eye; and the magnification lens drive motor for left eye 311IL; the magnification lens holding component for right eye 311f1R and 311f2R; the magnification lens guide component for right eye 311gR; the magnification lens guide shafts for right eye 311iR and 311jR; the magnification lens drive cam shaft for right eye 311kR; and the magnification lens drive motor for right eye 311IR are almost the same as the constitutions in the medical stereo observation system of the fifth to seventh embodiments.

At the outside of the mirror parts for left and right eyes 311x and 311y, racks 313L and 313R, and guide hole parts 314L and 314R, are arranged respectively. A pinion 316a of a motor 316 fixed to a support part 315 engages with the racks 313L and 313R. In guide holes 314La and 314Ra of the guide hole parts 314L and 314R, a cylinder-shape guide component 317 fixed to the support part 315 via a guide fixing portion 317a arranged at the parts, are inserted through. Further, the mirror parts for left eye, and the mirror part for right eye are arranged with an angle so that an incident light axis of the imaging optical system built in each part may have an angle to the focal plane. And, the mirror part for left eye 311x and the mirror part for right eye 311y are constituted so as to be moved in parallel to the focal plane via the racks 313L and 313R, the guide hole parts 314L and 314R, and the guide 314, by the pinion 316a being rotated by driving the motor 316, and in association with magnification change of the variable magnification optical system 311bL and 311bR, FIG. 33 shows a state at a low magnification. The intersection Q of optical axes O2a″ and O3a″ at the observation object side in the image-forming optical systems 311cL and 311cR for left and right eyes are located at a predetermined position Q0 at the image pickup side rather than the focal plane in the observation object. At this time, each of focal positions PL and PR of the two imaging optical systems 311L and 311R for left and right eyes is located at predetermined positions PL0 and PR0 on the focal plane, respectively. In this state, if a magnification-change-switch which is not illustrated, is pushed by a person carrying out a surgical operation, the magnification lens drive motor for left and right eyes 311IL and 311IR are driven, and the magnification lens drive cam shafts for left and right eyes 311kL and 311kR are rotated, and, via the magnification lens guide grooves for left and right eyes 311k2L, 311k3L, 311k2R, 311k3R, 311k2R and 311k3R, the magnification lens guide shafts for left and right eyes 311iL, 311jL, 311iR and 311jR are moved toward a predetermined direction. And as shown in FIG. 34, the second and third lens groups 311bL2, 311bL3, 311bR2, and 311bR3 of the variable magnification optical systems 311bL and 311bR are moved toward the position shown by the solid line from the position shown by the dashed line at a low magnification. Thereby, magnification change is carried out.

At this time, encoders for detecting an amount of magnification change for right and left eyes 311mL and 311mR detect the amount of rotation of the magnification lens drive cam shafts for left and right eyes 311kL and 311kR, and transmit it as a signal, to a control part which is not illustrated. The control part, according to the inputted signal, computes the amount of movements of the mirror parts for left eye and right eyes 311x and 311y, and also computes the number of rotation of the motor 316 which is necessary for movement of the computed predetermined amount, and transmits the signal of the computed amount of rotation to the motor 316. The motor 316 is driven based on the transmitted number of rotation, and the pinion 316a is rotated. Thereby the mirror parts 311x and 311y for left and right eyes are moved toward a direction where these parts mutually approach in parallel to the focal plane, via the racks 313L and 313R, the guide hole parts 314L and 314R, and the guide 317, as shown by the dashed line in FIG. 34. Thus, while keeping the focal positions PL and PR, and an angle at which the imaging optical systems 311L and 311R for left and right eyes cross constant (keeping it as α), the intersection Q of optical axes O2a" and O3a" at the observation object side in the two imaging optical systems 311L and 311R is moved toward a position Q1 which is shifted by [(l'-l)cos(α/2)] in the direction of the focal plane. Thereby, the focal positions PL and PR seem to have been moved to a position corresponding to the focal plane to the intersection Q of the optical axes O2a and O3a at the observation object side in the two imaging optical systems 311L and 311R.

Therefore, according to the medical stereo observation system of the eighth embodiment, the amount of parallax on a display panel can be kept within an image fusible range without changing focal position. Furthermore, since an angle of intersection of the optical axes O2a" and O3a" at the observation object side in the two imaging optical systems 311L and 311R can be unchanged, an observation image with constant stereoscopic effect can be obtained. Since the amount of parallax can be set freely keeping a focal position, a presentation position of an image can be freely set up at a desired position. Other construction, function and effect are almost the same as the medical stereo observation system of the fifth embodiment.

What is claimed is:

1. A medical stereo observation system comprising:
a stereo imaging unit for producing a first image for a left eye and a second image for a right eye, the first image and the second image mutually having parallax; and
a stereo display unit for displaying stereoscopically the images produced by the stereo imaging unit,
wherein the stereo imaging unit has a first imaging optical system for producing the first image for the left eye and a second imaging optical system for producing the second image for the right eye, and focal positions of the first imaging optical system and the second imaging optical system are located on an object side of an intersection of optical axes of the first imaging optical system and the second imaging optical system.

2. A medical stereo observation system according to claim 1, wherein the following condition is satisfied:

$$\{5.9 \text{ (mm)} \times WD \text{ (mm)} \times \tan(\omega_1/2)\}/\{L \text{ (mm)} \times \tan(\alpha/2) + 5.9 \text{ (mm)} \times \tan(\omega_1/2)\}$$

$$\leq x \text{ (mm)} \leq$$

$$\{21.7 \text{ (mm)} \times WD \text{ (mm)} \times \tan(\omega_1/2)\}/\{L \text{ (mm)} \times \tan(\alpha/2) + 21.7 \text{ (mm)} \times \tan(\omega_1/2)\}$$

where x is a distance from the intersection of the optical axes of the first imaging optical system and the second imaging optical system to a straight light connecting a center of an object-side focal plane of the first imaging optical system with a center of an object-side focal plane of the second imaging optical system, WD is a working distance of the stereo imaging unit, which is defined as a distance from a most object-side surface of the stereo imaging unit to object-side focal positions of the stereo imaging unit, $\omega_1$ is a diagonal field angle of each of the first imaging optical system and the second imaging optical system, α is an angle made on the object side by the optical axes of the first imaging optical system and the second imaging optical system, and L is a diagonal distance of an observation image in the stereo display unit.

3. A medical stereo observation system according to claim 1, wherein each of the first imaging optical system and the second imaging optical system includes an objective optical system, a variable magnification optical system, an image-forming optical system, and an image sensor, and the focal positions of the first imaging optical system and the second imaging optical system are adapted to be shifted in reference to the intersection of the optical axes of the first imaging optical system and the second imaging optical system toward the intersection of the optical axes of the first imaging optical system and the second imaging optical system in association with a magnification change by the variable magnification optical systems from a lowest magnification state toward a higher magnification state.

4. A medical stereo observation system according to claim 3, further comprising intersection position shifting means for shifting the intersection of the optical axes of the first imaging optical system and the second imaging optical system toward the object side in association with the magnification change by the variable magnification optical systems.

5. A medical stereo observation system according to claim 4, wherein the intersection position shifting means shifts the intersection of the optical axes of the first imaging optical system and the second imaging optical system so as to cancel a gap between a preset desired depth position for observation, in an observation object having a depth, and the focal positions of the first imaging optical system and the second imaging optical system, the gap being caused by a shift of the focal positions in association with a magnification change by the variable magnification optical systems.

6. A medical stereo observation system according to claim 4, wherein the intersection position shifting means moves the first imaging optical system and the second imaging optical system along a straight line connecting the focal positions of the first imaging optical system and the second imaging optical system in association with the magnification change by the variable magnification optical systems.

7. A medical stereo observation system according to claim 6, wherein the first imaging optical system and second imaging optical system are adapted to be moved in association with the magnification change by the variable magnification optical systems in such a manner that the following condition is satisfied:

$$l \cdot \beta \cdot \sin(\alpha/2) = l' \cdot \beta' \cdot \sin(\alpha'/2)$$

where α, l and β represent: an angle at which the optical axes of the first imaging optical system and the second imaging optical system cross; a distance from the focal position of each of the first imaging optical system and the second imaging optical system, along the optical axis thereof, to the intersection of the optical axes of the first imaging optical system and the second imaging optical system; and a magnification of the variable magnification optical system of each of the first imaging optical system and the second imaging optical system, respectively, in a first magnification state; and where α', l' and β' represent: an angle at which the optical axes of the first imaging optical system and the second imaging optical system cross; a distance from the focal position of each of the first imaging optical system and the second imaging optical system, along the optical axis thereof, to the intersection of the optical axes of the first imaging optical system and the second imaging optical system; and a magnification of the variable magnification optical system of each of the first imaging optical system and the second imaging optical system, respectively, in a second magnification state different from the first magnification state.

8. A medical stereo observation system according to claim 4, wherein an angle $\alpha$ at which the optical axes of the first imaging optical system and the second imaging optical system cross is kept constantly in a variable magnification mode ranging from the lowest magnification state to a highest magnification state.

9. A medical stereo observation system according to claim 8, wherein when a distance, measured along the optical axis, from each of the focal positions of the first imaging optical system and the second imaging optical system to the intersection of the optical axes of the first imaging optical system and the second imaging optical system is changed from l to l' in accordance with the magnification change by the variable magnification optical systems, the intersection position shifting means shifts the position of the intersection of the optical axes of the first imaging optical system and the second imaging optical system by (l-l')cos($\alpha$/2).

10. A medical stereo observation system according to claim 3, wherein the focal positions of the first imaging optical system and the second imaging optical system are shifted in association with the magnification change by the variable magnification optical systems in such a manner that the following condition is satisfied:

$$l \cdot \beta \cdot \sin(\alpha/2) = l' \cdot \beta' \cdot \sin(\alpha'/2)$$

where $\alpha$, l and $\beta$ represent: an angle at which the optical axes of the first imaging optical system and the second imaging optical system cross; a distance from the focal position of each of the first imaging optical system and the second imaging optical system, along the optical axis thereof, to the intersection of the optical axes of the first imaging optical system and the second imaging optical system; and a magnification of the variable magnification optical system of each of the first imaging optical system and the second imaging optical system, respectively, in a first magnification state; and where $\alpha'$, l' and $\beta'$ represent: an angle at which the optical axes of the first imaging optical system and the second imaging optical system cross; a distance from the focal position of each of the first imaging optical system and the second imaging optical system, along the optical axis thereof, to the intersection of the optical axes of the first imaging optical system and the second imaging optical system; and a magnification of the variable magnification optical system of each of the first imaging optical system and the second imaging optical system, respectively, in a second magnification state different from the first magnification state.

11. A medical stereo observation system according to claim 3, further comprising image-forming optical system moving means for moving the image-forming optical systems along optical axes of the image-forming optical systems in association with the magnification change by the variable magnification optical systems.

12. A medical stereo observation system according to claim 11, wherein the image-forming optical system moving means moves the focal positions of the first imaging optical system and the second imaging optical system in association with the magnification change by the variable magnification optical systems in such a manner that the following condition is satisfied:

$$l \cdot \beta \cdot \sin(\alpha/2) = l' \cdot \beta' \cdot \sin(\alpha'/2)$$

where $\alpha$, l and $\beta$ represent: an angle at which the optical axes of the first imaging optical system and the second imaging optical system cross; a distance from the focal position of each of the first imaging optical system and the second imaging optical system, along the optical axis thereof, to the intersection of the optical axes of the first imaging optical system and the second imaging optical system; and a magnification of the variable magnification optical system of each of the first imaging optical system and the second imaging optical system, respectively, in a first magnification state; and where $\alpha'$, l' and $\beta'$ represent: an angle at which the optical axes of the first imaging optical system and the second imaging optical system cross; a distance from the focal position of each of the first imaging optical system and the second imaging optical system, along the optical axis thereof, to the intersection of the optical axes of the first imaging optical system and the second imaging optical system; and a magnification of the variable magnification optical system of each of the first imaging optical system and the second imaging optical system, respectively, in a second magnification state different from the first magnification state.

13. A medical stereo observation system according to claim 3, wherein an angle $\alpha$ at which the optical axes of the first imaging optical system and the second imaging optical system cross is kept constantly in a variable magnification mode ranging from the lowest magnification state to a highest magnification state.

* * * * *